US011505574B2

(12) United States Patent
Chen et al.

(10) Patent No.: US 11,505,574 B2
(45) Date of Patent: Nov. 22, 2022

(54) MODULATION OF P53 FOR THE TREATMENT OF CANCER

(71) Applicant: THE REGENTS OF THE UNIVERSITY OF CALIFORNIA, Oakland, CA (US)

(72) Inventors: Xinbin Chen, Davis, CA (US); Christopher A. Lucchesi, Davis, CA (US); Jin Zhang, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/422,850

(22) Filed: May 24, 2019

(65) Prior Publication Data

US 2020/0087345 A1  Mar. 19, 2020

Related U.S. Application Data

(63) Continuation of application No. PCT/US2017/063537, filed on Nov. 29, 2017.

(60) Provisional application No. 62/427,517, filed on Nov. 29, 2016.

(51) Int. Cl.
| | |
|---|---|
| *C07K 7/06* | (2006.01) |
| *A61K 47/66* | (2017.01) |
| *A61K 47/64* | (2017.01) |
| *A61P 35/00* | (2006.01) |
| *A61K 47/42* | (2017.01) |
| *A61K 45/06* | (2006.01) |

(52) U.S. Cl.
CPC ............... *C07K 7/06* (2013.01); *A61K 47/42* (2013.01); *A61K 47/64* (2017.08); *A61K 47/66* (2017.08); *A61P 35/00* (2018.01); *A61K 45/06* (2013.01)

(58) Field of Classification Search
CPC ............... A61K 2300/00; A61K 38/00; A61K 2039/5156; A61K 48/00; A61K 2039/5152; A61K 47/64; A61K 47/6867; A61K 2217/052; C12Q 1/6886; A61P 35/04; A61P 31/00; C12N 2310/3519; C12N 9/90; C12N 2320/31; G01N 2800/52; C07K 14/47; C07K 16/32; C07K 2319/00; C07K 14/4746; C07K 7/64; A01K 2217/052
See application file for complete search history.

(56) References Cited

U.S. PATENT DOCUMENTS

| 5,175,146 A | 12/1992 | Basava et al. |
| 2005/0267037 A1 | 12/2005 | Anderson et al. |
| 2009/0226429 A1* | 9/2009 | Salcedo ............. C07K 16/2878 424/133.1 |
| 2014/0010861 A1 | 1/2014 | Bancel et al. |
| 2014/0147454 A1* | 5/2014 | Chakraborty .......... A61P 37/06 536/23.1 |
| 2014/0234255 A1* | 8/2014 | Lai ..................... C07K 14/4708 424/93.2 |
| 2014/0303084 A1* | 10/2014 | Thorn .................. C07K 14/745 514/13.7 |
| 2015/0099791 A1 | 4/2015 | Krieg et al. |
| 2015/0112043 A1 | 4/2015 | Guo et al. |
| 2016/0145299 A1 | 5/2016 | Divita et al. |

FOREIGN PATENT DOCUMENTS

| DK | WO2004110349 A2 * | 12/2004 | |
| WO | WO2014160508 A1 * | 10/2014 | ............. C07K 19/00 |
| WO | 2018102317 A1 | 6/2018 | |

OTHER PUBLICATIONS

NCBI (NP_059965.2). RNA-binding protein 38 isoform a https://www.ncbi.nlm.nih.gov/protein/NP_059965.2[Aug. 2, 2020 12:10:27 PM] (Year: 2020).*
Xue et al. RNA-binding protein RNPC1: acting as a tumor suppressor in breast cancer. BMC Cancer 2014, 14:322. (Year: 2014).*
Lao et al. Liposomal Doxorubicin in the Treatment of Breast Cancer Patients: A Review. Journal of Drug Delivery. vol. 2013, Article ID 456409. (Year: 2013).*
Patel et al. Conjugation with Cationic Cell-Penetrating Peptide Increases Pulmonary Absorption of Insulin. Mol Pharm. 2009; 6(2): 492-503. (Year: 2009).*
Sang Hoon Joo. Cyclic Peptides as Therapeutic Agents and Biochemical Tools. Biomol Ther. 2012; 20(1): 19-26. (Year: 2012).*
Tegge et al. Synthesis of cyclic peptides and peptide libraries on a new disulfide linker. J. Pept. Sci. 2007; 13: 693-699. (Year: 2007).*
Prezma et al. VDAC1-based peptides: novel pro-apoptotic agents and potential therapeutics for B-cell chronic lymphocytic leukemia. Cell Death and Disease (2013) 4, e809: 1-11. (Year: 2013).*
Hilarie et al. Fluorescence-Quenched Solid Phase Combinatorial Libraries in the Characterization of Cysteine Protease Substrate Specificity. J. Comb. Chem. 1999, 1, 509-523. (Year: 1999).*
Li et al. Papain bioinspired gold nanoparticles augmented the anticancer potency of 5-FU against lung cancer. Journal of Experimental Nanoscience, 2020; 15(1): 109-128. (Year: 2020).*
Oomen et al. Crystal Structure of an Anti-meningococcal Subtype P1.4 PorA Antibody Provides Basis for Peptide-Vaccine Design. J. Mol. Biol. (2005) 351, 1070-1080. (Year: 2005).*
Lim et al. Use of Cell-Penetrating Peptides in Dendritic Cell-Based Vaccination. Immune Network vol. 16, No. 1: 33-43, Feb. 2016. (Year: 2016).*

(Continued)

*Primary Examiner* — Aradhana Sasan
*Assistant Examiner* — Jia-Hai Lee
(74) *Attorney, Agent, or Firm* — Kilpatrick Townsend & Stockton LLP

(57) ABSTRACT

The invention provides compositions and methods for preventing or treating cancer in a subject. In some embodiments, the compositions comprise isolated peptides and/or isolated oligonucleotides. In other embodiments, peptides of the present invention are conjugated with cell-penetrating peptides. Vectors, cells, and kits for preventing or treating cancer are also provided herein.

33 Claims, 44 Drawing Sheets

Specification includes a Sequence Listing.

(56) References Cited

OTHER PUBLICATIONS

Gao et al., "Integrative Analysis of Complex Cancer Genomics and Clinical Profiles Using the cBioPortal," Science Signaling, Apr. 2, 2013, vol. 6, Issue 269, 20 pages.

Jiang et al., "Rbm24, an RNA-binding Protein and a Target of p53, Regulates p21 Expression via mRNA Stability," The Journal of Biological Chemistry, Feb. 7, 2014, vol. 289, No. 6, pp. 3164-3175.

Montero et al., "eIF4E as a Control Target for Viruses," Viruses, 2015, vol. 7, pp. 739-750.

Shu et al., "RNPC1, an RNA-binding protein and a target of the p53 family, is required for maintaining the stability of the basal and stress-induced p21 transcript," Genes and Development, 2006, vol. 20, pp. 2961-2972.

Zhang et al., "Translational repression of p53 by RNPC1, a p53 target overexpressed in Tymphomas," Genes and Development, 2011, vol. 25, pp. 1528-1543.

Zhang et al., "Glycogen synthase kinase 3 promotes p53 mRNA translation via phosphorylation of RNPC1," Genes and Development, 2013, vol. 27, pp. 2246-2258.

\* cited by examiner

180-QYPPATYDQYPYAASPATAASFVGYSYPAAVPQALSAAAP – 220
(40aa) (SEQ ID NO:2)

194 – IGYQSHADTATKSGSTTKNRFVV – 217
(23aa) (SEQ ID NO:3)

RBM38  180 — 220 eIF4E  195 — 217

RKO

MCF7

RBM38: QYPPATYDQYPYAASPATAASFVGYSYPAAVPQALSAAAP (SEQ ID NO:2)

RBM24: YPYAASPAAAGYVTAGGYGYAVQQP (SEQ ID NO:4)

MCF7 375nM

RKO 150nM

MCF7 50nM

MCF7 150nM

FIG. 17E
FIG. 17F
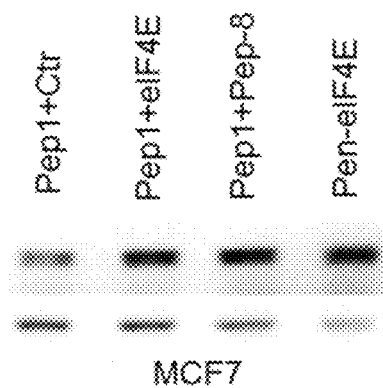
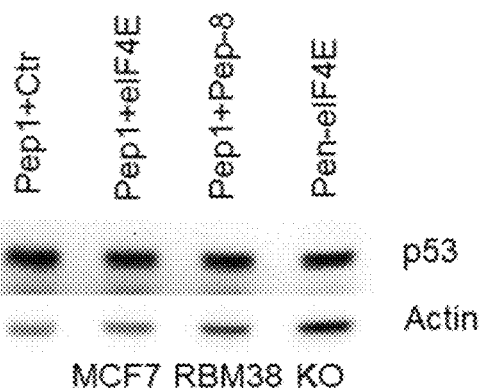
FIG. 17G
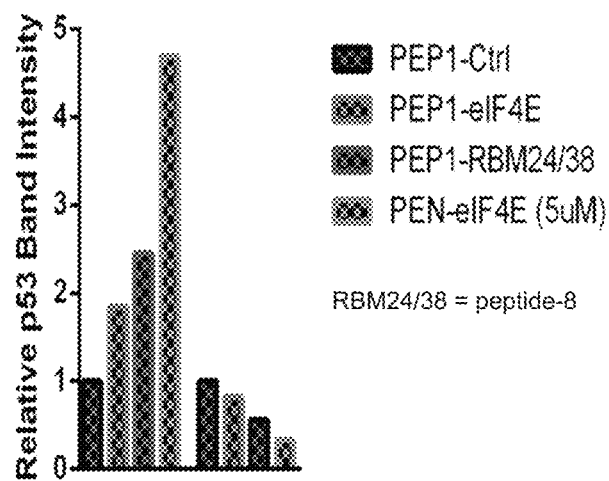

3.125ng/mL Doxorubicin (MCF7)

3.125ng/mL Doxorubicin (RKO)

Peptide bound to tentagel
beads used to pull down
eIF4E

...GAGGATTTCATCTCTTGTATATGATGATCTGGATC
CACCAAGACTTGTTTTATGCTCAGGGTCAA<u>TTTCTT
TTTTCTTTTTTTTTTTTTTTTTTTTCTTTTTCTTT</u>GAGAC
TGGGTCTCGCTTTGTTGCCAGGCTGGAGTG...
(Exon 11) (SEQ ID NO:42)

18T:  5' <u>TTTCTTTTTTCTTTTTTTTTTTTTT
TTTTCTTTTTCTT</u> 3'
(SEQ ID NO:15)

14A/G:  5' AAAAAAGAAAAAAA 3'
(SEQ ID NO:20)

15A:  5' AAAAAAAAAAAAAAA 3'
(SEQ ID NO:21)

RKO 48hrs 5um Oligo

MCF10A 24hr 5 μM

RKO 24hrs SuM Oligo

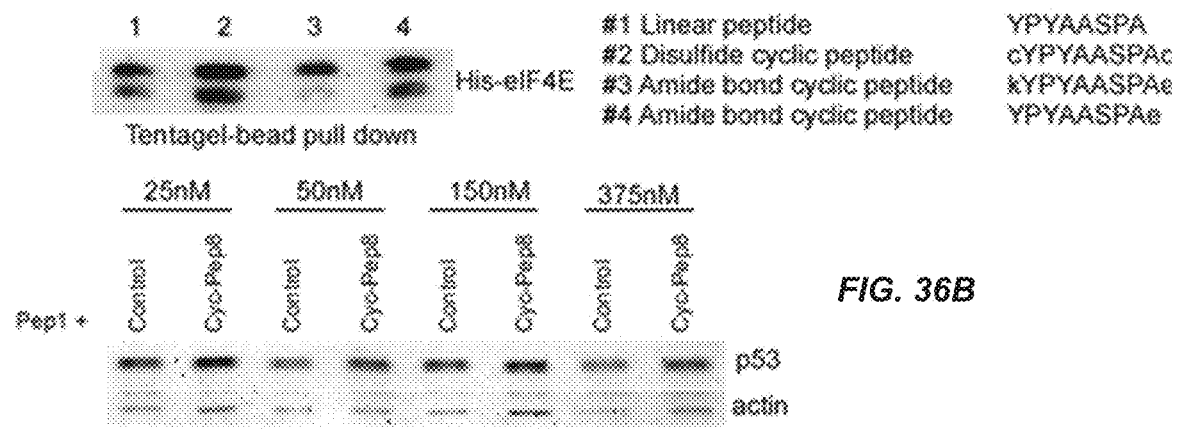
FIG. 36A
FIG. 36B
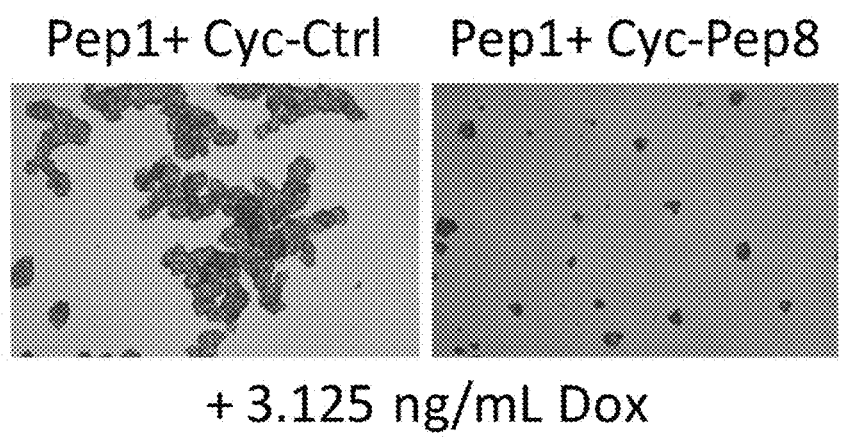
FIG. 36C

SEQUENCE LISTING

<160> NUMBER OF SEQ ID NOS: 65

<210> SEQ ID NO 1
<211> LENGTH: 8
<212> TYPE: PRT
<213> ORGANISM: Artificial Sequence
<220> FEATURE:
<223> OTHER INFORMATION: Synthetic construct

<400> SEQUENCE: 1

Tyr Pro Tyr Ala Ala Ser Pro Ala
1               5

<210> SEQ ID NO 2
<211> LENGTH: 40
<212> TYPE: PRT
<213> ORGANISM: Artificial Sequence
<220> FEATURE:
<223> OTHER INFORMATION: Synthetic construct

<400> SEQUENCE: 2

Gln Tyr Pro Pro Ala Thr Tyr Asp Gln Tyr Pro Tyr Ala Ala Ser Pro
1               5                   10                  15

Ala Thr Ala Ala Ser Phe Val Gly Tyr Ser Tyr Pro Ala Ala Val Pro
            20                  25                  30

Gln Ala Leu Ser Ala Ala Ala Pro
        35                  40

<210> SEQ ID NO 3
<211> LENGTH: 23
<212> TYPE: PRT
<213> ORGANISM: Artificial Sequence
<220> FEATURE:
<223> OTHER INFORMATION: Synthetic construct

<400> SEQUENCE: 3

Ile Gly Tyr Gln Ser His Ala Asp Thr Ala Thr Lys Ser Gly Ser Thr
1               5                   10                  15

Thr Lys Asn Arg Phe Val Val
            20

```
<210> SEQ ID NO 4
<211> LENGTH: 25
<212> TYPE: PRT
<213> ORGANISM: Artificial Sequence
<220> FEATURE:
<223> OTHER INFORMATION: Synthetic construct

<400> SEQUENCE: 4

Tyr Pro Tyr Ala Ala Ser Pro Ala Ala Ala Gly Tyr Val Thr Ala Gly
1               5                   10                  15

Gly Tyr Gly Tyr Ala Val Gln Gln Pro
            20                  25

<210> SEQ ID NO 5
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = D-cysteine
<220> FEATURE:
<221> NAME/KEY: MISC_FEATURE
<222> LOCATION: (10)..(10)
<223> OTHER INFORMATION: Xaa = D-cysteine

<400> SEQUENCE: 5

Xaa Tyr Pro Tyr Ala Ala Ser Pro Ala Xaa
1               5                   10

<210> SEQ ID NO 6
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = D-cysteine
<220> FEATURE:
<221> NAME/KEY: MISC_FEATURE
<222> LOCATION: (25)..(25)
<223> OTHER INFORMATION: Xaa = D-cysteine

<400> SEQUENCE: 6

Xaa Ile Gly Tyr Gln Ser His Ala Asp Thr Ala Thr Lys Ser Gly Ser
1               5                   10                  15

Thr Thr Lys Asn Arg Phe Val Val Xaa
            20                  25

<210> SEQ ID NO 7
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (9)..(9)
<223> OTHER INFORMATION: Xaa = D-glutamic acid

<400> SEQUENCE: 7

Tyr Pro Tyr Ala Ala Ser Pro Ala Xaa
1               5
```

<210> SEQ ID NO 8
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = D-lysine
<220> FEATURE:
<221> NAME/KEY: MISC_FEATURE
<222> LOCATION: (10)..(10)
<223> OTHER INFORMATION: Xaa = D-glutamic acid

<400> SEQUENCE: 8

Xaa Tyr Pro Tyr Ala Ala Ser Pro Ala Xaa
1               5                   10

<210> SEQ ID NO 9
<211> LENGTH: 39
<212> TYPE: PRT
<213> ORGANISM: Artificial Sequence
<220> FEATURE:
<223> OTHER INFORMATION: Synthetic construct

<400> SEQUENCE: 9

Arg Gln Ile Lys Ile Trp Phe Gln Asn Arg Arg Met Lys Trp Lys Lys
1               5                   10                  15

Ile Gly Tyr Gln Ser His Ala Asp Thr Ala Thr Lys Ser Gly Ser Thr
            20                  25                  30

Thr Lys Asn Arg Phe Val Val
        35

<210> SEQ ID NO 10
<211> LENGTH: 27
<212> TYPE: PRT
<213> ORGANISM: Artificial Sequence
<220> FEATURE:
<223> OTHER INFORMATION: Synthetic construct

<400> SEQUENCE: 10

Arg Gln Ile Lys Ile Trp Phe Gln Asn Arg Arg Met Lys Trp Lys Lys
1               5                   10                  15

Ser Thr Leu Trp Asp Thr Ala Glu Leu Trp Gln
            20                  25

<210> SEQ ID NO 11
<211> LENGTH: 11
<212> TYPE: PRT
<213> ORGANISM: Artificial Sequence
<220> FEATURE:
<223> OTHER INFORMATION: Synthetic construct

<400> SEQUENCE: 11

Ser Thr Leu Trp Asp Thr Ala Glu Leu Trp Gln
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Synthetic construct

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = N-acetyl-lysine
<220> FEATURE:
<221> NAME/KEY: MISC_FEATURE
<222> LOCATION: (21)..(21)
<223> OTHER INFORMATION: Xaa = Valine amide

<400> SEQUENCE: 13

Xaa Glu Thr Trp Trp Glu Thr Trp Trp Thr Glu Trp Ser Gln Pro Lys
1               5                   10                  15

Lys Lys Arg Lys Xaa
            20

<210> SEQ ID NO 14
<211> LENGTH: 15
<212> TYPE: DNA
<213> ORGANISM: Artificial Sequence
<220> FEATURE:
<223> OTHER INFORMATION: Synthetic construct

<400> SEQUENCE: 14
gacacgcttc ccaaa                                                    15

<210> SEQ ID NO 15
<211> LENGTH: 38
<212> TYPE: DNA
<213> ORGANISM: Artificial Sequence
<220> FEATURE:
<223> OTHER INFORMATION: Synthetic construct

<400> SEQUENCE: 15
tttctttttt cttttttttt ttttttttc ttttcctt                            38

<210> SEQ ID NO 16
<211> LENGTH: 38
<212> TYPE: DNA
<213> ORGANISM: Artificial Sequence
<220> FEATURE:
<223> OTHER INFORMATION: Synthetic construct

<400> SEQUENCE: 16
aaagaaaaaa gaaaaaaaaa aaaaaaaag aaaagaa                             38

<210> SEQ ID NO 17
<211> LENGTH: 29
<212> TYPE: DNA
<213> ORGANISM: Artificial Sequence
<220> FEATURE:
<223> OTHER INFORMATION: Synthetic construct

<400> SEQUENCE: 17
aaagaaaaaa gaaaaaaaaa aaaaaaaa                                      29

<210> SEQ ID NO 18
<211> LENGTH: 19
<212> TYPE: DNA

<213> ORGANISM: Artificial Sequence
<220> FEATURE:
<223> OTHER INFORMATION: Synthetic construct

<400> SEQUENCE: 18
aaagaaaaaa gaaaaaaaa                                              19

<210> SEQ ID NO 19
<211> LENGTH: 15
<212> TYPE: DNA
<213> ORGANISM: Artificial Sequence
<220> FEATURE:
<223> OTHER INFORMATION: Synthetic construct

<400> SEQUENCE: 19
aaagaaaaaa gaaaa                                                  15

<210> SEQ ID NO 20
<211> LENGTH: 15
<212> TYPE: DNA
<213> ORGANISM: Artificial Sequence
<220> FEATURE:
<223> OTHER INFORMATION: Synthetic construct

<400> SEQUENCE: 20
aaaaaagaaa aaaaa                                                  15

<210> SEQ ID NO 21
<211> LENGTH: 18
<212> TYPE: DNA
<213> ORGANISM: Artificial Sequence
<220> FEATURE:
<223> OTHER INFORMATION: Synthetic construct

<400> SEQUENCE: 21
aaaaaaaaaa aaaaaaaa                                               18

<210> SEQ ID NO 22
<211> LENGTH: 239
<212> TYPE: PRT
<213> ORGANISM: Homo sapiens

<400> SEQUENCE: 22

Met Leu Leu Gln Pro Ala Pro Cys Ala Pro Ser Ala Gly Phe Pro Arg
1               5                   10                  15

Pro Leu Ala Ala Pro Gly Ala Met His Gly Ser Gln Lys Asp Thr Thr
            20                  25                  30

Phe Thr Lys Ile Phe Val Gly Gly Leu Pro Tyr His Thr Thr Asp Ala
        35                  40                  45

Ser Leu Arg Lys Tyr Phe Glu Gly Phe Gly Asp Ile Glu Glu Ala Val
    50                  55                  60

Val Ile Thr Asp Arg Gln Thr Gly Lys Ser Arg Gly Tyr Gly Phe Val
65                  70                  75                  80

Thr Met Ala Asp Arg Ala Ala Ala Glu Arg Ala Cys Lys Asp Pro Asn
                85                  90                  95

Pro Ile Ile Asp Gly Arg Lys Ala Asn Val Asn Leu Ala Tyr Leu Gly
            100                 105                 110

Ala Lys Pro Arg Ser Leu Gln Thr Gly Phe Ala Ile Gly Val Gln Gln
        115                 120                 125

Leu His Pro Thr Leu Ile Gln Arg Thr Tyr Gly Leu Thr Pro His Tyr
    130                 135                 140

```
Ile Tyr Pro Pro Ala Ile Val Gln Pro Ser Val Val Ile Pro Ala Ala
145                 150                 155                 160

Pro Val Pro Ser Leu Ser Ser Pro Tyr Ile Glu Tyr Thr Pro Ala Ser
            165                 170                 175

Pro Ala Tyr Ala Gln Tyr Pro Pro Ala Thr Tyr Asp Gln Tyr Pro Tyr
        180                 185                 190

Ala Ala Ser Pro Ala Thr Ala Ala Ser Phe Val Gly Tyr Ser Tyr Pro
    195                 200                 205

Ala Ala Val Pro Gln Ala Leu Ser Ala Ala Ala Pro Ala Gly Thr Thr
210                 215                 220

Phe Val Gln Tyr Gln Ala Pro Gln Leu Gln Pro Asp Arg Met Gln
225                 230                 235
```

<210> SEQ ID NO 23
<211> LENGTH: 217
<212> TYPE: PRT
<213> ORGANISM: Homo sapiens

<400> SEQUENCE: 23

```
Met Ala Thr Val Glu Pro Glu Thr Thr Pro Thr Pro Asn Pro Pro Thr
1               5                   10                  15

Thr Glu Glu Glu Lys Thr Glu Ser Asn Gln Val Ala Asn Pro Glu
            20                  25                  30

His Tyr Ile Lys His Pro Leu Gln Asn Arg Trp Ala Leu Trp Phe Phe
        35                  40                  45

Lys Asn Asp Lys Ser Lys Thr Trp Gln Ala Asn Leu Arg Leu Ile Ser
    50                  55                  60

Lys Phe Asp Thr Val Glu Asp Phe Trp Ala Leu Tyr Asn His Ile Gln
65                  70                  75                  80

Leu Ser Ser Asn Leu Met Pro Gly Cys Asp Tyr Ser Leu Phe Lys Asp
                85                  90                  95

Gly Ile Glu Pro Met Trp Glu Asp Glu Lys Asn Lys Arg Gly Gly Arg
            100                 105                 110

Trp Leu Ile Thr Leu Asn Lys Gln Gln Arg Arg Ser Asp Leu Asp Arg
        115                 120                 125

Phe Trp Leu Glu Thr Leu Leu Cys Leu Ile Gly Glu Ser Phe Asp Asp
130                 135                 140

Tyr Ser Asp Asp Val Cys Gly Ala Val Val Asn Val Arg Ala Lys Gly
145                 150                 155                 160

Asp Lys Ile Ala Ile Trp Thr Thr Glu Cys Glu Asn Arg Glu Ala Val
                165                 170                 175

Thr His Ile Gly Arg Val Tyr Lys Glu Arg Leu Gly Leu Pro Pro Lys
            180                 185                 190

Ile Val Ile Gly Tyr Gln Ser His Ala Asp Thr Ala Thr Lys Ser Gly
        195                 200                 205

Ser Thr Thr Lys Asn Arg Phe Val Val
    210                 215
```

<210> SEQ ID NO 24
<211> LENGTH: 236
<212> TYPE: PRT
<213> ORGANISM: Homo sapiens
<220> FEATURE:
<221> NAME/KEY: MISC_FEATURE
<222> LOCATION: (99)..(99)
<223> OTHER INFORMATION: Xaa = any amino acid

<400> SEQUENCE: 24

```
Met His Thr Thr Gln Lys Asp Thr Thr Tyr Thr Lys Ile Phe Val Gly
1               5                   10                  15

Gly Leu Pro Tyr His Thr Thr Asp Ala Ser Leu Arg Lys Tyr Phe Glu
            20                  25                  30

Val Phe Gly Glu Ile Glu Glu Ala Val Val Ile Thr Asp Arg Gln Thr
        35                  40                  45

Gly Lys Ser Arg Gly Tyr Gly Phe Val Thr Met Ala Asp Arg Ala Ala
    50                  55                  60

Ala Glu Arg Ala Cys Lys Asp Pro Asn Pro Ile Ile Asp Gly Arg Lys
65                  70                  75                  80

Ala Asn Val Asn Leu Ala Tyr Leu Gly Ala Lys Pro Arg Ile Met Gln
                85                  90                  95

Pro Gly Xaa Ala Phe Gly Val Gln Gln Leu His Pro Ala Leu Ile Gln
            100                 105                 110

Arg Pro Phe Gly Ile Pro Ala His Tyr Val Tyr Pro Gln Ala Phe Val
            115                 120                 125

Gln Pro Gly Val Val Ile Pro His Val Gln Pro Thr Ala Ala Ala Ala
            130                 135                 140

Ser Thr Thr Pro Tyr Ile Asp Tyr Thr Gly Ala Ala Tyr Ala Gln Tyr
145                 150                 155                 160

Ser Ala Ala Ala Ala Ala Ala Ala Ala Tyr Asp Gln Tyr
            165                 170                 175

Pro Tyr Ala Ala Ser Pro Ala Ala Gly Tyr Val Thr Ala Gly Gly
            180                 185                 190

Tyr Gly Tyr Ala Val Gln Gln Pro Ile Thr Ala Ala Pro Gly Thr
            195                 200                 205

Ala Ala Ala Ala Ala Ala Ala Ala Ala Ala Ala Phe Gly Gln
            210                 215                 220

Tyr Gln Pro Gln Gln Leu Gln Thr Asp Arg Met Gln
225                 230                 235

<210> SEQ ID NO 25
<211> LENGTH: 11
<212> TYPE: PRT
<213> ORGANISM: Artificial Sequence
<220> FEATURE:
<223> OTHER INFORMATION: Synthetic construct

<400> SEQUENCE: 25

Tyr Gly Arg Lys Lys Arg Arg Gln Arg Arg Arg
1               5                   10

<210> SEQ ID NO 26
<211> LENGTH: 18
<212> TYPE: PRT
<213> ORGANISM: Artificial Sequence
<220> FEATURE:
<223> OTHER INFORMATION: Synthetic construct

<400> SEQUENCE: 26

Arg Gly Gly Arg Leu Ser Tyr Ser Arg Arg Phe Ser Thr Ser Thr
1               5                   10                  15

Gly Arg

<210> SEQ ID NO 27
<211> LENGTH: 10
<212> TYPE: PRT
<213> ORGANISM: Artificial Sequence
```

```
<220> FEATURE:
<223> OTHER INFORMATION: Synthetic construct

<400> SEQUENCE: 27

Arg Arg Leu Ser Tyr Ser Arg Arg Phe
1               5

<210> SEQ ID NO 28
<211> LENGTH: 12
<212> TYPE: PRT
<213> ORGANISM: Artificial Sequence
<220> FEATURE:
<223> OTHER INFORMATION: Synthetic construct

<400> SEQUENCE: 28

Pro Ile Arg Arg Arg Lys Lys Leu Arg Arg Leu Lys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic construct

<400> SEQUENCE: 29

Arg Arg Gln Arg Arg Thr Ser Lys Leu Met Lys Arg
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Synthetic construct

<400> SEQUENCE: 30

Arg Arg Arg Arg Asn Arg Thr Arg Arg Asn Arg Arg Arg Val Arg
1               5                   10                  15

<210> SEQ ID NO 31
<211> LENGTH: 19
<212> TYPE: PRT
<213> ORGANISM: Artificial Sequence
<220> FEATURE:
<223> OTHER INFORMATION: Synthetic construct

<400> SEQUENCE: 31

Lys Met Thr Arg Ala Gln Arg Arg Ala Ala Ala Arg Arg Asn Arg Trp
1               5                   10                  15

Thr Ala Arg

<210> SEQ ID NO 32
<211> LENGTH: 13
<212> TYPE: PRT
<213> ORGANISM: Artificial Sequence
<220> FEATURE:
<223> OTHER INFORMATION: Synthetic construct

<400> SEQUENCE: 32

Thr Arg Arg Gln Arg Thr Arg Arg Ala Arg Arg Asn Arg
1               5                   10

<210> SEQ ID NO 33
<211> LENGTH: 13
<212> TYPE: PRT
```

<213> ORGANISM: Artificial Sequence
<220> FEATURE:
<223> OTHER INFORMATION: Synthetic construct

<400> SEQUENCE: 33

Gly Arg Lys Lys Arg Gln Arg Arg Pro Pro Gln
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic construct

<400> SEQUENCE: 34

Gly Arg Arg Arg Arg Arg Arg Arg Arg Pro Pro Gln
1               5                   10

<210> SEQ ID NO 35
<211> LENGTH: 27
<212> TYPE: PRT
<213> ORGANISM: Artificial Sequence
<220> FEATURE:
<223> OTHER INFORMATION: Synthetic construct

<400> SEQUENCE: 35

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 36
<211> LENGTH: 17
<212> TYPE: PRT
<213> ORGANISM: Artificial Sequence
<220> FEATURE:
<223> OTHER INFORMATION: Synthetic construct

<400> SEQUENCE: 36

Lys Leu Ala Leu Lys Leu Ala Leu Lys Leu Ala Leu Ala Leu Lys Leu
1               5                   10                  15

Ala

<210> SEQ ID NO 37
<211> LENGTH: 27
<212> TYPE: PRT
<213> ORGANISM: Artificial Sequence
<220> FEATURE:
<223> OTHER INFORMATION: Synthetic construct

<400> SEQUENCE: 37

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 38
<211> LENGTH: 27
<212> TYPE: PRT
<213> ORGANISM: Artificial Sequence
<220> FEATURE:
<223> OTHER INFORMATION: Synthetic construct

<400> SEQUENCE: 38

```
Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25
```

<210> SEQ ID NO 39
<211> LENGTH: 27
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = N-acetyl-glycine
<220> FEATURE:
<221> NAME/KEY: MISC_FEATURE
<222> LOCATION: (27)..(27)
<223> OTHER INFORMATION: Xaa = Valine amide

<400> SEQUENCE: 39

```
Xaa Ala Leu Phe Leu Gly Phe Leu Gly Ala Ala Gly Ser Thr Met Gly
1               5                   10                  15

Ala Trp Ser Gln Pro Lys Lys Lys Arg Lys Xaa
            20                  25
```

<210> SEQ ID NO 40
<211> LENGTH: 27
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = N-acetyl-glycine
<220> FEATURE:
<221> NAME/KEY: MISC_FEATURE
<222> LOCATION: (27)..(27)
<223> OTHER INFORMATION: Xaa = Valine amide

<400> SEQUENCE: 40

```
Xaa Ala Leu Phe Leu Gly Phe Leu Gly Ala Ala Gly Ser Thr Met Gly
1               5                   10                  15

Ala Trp Ser Gln Pro Lys Ser Lys Arg Lys Xaa
            20                  25
```

<210> SEQ ID NO 41
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = N-acetyl-lysine
<220> FEATURE:
<221> NAME/KEY: MISC_FEATURE
<222> LOCATION: (21)..(21)
<223> OTHER INFORMATION: Xaa = Valine amide

<400> SEQUENCE: 41

```
Xaa Glu Thr Trp Phe Glu Thr Trp Phe Thr Glu Trp Ser Gln Pro Lys
1               5                   10                  15

Lys Lys Arg Lys Xaa
            20
```

<210> SEQ ID NO 42
<211> LENGTH: 140
<212> TYPE: DNA
<213> ORGANISM: Homo sapiens

<400> SEQUENCE: 42
gaggatttca tctcttgtat atgatgatct ggatccacca agacttgttt tatgctcagg      60
gtcaatttct ttttctttt tttttttt tttctttt ctttgagact gggtctcgct         120
ttgttgccca ggctggagtg                                                140

<210> SEQ ID NO 43
<211> LENGTH: 8
<212> TYPE: PRT
<213> ORGANISM: Artificial Sequence
<220> FEATURE:
<223> OTHER INFORMATION: Synthetic construct

<400> SEQUENCE: 43

Tyr Pro Trp Ala Ala Ser Pro Ala
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic construct

<400> SEQUENCE: 44

Tyr Pro Tyr Ala Ala Asp Pro Ala
1               5

<210> SEQ ID NO 45
<211> LENGTH: 14
<212> TYPE: DNA
<213> ORGANISM: Artificial Sequence
<220> FEATURE:
<223> OTHER INFORMATION: Synthetic construct

<400> SEQUENCE: 45
aaagaaaaaa gaaa                                                      14

<210> SEQ ID NO 46
<211> LENGTH: 14
<212> TYPE: RNA
<213> ORGANISM: Artificial Sequence
<220> FEATURE:
<223> OTHER INFORMATION: Synthetic construct

<400> SEQUENCE: 46
uuuguuuuuu guuu                                                      14

<210> SEQ ID NO 47
<211> LENGTH: 11
<212> TYPE: DNA
<213> ORGANISM: Artificial Sequence
<220> FEATURE:
<223> OTHER INFORMATION: Synthetic construct

<400> SEQUENCE: 47
aaaaagaaaa a                                                         11

<210> SEQ ID NO 48
<211> LENGTH: 11
<212> TYPE: RNA

```
<213> ORGANISM: Artificial Sequence
<220> FEATURE:
<223> OTHER INFORMATION: Synthetic construct

<400> SEQUENCE: 48
uuuuuguuuu u                                                              11

<210> SEQ ID NO 49
<211> LENGTH: 15
<212> TYPE: RNA
<213> ORGANISM: Artificial Sequence
<220> FEATURE:
<223> OTHER INFORMATION: Synthetic construct

<400> SEQUENCE: 49
uuuuuuguuu uuuuu                                                          15

<210> SEQ ID NO 50
<211> LENGTH: 24
<212> TYPE: PRT
<213> ORGANISM: Artificial Sequence
<220> FEATURE:
<223> OTHER INFORMATION: Synthetic construct

<400> SEQUENCE: 50

Arg Gln Ile Lys Ile Trp Phe Gln Asn Arg Arg Met Lys Trp Lys Lys
1               5                   10                  15

Tyr Pro Tyr Ala Ala Ser Pro Ala
            20

<210> SEQ ID NO 51
<211> LENGTH: 24
<212> TYPE: PRT
<213> ORGANISM: Artificial Sequence
<220> FEATURE:
<223> OTHER INFORMATION: Synthetic construct

<400> SEQUENCE: 51

Arg Gln Ile Lys Ile Trp Phe Gln Asn Arg Arg Met Lys Trp Lys Lys
1               5                   10                  15

Tyr Pro Tyr Ala Ala Lys Pro Ala
            20

<210> SEQ ID NO 52
<211> LENGTH: 8
<212> TYPE: PRT
<213> ORGANISM: Artificial Sequence
<220> FEATURE:
<223> OTHER INFORMATION: Synthetic construct

<400> SEQUENCE: 52

Tyr Pro Tyr Ala Ala Lys Pro Ala
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic construct

<400> SEQUENCE: 53

Tyr Pro Tyr Ala Ala Arg Pro Ala
1               5
```

```
<210> SEQ ID NO 54
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa = any amino acid

<400> SEQUENCE: 54

Tyr Pro Tyr Ala Ala Xaa Pro Ala
1               5

<210> SEQ ID NO 55
<211> LENGTH: 24
<212> TYPE: PRT
<213> ORGANISM: Artificial Sequence
<220> FEATURE:
<223> OTHER INFORMATION: Synthetic construct

<400> SEQUENCE: 55

Arg Gln Ile Lys Ile Trp Phe Gln Asn Arg Arg Met Lys Trp Lys Lys
1               5                   10                  15

Tyr Pro Tyr Ala Ala Arg Pro Ala
            20

<210> SEQ ID NO 56
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = D-cysteine
<220> FEATURE:
<221> NAME/KEY: MISC_FEATURE
<222> LOCATION: (10)..(10)
<223> OTHER INFORMATION: Xaa = D-cysteine

<400> SEQUENCE: 56

Xaa Tyr Pro Tyr Ala Ala Lys Pro Ala Xaa
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = D-cysteine
<220> FEATURE:
<221> NAME/KEY: MISC_FEATURE
<222> LOCATION: (10)..(10)
<223> OTHER INFORMATION: Xaa = D-cysteine

<400> SEQUENCE: 57

Xaa Tyr Pro Tyr Ala Ala Arg Pro Ala Xaa
1               5                   10

<210> SEQ ID NO 58
<211> LENGTH: 10
<212> TYPE: PRT
<213> ORGANISM: Artificial Sequence
```

```
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = D-cysteine
<220> FEATURE:
<221> NAME/KEY: MISC_FEATURE
<222> LOCATION: (7)..(7)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = D-cysteine

<400> SEQUENCE: 58

Xaa Tyr Pro Tyr Ala Ala Xaa Pro Ala Xaa
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (9)..(9)
<223> OTHER INFORMATION: Xaa = D-glutamic acid

<400> SEQUENCE: 59

Tyr Pro Tyr Ala Ala Lys Pro Ala Xaa
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (9)..(9)
<223> OTHER INFORMATION: Xaa = D-glutamic acid

<400> SEQUENCE: 60

Tyr Pro Tyr Ala Ala Arg Pro Ala Xaa
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (9)..(9)
<223> OTHER INFORMATION: Xaa = D-glutamic acid

<400> SEQUENCE: 61

Tyr Pro Tyr Ala Ala Xaa Pro Ala Xaa
1               5

<210> SEQ ID NO 62
<211> LENGTH: 10
<212> TYPE: PRT
```

```
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = D-lysine
<220> FEATURE:
<221> NAME/KEY: MISC_FEATURE
<222> LOCATION: (10)..(10)
<223> OTHER INFORMATION: Xaa = D-glutamic acid

<400> SEQUENCE: 62

Xaa Tyr Pro Tyr Ala Ala Lys Pro Ala Xaa
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = D-lysine
<220> FEATURE:
<221> NAME/KEY: MISC_FEATURE
<222> LOCATION: (10)..(10)
<223> OTHER INFORMATION: Xaa = D-glutamic acid

<400> SEQUENCE: 63

Xaa Tyr Pro Tyr Ala Ala Arg Pro Ala Xaa
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = D-lysine
<220> FEATURE:
<221> NAME/KEY: MISC_FEATURE
<222> LOCATION: (7)..(7)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = D-glutamic acid

<400> SEQUENCE: 64

Xaa Tyr Pro Tyr Ala Ala Xaa Pro Ala Xaa
1               5                   10

<210> SEQ ID NO 65
<211> LENGTH: 24
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (22)..(22)
<223> OTHER INFORMATION: Xaa = any amino acid
```

```
<400> SEQUENCE: 65

Arg Gln Ile Lys Ile Trp Phe Gln Asn Arg Arg Met Lys Trp Lys Lys
1               5                   10                  15

Tyr Pro Tyr Ala Ala Xaa Pro Ala
            20
```

MODULATION OF P53 FOR THE TREATMENT OF CANCER

CROSS-REFERENCE TO RELATED APPLICATIONS

This application is a continuation of International Patent Application No. PCT/US2017/063537, filed Nov. 29, 2017, which claims priority to U.S. Provisional Application No. 62/427,517 filed Nov. 29, 2016, the disclosures of which are herein incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. CA076069 awarded by the National Institutes of Health. The Government has certain rights in this invention.

REFERENCE TO A "SEQUENCE LISTING"

The Sequence Listing written in file SequenceListing_070772-22411US-1141255.txt created on May 23, 2019, 24,348 bytes, machine format IBM-PC, MS-Windows operating system, is hereby incorporated by reference in its entirety for all purposes.

BACKGROUND OF THE INVENTION

Cancer, of which there are more than 100 different types, poses a very large and grave public health problem. In the United States alone, greater than about 1.6 million new cases of cancer are diagnosed each year, and over 500,000 people die each year from cancer.

In many cancers (i.e., greater than 50% of human cancers), there are disruptions and/or inactivation events in the p53 pathway. p53 is a transcription factor that plays essential roles in normal cell growth, development, and senescence, as well as conserving the overall integrity of the genome and aiding in the prevention of cancer development. Under normal conditions, p53 is highly regulated and protein expression is maintained at low levels. However, in reaction to stress stimuli, p53 is activated and functions as a robust transcription factor that induces the activation of downstream targets that function in DNA repair, cell-cycle arrest, and apoptosis. The importance of strict p53 protein regulation is evidenced by the fact that too much p53 leads to premature ageing and cell death due to excessive apoptosis, whereas too little p53 has been shown to be a key aspect of tumorigenesis. Inactivation or disruption of the p53 pathway can result from, for example, loss of function mutations, gene deletions, or epigenetic alterations, all of which can occur during tumor progression. Examples of cancers which have been demonstrated to have a low p53 mutation status include prostate adenocarcinoma, thyroid carcinoma, neuroblastoma, mesothelioma, and chronic lymphocytic leukemia. Given the cellular roles of p53 and the fact that an increase in p53 has been shown to lead to cancer cell death, restoring p53 wild type function or inducing p53 activity is an attractive therapeutic approach for many cancers.

Administration of chemotherapeutic agents is a common strategy for the treatment of a large number of cancers. These agents work via several different mechanisms, many of which involve targeting cellular processes that are necessary for maintaining genomic stability and/or normal progression through the cell cycle. In some cases, chemotherapeutic agents induce p53 activity. However, the cytotoxic effects produced by chemotherapeutic agents result in profound and often dangerous side effects. Accordingly, there is a need for new therapeutic agents for the prevention and treatment of cancer that can replace current chemotherapeutic agents or reduce the required dosages of chemotherapeutic agents. In particular, there is a need for new agents that restore or induce p53 activity and that of downstream targets. The present invention satisfies these needs, and provides related advantages as well.

BRIEF SUMMARY OF THE INVENTION

In a first aspect, the invention provides an isolated peptide. In some embodiments, the peptide comprises the amino acid sequence set forth in SEQ ID NO:1, 2, 3, 4, 52, 53, or 54. In other embodiments, the peptide further comprises a D-lysine residue at the N-terminus and/or C-terminus. In some other embodiments, the peptide further comprises a D-glutamic acid residue at the N-terminus and/or C-terminus. In still other embodiments, the peptide further comprises a D-cysteine residue at the N-terminus and/or C-terminus. In some embodiments, the peptide is cyclized. In some other embodiments, the peptide is about 5 to 100 amino acids in length. In some instances, the peptide is about 5 to 50 amino acids in length.

In a second aspect, the invention provides a conjugate. In some embodiments, the conjugate comprises a peptide of the present invention and a cell-penetrating peptide (CPP). In particular embodiments, the peptide and the CPP are covalently linked. In other embodiments, the peptide and the CPP are non-covalently associated. In some instances, the CPP is selected from the group consisting of PEP1, Penetratin™, and a combination thereof.

In a third aspect, the invention provides a composition. In some embodiments, the composition comprises a peptide of the present invention or a plurality thereof, a conjugate of the present invention or a plurality thereof, or a combination thereof. In particular embodiments, the peptide is present in the composition at a concentration of about 20 to about 400 nM. In some embodiments, the composition further comprises a chemotherapeutic agent. In particular embodiments, the chemotherapeutic agent is a topoisomerase inhibitor. In some instances, the topoisomerase inhibitor is selected from the group consisting of a topoisomerase I inhibitor, a topoisomerase II inhibitor, and a combination thereof. In certain instances, the topoisomerase inhibitor is selected from the group consisting of doxorubicin, etoposide, teniposide, daunorubicin, mitoxantrone, amsacrine, an ellipticine, aurintricarboxylic acid, HU-331, irinotecan, topotecan, camptothecin, lamellarin D, resveratrol, genistein, quercetin, epigallocatechin gallate, and a combination thereof. In some embodiments, the peptide or plurality thereof, conjugate or plurality thereof, and/or the chemotherapeutic agent are encapsulated by one or more liposomes. In another aspect, the invention provides a peptide-based pharmaceutical composition comprising a composition of the present invention and a pharmaceutically acceptable carrier.

In another aspect, the invention provides an isolated oligonucleotide. In some embodiments, the isolated oligonucleotide comprises the nucleotide sequence set forth in SEQ ID NO:16, 17, 18, 19, 20, 21, 45, 46, 47, 48, or 49. In particular embodiments, the oligonucleotide is about 10 to 100 nucleotides in length. In some instances, the oligonucleotide is about 10 to 40 nucleotides in length. In still another aspect, the invention provides an oligonucleotide-based pharmaceutical composition comprising an isolated nucleotide of the present invention and a pharmaceutically acceptable carrier.

In another aspect, the invention provides a nucleotide construct encoding a peptide of the present invention. In some embodiments, the nucleotide construct comprises a nucleotide sequence encoding a peptide comprising the amino acid sequence set forth in SEQ ID NO:1, 2, 3, 4, 52, 53, or 54. In particular embodiments, the nucleotide construct encodes a peptide that is about 5 to 100 amino acids in length. In some instances, the nucleotide construct encodes a peptide that is about 5 to 50 amino acids in length. In some embodiments, the nucleotide construct further comprises a nucleotide sequence encoding a cell-penetrating peptide (CPP).

In yet another aspect, the invention provides a vector comprising a nucleotide construct of the present invention. In still another aspect, the invention provides a cell comprising one or more vectors of the present invention. In some embodiments, the cell expresses a peptide comprising the amino acid sequence set forth in SEQ ID NO:1, 2, 3, 4, 52, 53, or 54, a conjugate comprising a peptide comprising the amino acid sequence set forth in SEQ ID NO:1, 2, 3, 4, 52, 53, or 54 and a CPP, or a combination thereof. In other embodiments, the cell is first isolated from a subject before the one or more vectors are introduced into the cell. In some instances, the cell is introduced into the subject after the one or more vectors are introduced into the cell.

In another aspect, the invention provides a method for preventing or treating cancer in a subject. In some embodiments, the method comprises administering to the subject a therapeutically effective amount of a peptide-based pharmaceutical composition of the present invention, an oligonucleotide-based pharmaceutical composition of the present invention, a vector of the present invention, a cell of the present invention, or a combination thereof. In some embodiments, the method further comprises delivering radiation therapy to the subject. In some embodiments, the method further comprises administering a chemotherapeutic agent to the subject. In some embodiments, administering the peptide-based pharmaceutical composition, oligonucleotide-based pharmaceutical composition, vector, cell, or combination thereof to the subject enhances the effect of the chemotherapeutic agent. In some embodiments, the chemotherapeutic agent is a type II topoisomerase inhibitor. In some embodiments, the type II topoisomerase inhibitor is selected from the group consisting of doxorubicin, etoposide, and a combination thereof.

In particular embodiments, the subject does not have cancer. In other embodiments, treating the subject results in an improvement in one or more symptoms of cancer. In some embodiments, treating the subject decreases the weight and/or volume of a cancer tumor. In some instances, the weight and/or volume of the cancer tumor is decreased by at least about 50%.

In some embodiments, a test sample is obtained from the subject before and/or after the peptide-based pharmaceutical composition, oligonucleotide-based pharmaceutical composition, vector, cell, or combination thereof is administered to the subject. In some instances, the test sample comprises tissue, blood, or a combination thereof. In particular instances, the test tissue sample comprises cancer tissue.

In some embodiments, the level of one or more biomarkers is determined in the test sample. In some instances, the one or more biomarkers comprises p53 protein. In particular embodiments, the level of the one or more biomarkers in the test sample is compared to the level of the one or more biomarkers in a reference sample. In some instances, the reference sample is normal tissue obtained from the same subject before and/or after the peptide-based pharmaceutical composition, oligonucleotide-based pharmaceutical composition, vector, cell, or combination thereof is administered to the subject. In other instances, the reference sample is obtained from a different subject or a population of subjects. In some instances, the level of p53 protein in the test sample is lower than the level of p53 protein in the reference sample, wherein the test sample is obtained before the peptide-based pharmaceutical composition, oligonucleotide-based pharmaceutical composition, vector, cell, or combination thereof is administered to the subject. In particular instances, administering the peptide-based pharmaceutical composition, oligonucleotide-based pharmaceutical composition, vector, cell, or combination thereof to the subject results in an increase in the level of p53 protein in a test sample obtained from the subject after administration compared to a test sample obtained from the subject before administration.

In yet another aspect, the invention provides a method for enhancing the effect of a chemotherapeutic agent in a subject receiving said chemotherapeutic agent. In some embodiments, the method comprises administering to the subject a therapeutically effective amount of a peptide-based pharmaceutical composition of the present invention, an oligonucleotide-based pharmaceutical composition of the present invention, a vector of the present invention, a cell of the present invention, or a combination thereof. In some embodiments, the subject is being treated for cancer. In some embodiments, the chemotherapeutic agent is a type II topoisomerase inhibitor. In some instances, the type II topoisomerase inhibitor is selected from the group consisting of doxorubicin, etoposide, and a combination thereof.

In still another aspect, the invention provides a method for increasing p53 expression and/or activity in a subject. In some embodiments, the method comprises administering to the subject a therapeutically effective amount of a peptide-based pharmaceutical composition of the present invention, an oligonucleotide-based pharmaceutical composition of the present invention, a vector of the present invention, a cell of the present invention, or a combination thereof. In some embodiments, p53 expression is increased. In some instances, p53 mRNA expression is increased. In other instances, p53 protein expression is increased. In some embodiments, p53 activity is increased. In some embodiments, the association between eIF4E and p53 mRNA is increased.

In other embodiments, the expression and/or activity of a downstream p53 target is increased. In some instances, the downstream p53 target is selected from the group consisting of Puma, p21, and a combination thereof. In some embodiments, the expression and/or activity of p53 in a test sample obtained from the subject after the peptide-based pharmaceutical composition, oligonucleotide-based pharmaceutical composition, vector, cell, or combination thereof has been administered to the subject is increased at least about 1.2-fold compared to a control value. In some embodiments, the control value is measured or determined in a reference sample. In some instances, the reference sample is obtained from the subject before the peptide-based pharmaceutical composition, oligonucleotide-based pharmaceutical composition, vector, cell, or combination thereof is administered to the subject. In other instances, the reference sample is obtained from a subject or population of subjects who are not administered the peptide-based pharmaceutical composition, oligonucleotide-based pharmaceutical composition, vector, cell, or combination thereof.

In another aspect, the invention provides a method for decreasing eIF4E phosphorylation in a subject. In some embodiments, the method comprises administering to the subject a therapeutically effective amount of a peptide-based pharmaceutical composition of the present invention, an oligonucleotide-based pharmaceutical composition of the present invention, a vector of the present invention, a cell of the present invention, or a combination thereof. In some embodiments, the ability of MNK1 and/or MNK2 to phosphorylate eIF4E is decreased. In other embodiments, the phosphorylation of eIF4E at Ser209 is decreased.

In another aspect, the invention provides a kit for preventing or treating cancer in a subject. In some embodiments, the kits comprise a peptide-based pharmaceutical composition of the present invention, an oligonucleotide-based pharmaceutical composition of the present invention, a vector of the present invention, a cell of the present invention, or a combination thereof. In particular embodiments, the kit further comprises instructions for use. In other embodiments, the kit further comprises one or more reagents.

Other objects, features, and advantages of the present invention will be apparent to one of skill in the art from the following detailed description and figures.

BRIEF DESCRIPTION OF THE DRAWINGS

FIG. 1A shows that the addition of RBM38 (SEQ ID NO:2) or eIF4E (SEQ ID NO:3) (300 nM) peptide to MCF7 cells using cell-penetrating peptide PEP1 (SEQ ID NO:13) (20:1 ratio) induced p53 and downstream targets p21 and MDM2. FIG. 1B shows that the addition of RBM38 and eIF4E (375 nM) peptide (in complex with PEP1) to MCF7 cells lead to decreased colony formation. FIG. 1C shows that RBM38, eIF4E and peptide-8 (SEQ ID NO:1) (in complex with PEP1) enhanced the effect of doxorubicin-mediated p53 and p21 upregulation in MCF7 cells. FIG. 1D shows that RBM38, eIF4E, and peptide-8 (in complex with PEP1) enhanced colony formation inhibition of low dose doxorubicin in MCF7 cells. FIG. 1E shows that cyclized peptide-8 (Cyc-8; SEQ ID NO:5) in combination with PEP1 enhanced p53 and downstream target MDM2 in RKO cancer cells. FIG. 1F shows that Penetratin™ fused to eIF4E peptide (Pen-eIF4E; SEQ ID NO:9) enhanced p53 and downstream target MDM2 in RKO cancer cells.

FIG. 5A shows Western blot data illustrating anti-HA, p21, and RBM38 expression, with actin expression as a control. FIG. 5B shows Western blot data illustrating expression of p53, p21, and RBM38, with actin expression as a control.

FIG. 7A shows Western blot data illustrating expression of RBM38, p53, MDM2, and ECT2, with GAPDH expression as a control, in MCF7 (left) and RKO (right) cells. FIG. 7B shows expression of p53 and actin control in RKO cells. FIG. 7C shows expression of p53 and actin control in HCT116 cells.

FIG. 10A shows a schematic representing the RBM38 peptide. FIG. 10B shows a schematic representing the eIF4E peptide.

FIG. 11A shows a schematic of the RBM38 peptide and a binding interface. FIG. 11B shows a schematic of the eIF4E peptide and a binding interface.

FIG. 12A shows a schematic of a portion of the RBM38 peptide that corresponds to SEQ ID NO:2. FIG. 12B shows a schematic of a portion of the eIF4E peptide that corresponds to SEQ ID NO:3.

FIG. 13A shows Western blot data illustrating expression of p53 and actin control in RKO cells. FIG. 13B shows Western blot data illustrating expression of MDM2, p53, p21, and actin control in MCF7 cells. FIG. 13C shows cancer cell colony formation when cells were treated with PEP1 plus control, RBM38, or eIF4E.

FIG. 15A shows a schematic of portions of RBM38 and RBM24 peptides corresponding to SEQ ID NOS:2 and 4, respectively. The two peptides share a common amino acid sequence (underlined). FIG. 15B shows a protein pulldown assay where GST-RBM24 and RBM38 were bound to GST resin. Purified His-eIF4E was then added with the addition of 375 nM of each corresponding peptide. Beads were incubated overnight and then washed extensively before complexes were eluted from the beads using SDS-PAGE lysis buffer followed by Western blot assay. FIG. 15C shows relative eIF4E bound to either RBM24 or RBM38.

FIG. 16A shows Western blot data illustrating expression of p53 and actin control in MCF7 cells treated with 375 nM of the indicated peptides. FIG. 16B shows Western blot data illustrating expression of p53 and actin control in RKO cells treated with 150 nM of the indicated peptides. FIG. 16C shows Western blot data illustrating expression of p53 and actin control in MCF7 cells treated with 50 nM of the indicated peptides. FIG. 16D shows Western blot data illustrating expression of p53 and actin control in MCF7 cells treated with 150 nM of the indicated peptides.

FIGS. 17A-17G show specificity for RBM38. FIG. 17A shows RBM38 and actin control expression data. FIG. 17B shows expression of p53 and actin control in response to treatment with the indicated peptides. FIG. 17C shows expression of p53 and actin control in response to treatment with the indicated peptides in RBM38 knockout. FIG. 17D shows a graph of relative p53 band intensity in response to treatment with the indicated peptides. Data for U2OS cells are shown on the left; data for U2OS RBM38 knockout cells are shown on the right. FIG. 17E shows expression of p53 and actin control in response to treatment with the indicated peptides. FIG. 17F shows expression of p53 and actin control in response to treatment with the indicated peptides in RBM38 knockout. FIG. 17G shows a graph of relative p53 band intensity in response to treatment with the indicated peptides. Data for MCF7 cells are shown on the left; data for MCF7 RBM38 knockout cells are shown on the right.

FIG. 19A shows protein expression data of MDM2, p21, p53, RBM38, and actin control in RKO cells treated with the indicated peptides and 6.25 ng/mL doxorubicin. FIG. 19B shows protein expression data of p21, p53, and actin control in MCF7 cells treated with the indicated peptides and 6.25 ng/mL doxorubicin.

FIG. 20A shows a graph of percent positive cells (for senescence marker sβgal staining) when treated with peptides of the present invention or a combination of peptides and doxorubicin (3.125 ng/mL). FIG. 20B shows a cell colony formation assay wherein MCF7 cells were treated with peptides of the present invention (complexed with PEP1) and doxorubicin (3.125 ng/mL). FIG. 20C shows a cell colony formation assay wherein RKO cells were treated with peptides of the present invention (complexed with PEP1) and doxorubicin (3.125 ng/mL). FIG. 20D shows a cell colony formation assay wherein cells were treated with Pen-Ctrl or Pen-eIF4E, with and without doxorubicin (6.25 ng/mL)

FIG. 23A shows Western blot data when 25 nM of the indicated peptides was used.

FIG. 23B shows Western blot data when 150 nM of the indicated peptides was used. FIG. 23C shows Western blot data when 50 nM of the indicated peptides was used. FIG. 23D shows Western blot data when 375 nM of the indicated peptides was used. FIG. 23E shows Western blot data illustrating p53 and actin control expression when the indicated peptides were administered with vehicle only or 6.25 ng/mL doxorubicin.

FIG. 24A shows tumor sphere assay data. FIG. 24B shows a graph illustrating relative tumor sphere ≥50 μM when peptides of the present invention, either alone or in combination with doxorubicin, were used.

FIG. 27 shows nucleotides sequences highlighting that RBM38 interacts with the p53 3' UTR. Common sequences between exon 11 (SEQ ID NO:42) and oligonucleotide 18T (SEQ ID NO:15) are underlined.

FIG. 28A shows Western blot data illustrating p53 and actin control expression data in response to treatment of RKO cells with the indicated oligonucleotides (5 μM) for 48 hours. FIG. 28B shows Western blot data blot data illustrating p53 and actin control expression data in response to treatment of MCF10A cells with the indicated oligonucleotides (5 μM) for 24 hours. FIG. 28C shows a graph of relative p53 protein levels in response to treatment with the indicated oligonucleotides.

FIG. 29A shows p53 and actin control expression data in response to treatment of MCF7 cells (wild type p53) and MIA-PaCa-2 pancreatic cancer cells (mutant p53 R248W) with indicated oligonucleotides. FIG. 29B shows p53 and actin control expression data in MIA-PaCa-2 cells in response to treatment with the indicated oligonucleotides. FIG. 29C shows p53 and actin control expression data in MIA-PaCa-2 cells in response to treatment with the indicated oligonucleotides. Oligonucleotide sequences were as follows: M3, SEQ ID NO:14; 14A/G, SEQ ID NO:20; 14U/G, SEQ ID NO:49; 15A, SEQ ID NO:21; 6A/G, SEQ ID NO:45; 6U/G, SEQ ID NO:46; 10A/G, SEQ ID NO:47; 10 U/G, SEQ ID NO:48.

FIG. 31A shows data for RKO cells. FIG. 31B shows data for MCF7 cells.

FIG. 32A shows data using RKO cells and a peptide concentration of 50 nM.

FIG. 32B shows data for RKO cells and a peptide concentration of 2.5 μM. FIG. 32C shows data for MCF7 cells and a peptide concentration of 2.5 μM.

FIG. 33A shows the results of an RNA-ChIP assay. FIG. 33B shows the effects on p53 expression in MCF7 wild-type and RBM38 null mutant cells.

FIG. 34A shows the effects on p53 expression in RKO cells, with and without doxorubicin treatment. FIG. 34B shows the effects on p53 expression in MCF7 cells, with and without doxorubicin treatment. FIG. 34C shows MCF7 tumor cell colony formation. FIG. 34D shows RKO tumor cell colony formation. FIG. 34E shows images from a tumor sphere assay. FIG. 34F depicts results of the tumor sphere assay. FIG. 34G shows the effects of peptide/doxorubicin treatment on p53, p21, and RBM38 expression in RKO cells. FIG. 34H shows the effects of peptide/doxorubicin treatment on p53 and p21 expression in MCF7 cells. FIG. 34I shows that peptides of the present invention sensitized tumor cells to low-dose doxorubicin, as well as low-dose etoposide.

FIG. 35A shows images from the mouse xenograft model experiments. FIG. 35B shows the effects on tumor volume. FIG. 35C shows the effects on tumor weight. FIG. 35D shows the effects on p53 and Puma (a downstream target of p53) expression.

FIGS. 36A-36C show the ability of linear and cyclic peptides of the present invention to modulate p53 expression and binding. FIG. 36A shows the results of a binding assay. The binding of peptides #1-4 (SEQ ID NOS:1, 5, 8, and 7, respectively) to His-tagged eIF4E is shown. FIG. 36B shows the effects of cyclic Pep8 (SEQ ID NO:5) on p53 expression at varying concentrations. FIG. 36C shows the results of a tumor sphere assay using cyclic Pep8 (SEQ ID NO:5).

FIG. 37A shows p53 and p-eIF4E expression in RKO cells. FIG. 37B shows p53 and p-eIF4E expression in MCF7 cells. FIG. 37C shows p-eIF4E, eIF4E, and p53 expression in miaPaCa2 cells. FIG. 37D shows the results of colony formation assays using HaCaT and miaPaCa2 cells.

DETAILED DESCRIPTION OF THE INVENTION

I. Introduction

Figure 3:
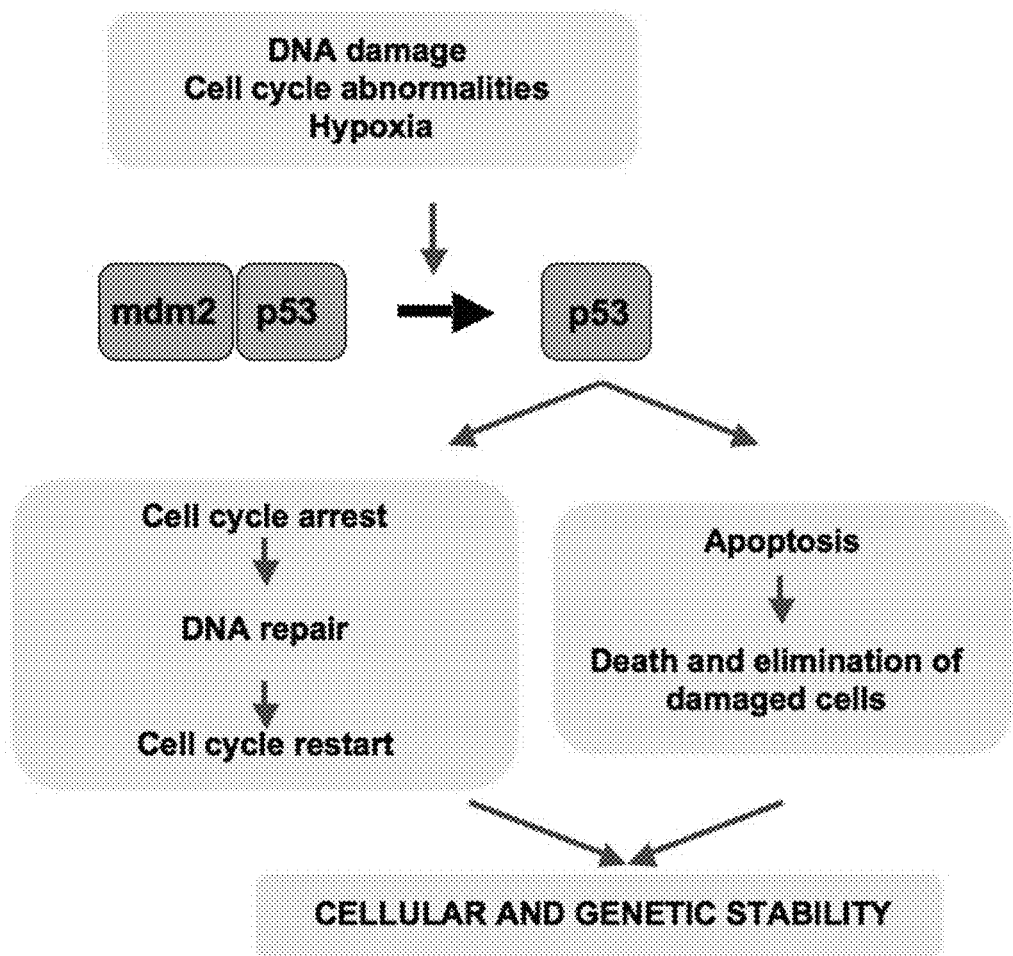
FIG. 3 shows a schematic describing some of the roles that p53 plays.

The p53 tumor suppressor protein plays pivotal roles in maintaining genome integrity and responding to cellular stress, and as such is important in promoting cellular and genetic stability and inhibiting the development of various cancers (FIG. 3). Indeed, inactivation of the p53 pathway is found in more than 50% of human cancers.

Figure 5A:
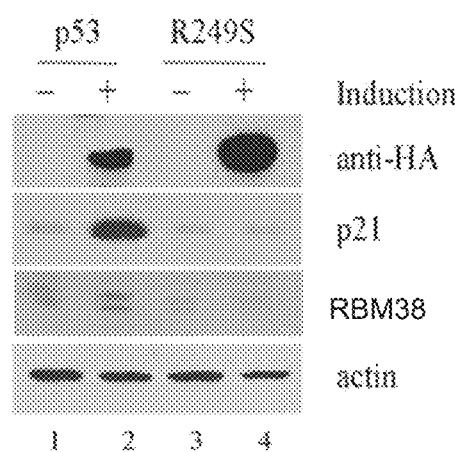
FIGS. 5A and 5B show that RBM38 is a transcriptional target of p53. Figures from Shu et al. *Genes & Dev.* 20:2961-2972 (2006).
Figure 5B:
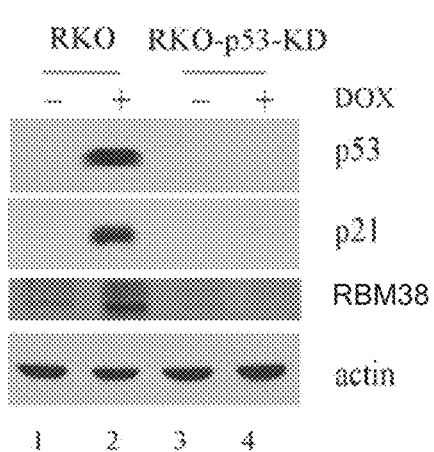
Figure 6:
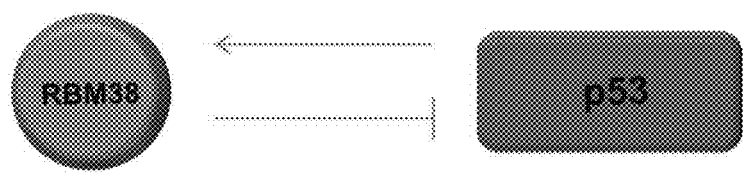
FIG. 6 shows a schematic of the interactions between RBM38 and p53.
Figure 7A:
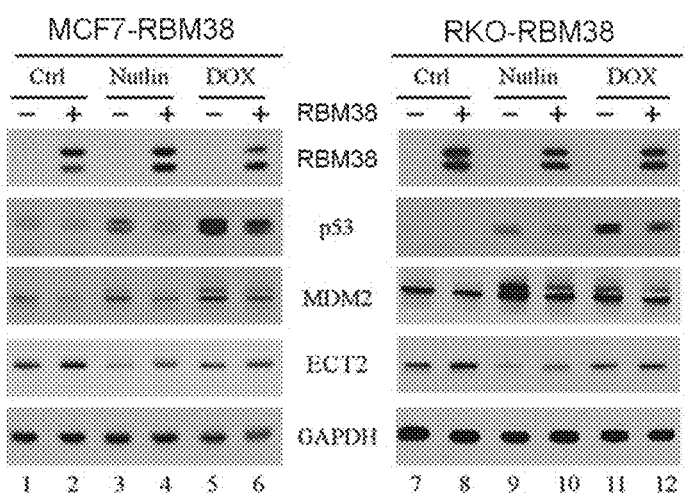
FIGS. 7A-7C show that RBM38 blocks p53 translation. Figures from Zhang et al. *Genes & Dev.* 25:1528-1543 (2011).
Figure 7B:
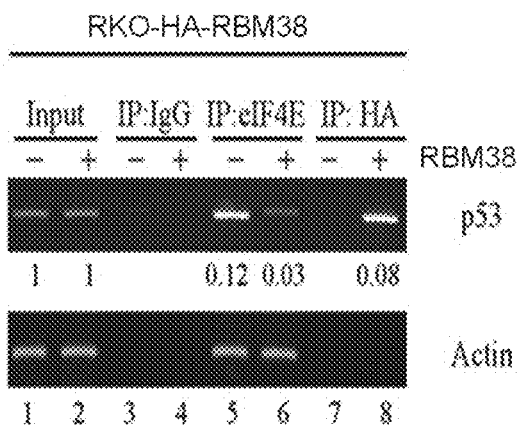
Figure 7C:
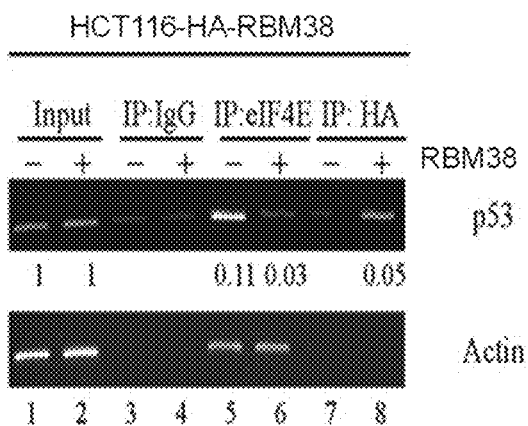
Figure 8:
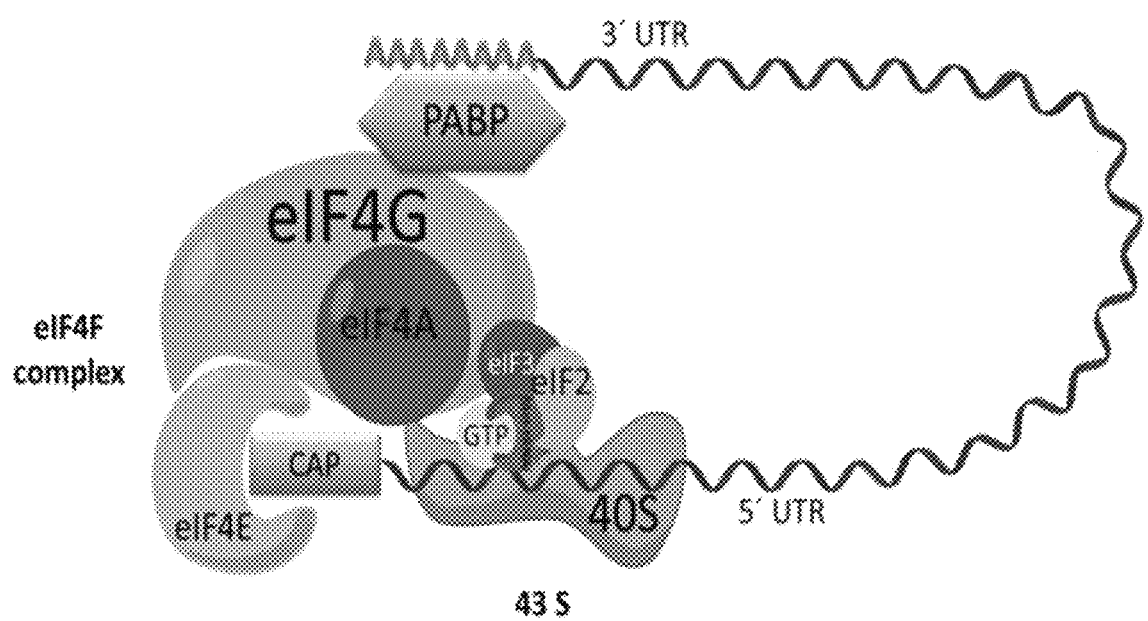
FIG. 8 shows a schematic depicting the eIF4E complex and mRNA translation. Figure from Montero et al. *Viruses* 792:739-750 (2015).

RBM38 (also known as RNA-binding motif protein 38) is an RNA-binding protein that interacts with target mRNA molecules to regulate mRNA stability and hence gene expression. RBM38 increases the mRNA stability of p21, p73, GDF15, and HuR transcripts, but suppresses the stability of p63 and MDM2 transcripts. Also, RBM38 was previously identified as a transcriptional target of the p53 family (FIGS. 5A and 5B; Shu et al. *Genes Dev.* 21:2961-2972 (2006)). In particular, RBM38 can repress p53 translation via interacting with eIF4E, thus preventing eIF4E binding to p53 mRNA (FIGS. 6, 7A-7C, and 8; Zhang et al. *Genes Dev.* 25:1528-1543 (2011); Zhang et al. *Genes Dev.* 27:2246-2258 (2013)). In addition, it has been previously found that the RNA-binding protein RBM24 shares at least some sequence similarity with RBM38 (Jiang et al. JBC 289(6):3164-3175 (2014). RBM38 contains one RNA recognition motif and plays roles in cell cycle control, cell differentiation, and cell senescence.

Figure 4:
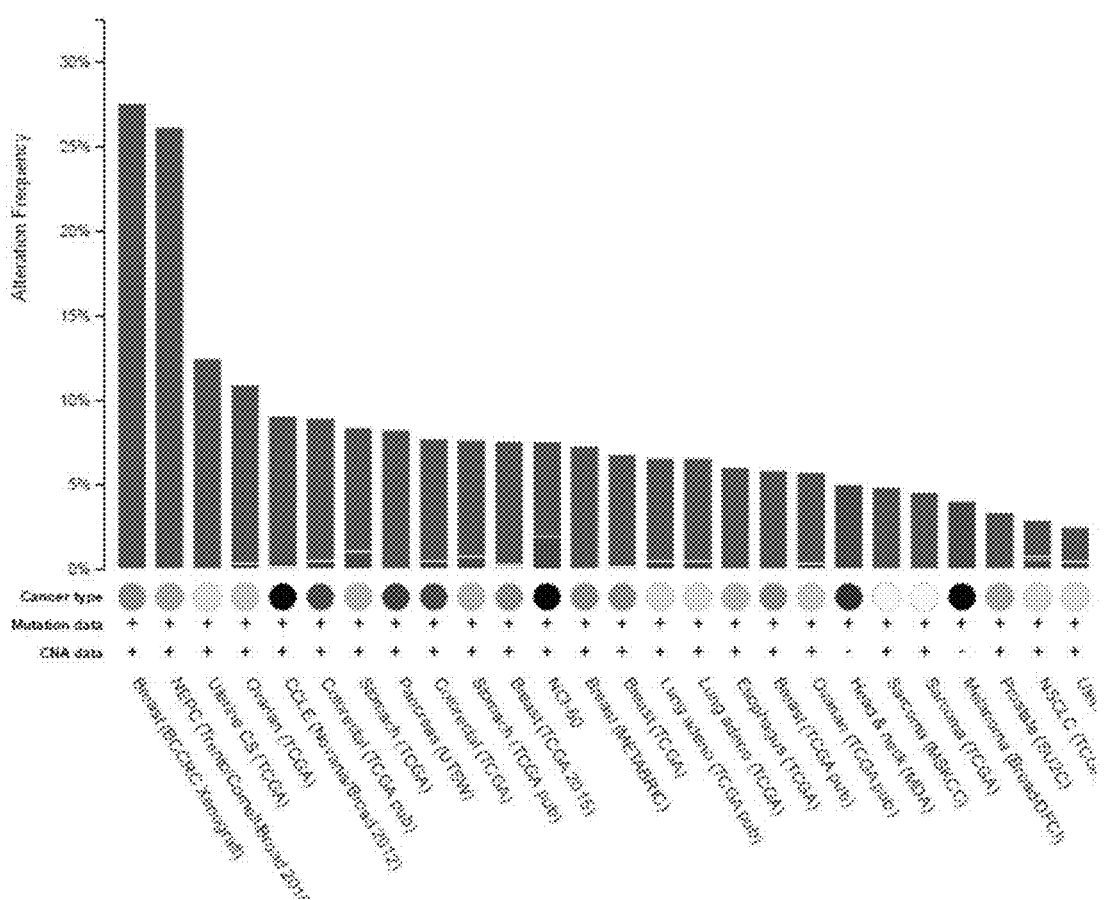
FIG. 4 shows data illustrating the degree of RBM38 amplification in many cancers. Figure from Gao et al. *Sci. Signal* 6, p 11 (2013).

In addition, altered RBM38 expression is found in many types of cancers (FIG. 4). Of note, RBM38 overexpression has been found in breast cancer patients and has been associated with poor prognosis. In addition, RBM38 overexpression is associated with the malignant transformation of colorectal adenoma to carcinoma.

The present invention is based, in part, on the design of peptides and oligonucleotides that disrupt the interaction between RBM38 and eIF4E, and that said peptides and oligonucleotides increase p53 translation and protein expression. In addition to inducing p53, the peptides, oligonucleotides, and other compositions of the present invention can also induce downstream targets in the p53 pathway. Furthermore, the invention is also based, in part, on the surprising discovery that compositions of the present invention exhibit synergistic effects when used in combination with chemotherapeutic agents. Thus, the compositions of the present invention are useful for, among other things, the prevention and treatment of cancer. In addition, the compositions of the present invention are useful for enhancing the effects of chemotherapeutic agents in the prevention and treatment of cancer.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The terms "subject," "individual," and "patient" are used interchangeably herein to refer to a vertebrate, preferably a mammal, more preferably a human. Mammals include, but are not limited to, murines, rats, simians, humans, farm animals, sport animals, and pets. Tissues, cells and their progeny of a biological entity obtained in vivo or cultured in vitro are also encompassed.

As used herein, the term "administering" includes oral administration, topical contact, administration as a suppository, intravenous, intraperitoneal, intramuscular, intralesional, intratumoral, intrathecal, intranasal, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The term "treating" refers to an approach for obtaining beneficial or desired results including, but not limited to, a therapeutic benefit and/or a prophylactic benefit. By therapeutic benefit is meant any therapeutically relevant improvement in or effect on one or more diseases, conditions, or symptoms under treatment. Therapeutic benefit can also mean to effect a cure of one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "enhancing the effect of an agent" refers to increasing the therapeutic benefit and/or prophylactic benefit of an agent (e.g., a chemotherapeutic agent). The term also includes a synergistic enhancement or increase in the therapeutic and/or prophylactic benefit afforded by an agent (i.e., when the agent is combined with another agent). The term "synergistic" refers to an enhancement or increase in an effect (i.e, of two or more agents) that is greater than the sum of the separate effects (i.e., of the two or more agents).

The terms "effective amount," "therapeutically effective amount," and "sufficient amount" interchangeably refer to the amount of a peptide, oligonucleotide, or other composition that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific amount may vary depending on one or more of: the particular agent chosen, the target cell type, the location of the target cell in the subject, the dosing regimen to be followed, whether it is administered in combination with other compounds, timing of administration, and the physical delivery system in which it is carried.

For the purposes herein an effective amount is determined by such considerations as may be known in the art. The amount must be effective to achieve the desired therapeutic effect in a subject suffering from cancer. The desired therapeutic effect may include, for example, amelioration of undesired symptoms associated with cancer, prevention of the manifestation of such symptoms before they occur, slowing down the progression of symptoms associated with cancer, slowing down or limiting any irreversible damage caused by cancer, lessening the severity of or curing a cancer, or improving the survival rate or providing more rapid recovery from a cancer. Further, in the context of prophylactic treatment the amount may also be effective to prevent the development of cancer.

The effective amount depends, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the molecule (e.g., peptide or oligonucleotide) for its target, its distribution profile within the body, the relationship between a variety of pharmacological parameters (e.g., half-life in the body) and undesired side effects, and other factors such as age and gender, etc.

The term "pharmaceutically acceptable carrier" refers to a substance that aids the administration of an active agent to a cell, an organism, or a subject. "Pharmaceutically acceptable carrier" refers to a carrier or excipient that can be included in the compositions of the invention and that causes no significant adverse toxicological effect on the subject. Non-limiting examples of pharmaceutically acceptable carrier include water, NaCl, normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The carrier may also be substances for providing the formulation with stability, sterility and isotonicity (e.g. antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor etc. In some instances, the carrier is an agent that facilitates the delivery of a peptide or an oligonucleotide to a target cell or tissue. One of skill in the art will recognize that other pharmaceutical carriers are useful in the present invention.

The terms "peptide," "polypeptide," and "protein" are used interchangeably herein to refer to a polymer of amino acid residues, or an assembly of multiple polymers of amino acid residues. The terms apply to amino acid polymers in which one or more amino acid residue is an artificial chemical mimic of a corresponding naturally occurring amino acid, as well as to naturally occurring amino acid polymers and non-naturally occurring amino acid polymer.

The term "amino acid" includes naturally-occurring α-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., hydroxyproline, γ-carboxyglutamate and 0-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an a carbon that is bound to a hydrogen, a carboxyl group, an amino group, but have modified R (i.e., side-chain) groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, 1993).

The term "oligonucleotide," "nucleic acid," "nucleotide," or "polynucleotide" refers to deoxyribonucleic acids (DNA) or ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991), Ohtsuka et al., *J. Biol. Chem.* 260:2605-2608 (1985), and Rossolini et al., *Mol. Cell. Probes* 8:91-98 (1994)). The term nucleic acid is used interchangeably with gene, cDNA, and mRNA encoded by a gene.

The term "nucleotide sequence encoding a peptide" means the segment of DNA involved in producing a peptide chain. The term can include regions preceding and following the coding region (leader and trailer) involved in the transcription/translation of a gene product and the regulation of the transcription/translation, as well as intervening sequences (introns) between individual coding segments (exons).

The term "p53," also known as "tumor protein 53," "TP53," "cellular tumor antigen p53," "phosphoprotein 53," "tumor suppressor p53," "antigen NY-CO-13," and "transformation-related protein 53," refers to any protein or isoform thereof that is encoded by the TP53 gene in humans or a homolog thereof p53 plays several and diverse roles related to anti-cancer functions such as maintenance of genome stability and DNA repair, initiation of apoptosis, regulation of the cell cycle and cell growth, and the senescence response. Non-limiting examples of p53 amino acid sequences in humans are set forth under NCBI Reference Sequence numbers NM_00056.5→NP_000537.2, NM_001119584.1→NP_001119584.1, NM_001126113.2→NP_001119585.1, NM_001126114.2→NP_001119586.1, and NM_001126115.1→NP_001119587.1, The term "p21," also known as "cyclin-dependent kinase inhibitor 1" and "CDK-interacting protein 1," refers to a cyclin-dependent kinase inhibitor that is encoded by the CDKN1A gene in humans. p21 is a downstream target of p53 and is activated in response to DNA damage. In particular, p21 plays a significant role in inducing cell cycle arrest. In addition, cytoplasmic levels of p21 are correlated with metastasis in certain cancers, as well as cancer classification according to the TNM staging system, overall survival, and disease-free survival (i.e., increased p21 levels are associated with advanced TNM staging and decreased overall and disease-free survival). Non-limiting examples of p21 amino acid sequences in humans are set forth under NCBI Reference Sequence numbers NM_000389.4→NP_00380.1, NM_001220777.1→NP_001207706.1, NM_001220778.1→NP_01207707.1, NM_001291549.1→NP_001278478.1, and NM_078467.2→NP_510867.1.

The term "Puma," also known as "p53 upregulated modulator of apoptosis" and "Bcl-2 binding component 3," refers to a pro-apoptotic protein that is a member of the Bcl-2 protein family that is encoded by the BBC3 gene in humans. Puma, the expression of which is upregulated by p53 (i.e., upon p53 activation), interacts with Bcl-2 antiapoptotic proteins, which in turn allows proteins such as Bax and Bak to induce mitochondrial apoptosis signaling. Non-limiting examples of Puma amino acid sequences in humans are set forth under NCBI Reference Sequence numbers NM_001127240.2→NP_001120712.1, NM_001127241.2→NP_001120713.1, NM_001127242.2→NP_001120714.1, and NM_014417.4→NP_055232.1.

The term "mouse double minute 2 homolog" or "MDM2" refers to a protein that is encoded by the MDM2 gene in humans and is a significant negative regulator of p53. MDM2 inhibits p53 transcriptional activation and also acts as an E3 ubiquitin ligase that recognizes the N-terminal trans-activation domain of the p53 protein, ubiquitinating p53 and thus targeting it for degradation. Non-limiting examples of MDM2 amino acid sequences in humans are set forth under NCBI Reference Sequence numbers NM_001145337.2→NP_001138809.1, NM_001145339.2→NP_001138811.1, NM_001145340.2→NP_001138812.1, NM_001278462.1→NP_001265391.1, and NM_002392.5→NP_002383.2.

The term "eukaryotic translation initiation factor 4E" or "eIF4E" refers to a protein encoded by the EIF4E gene in humans that is a component of the eukaryotic translation initiation factor 4F complex, which recognizes the 7-methylguanosine cap structure located at the 5' end of mRNA. Association of eIF4E with the 4F complex is the rate-limiting step in the initiation of translation. Non-limiting examples of eIF4E amino acid sequences in humans are set forth under NCBI Reference Sequence numbers NM_001130678.2→NP_001124150.1, NM_001130679.2→NP_00124151.1, NM_001331017.1→NP_001317946.1, and NM_001968.4→NP_001959.1. The protein is also described under NCBI Accession No. P06730.

The term "MAP kinase-interacting serine/threonine-protein kinase 1," "MKNK1," or "MNK1" refers to a protein kinase encoded by the MKNK1 gene in humans. MNK1 is phosphorylated by MAP kinases, thus activating the protein. MNK1 plays a role in the regulation of protein synthesis via interaction with and phosphorylation of eIF4E at Ser209. Non-limiting examples of MNK1 amino acid sequences in humans are set forth under NCBI Reference Sequence numbers NM_001135553.2→NP_001129025.1, NM_003684.5→NP_003675.2, and NM_198973.3→NP_945324.1.

The term "MAP kinase-interacting serine/threonine-protein kinase 2," "MKNK2," or "MNK2" refers to a protein kinase encoded by the MKNK2 gene in humans. MNK2 is phosphorylated by MAP kinases, thus activating the protein. MNK2 plays a role in the regulation of protein synthesis via interaction with and phosphorylation of eIF4E at Ser209. Non-limiting examples of MNK2 amino acid sequences in humans are set forth under NCBI Reference Sequence numbers NM_017572.3→NP_060042.2, and NM_199054.2→NP_951009.1.

III. Detailed Description of the Embodiments

A. Isolated Peptides and Conjugates

In one aspect, the invention provides an isolated peptide. In some embodiments, the peptide comprises the amino acid sequence set forth in SEQ ID NO:1, 2, 3, 4, 52, 53, or 54. In some embodiments, the peptide comprises the amino acid sequence YPYAAxPA (SEQ ID NO:54), wherein "x" is independently selected and can be any amino acid. In some embodiments, "x" is S, K, or R. In some embodiments, "x" is S (SEQ ID NO:1). In some embodiments, "x" is K (SEQ ID NO:52). In some embodiments, "x" is R (SEQ ID NO:53). In some embodiments, the peptide comprises an amino acid sequence that has at least about 70% (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the sequence set forth in SEQ ID NO:1, 2, 3, 4, 52, 53, or 54.

In some embodiments, the peptide further comprises a lysine residue at the N-terminus and/or C-terminus. The lysine can be L-lysine or D-lysine. In some other embodiments, the peptide further comprises a glutamic acid residue at the N-terminus and/or C-terminus. The glutamic acid can be L-glutamic acid or D-glutamic acid. In still other embodiments, the peptide further comprises a cysteine residue at the N-terminus and/or C-terminus. The cysteine can be L-cysteine or D-cysteine. In some embodiments, the peptide is cyclized. Cyclization of the peptide can be facilitated, for example, by placing D-cysteine residues at both the N-terminus and C-terminus of the peptide. Cyclization can also be facilitated, for example, by placing D-lysine and/or D-glutamic acid residues at one or both ends of the peptide. Other methods of cyclizing peptides are known to one of skill in the art. For non-limiting examples of cyclization techniques, see, e.g., White et al. *Nature Chemistry* 3:509-524 (2011).

In some embodiments, the peptide comprises the amino acid sequence YPYAAxPAe (SEQ ID NO:61), wherein "x" is independently selected and can be any amino acid. In some embodiments, "x" is S, K, or R. In some embodiments, "x" is S (SEQ ID NO:7). In some embodiments, "x" is K (SEQ ID NO:59). In some embodiments, "x" is R (SEQ ID NO:60). In some embodiments, the peptide comprises an amino acid sequence that has at least about 70% (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the sequence set forth in SEQ ID NO:7, 59, 60, or 61.

In some embodiments, the peptide comprises the amino acid sequence kYPYAAxPAe (SEQ ID NO:64), wherein "x" is independently selected and can be any amino acid. In some embodiments, "x" is S, K, or R. In some embodiments, "x" is S (SEQ ID NO:8). In some embodiments, "x" is K (SEQ ID NO:62). In some embodiments, "x" is R (SEQ ID NO:63). In some embodiments, the peptide comprises an amino acid sequence that has at least about 70% (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the sequence set forth in SEQ ID NO:8, 62, 63, or 64.

In some embodiments, the peptide comprises the amino acid sequence cIGYQSHADTATKSGSTTKNRFVVc (SEQ ID NO:6). In some embodiments, the peptide comprises the amino acid sequence cYPYAAxPAc (SEQ ID NO:58), wherein "x" is independently selected and can be any amino acid. In some embodiments, "x" is S, K, or R. In some embodiments, "x" is S (SEQ ID NO:5). In some embodiments, "x" is K (SEQ ID NO:56). In some embodiments, "x" is R (SEQ ID NO:57). In some embodiments, the peptide comprises an amino acid sequence that has at least about 70% (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the sequence set forth in SEQ ID NO:5, 6, 56, 57, or 58.

In some embodiments, the peptide comprises a portion of the human RBM38 (also known as RNPC1, SEB4, and RNA-binding protein 38; NCBI Accession No. Q9HOZ9) amino acid sequence (SEQ ID NO:22). In some instances, the peptide comprises less than 239 contiguous amino acids of the sequence set forth in SEQ ID NO:22. In other instances, the peptide comprises between 200 and 238 (e.g., 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, or 238) contiguous amino acids of the sequence set forth in SEQ ID NO:22. In some other instances, the peptide comprises between about 100 and about 200 (e.g., about 100, 105, 110, 115, 120, 125, 130, 135, 140, 145, 150, 155, 160, 165, 170, 175, 180, 185, 190, 195, or 200) contiguous amino acids of the sequence set forth in SEQ ID NO:22. In yet other instances, the peptide comprises between about 5 and about 100 (e.g., about 5, 10, 15, 20, 25, 30, 35, 40, 45, 50, 55, 60, 65, 70, 75, 80, 85, 90, 95, or 100) contiguous amino acids of the sequence set forth in SEQ ID NO:22. In some instances, the peptide comprises 40 contiguous amino acids of the sequence set forth in SEQ ID NO:22. In other instances, the peptide comprises 8 contiguous amino acids of the sequence set forth in SEQ ID NO:22. In some embodiments, the peptide comprises the amino acid sequence set forth in SEQ ID NO:1. In other embodiments, the peptide comprises the amino acid sequence set forth in SEQ ID NO:2. In other embodiments, the peptide comprises the amino acid sequence set forth in SEQ ID NO:43, 44, 52, 53, or 54. In some embodiments, the peptide comprises an amino acid sequence that has at least about 70% (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the sequence set forth in SEQ ID NO:1, 2, 52, 53, or 54.

In other embodiments, the peptide comprises a portion of the human eIF4E (also known as eukaryotic translation initiation factor 4E; NCBI Accession No. P06730) amino acid sequence (SEQ ID NO:23). In some instances, the peptide comprises less than 217 contiguous amino acids of the sequence set forth in SEQ ID NO:23. In other instances, the peptide comprises between about 200 and about 216 (e.g., about 201, 202, 203, 204, 205, 206, 207, 208, 209, 210, 211, 212, 213, 214, 215, or 216) contiguous acids of the sequence set forth in SEQ ID NO:23. In some other instances, the peptide comprises between about 100 and about 200 (e.g., about 100, 105, 110, 115, 120, 125, 130, 135, 140, 145, 150, 155, 160, 165, 170, 175, 180, 185, 190, 195, or 200) contiguous amino acids of the sequence set forth in SEQ ID NO:23. In yet other instances, the peptide comprises between about 5 and about 100 (e.g., about 5, 10, 15, 20, 25, 30, 35, 40, 45, 50, 55, 60, 65, 70, 75, 80, 85, 90, 95, or 100) contiguous amino acids of the sequence set forth in SEQ ID NO:23. In some instances, the peptide comprises 23 contiguous amino acids of the sequence set forth in SEQ ID NO:23. In some embodiments, the peptide comprises the amino acid sequence set forth in SEQ ID NO:3. In some embodiments, the peptide comprises an amino acid sequence that has at least about 70% (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the sequence set forth in SEQ ID NO:3.

In other embodiments, the peptide comprises a portion of the human RBM24 (also known as RNA-binding protein 24, RNA-binding motif protein 24, and RNA-binding region-containing protein 6; NCBI Accession No. Q9BX46) amino acid sequence (SEQ ID NO:24). In some instances, the peptide comprises less than 236 contiguous amino acids of the sequence set forth in SEQ ID NO:24. In other instances, the peptide comprises between about 200 and about 235 (e.g., about 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, or 235) contiguous acids of the sequence set forth in SEQ ID NO:24. In some other instances, the peptide comprises between about 100 and about 200 (e.g., about 100, 105, 110, 115, 120, 125, 130, 135, 140, 145, 150, 155, 160, 165, 170, 175, 180, 185, 190, 195, or 200) contiguous amino acids of the sequence set forth in SEQ ID NO:24. In yet other instances, the peptide comprises between about 5 and about 100 (e.g., about 5, 10, 15, 20, 25, 30, 35, 40, 45, 50, 55, 60, 65, 70, 75, 80, 85, 90, 95, or 100) contiguous amino acids of the sequence set forth in SEQ ID NO:24. In some instances, the peptide comprises about 25 contiguous amino acids of the sequence set forth in SEQ ID NO:24. In some embodiments, the peptide comprises the amino acid sequence set forth in SEQ ID NO:4. In some embodiments, the peptide comprises an amino acid sequence that has at least about 70% (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the sequence set forth in SEQ ID NO:4.

In some embodiments, the peptide comprises about 8 to about 40 amino acids (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids) of the amino acid sequence set forth in SEQ ID NO:2. In other embodiments, the peptide comprises about 8 to about 20 amino acids (e.g., about 8, 9, 10, 11, 12, 13, 14, 15, 16, 17, 18, 19, or 20 amino acids) of the amino acid sequence set forth in SEQ ID NO:2. In some embodiments, the peptide comprises about 8 to about 25 amino acids (e.g., about 8, 9, 10, 11, 12, 13, 14, 15, 16, 17, 18, 19, 20, 21, 22, 23, 24, or 25 amino acids) of the amino acid sequence set forth in SEQ ID NO:4. In particular embodiments, the peptide comprises about 8 to about 15 amino acids (e.g., about 8, 9, 10, 11, 12, 13, 14, or 15 amino acids) of the amino acid sequence set forth in SEQ ID NO:2 or 4. In some embodiments, the peptide comprises about 8 amino acids of the amino acid sequence set forth in SEQ ID NO:2 or 4. In some instances, the peptide comprises the amino acid sequence set forth in SEQ ID NO:1, 52, 53, or 54.

In some embodiments, the peptide comprises about 8 to about 23 amino acids (e.g., about 8, 9, 10, 11, 12, 13, 14, 15, 16, 17, 18, 19, 20, 21, 22, or 23 amino acids) of the amino acid sequence set forth in SEQ ID NO:3. In other embodiments, the peptide comprises about 8 to about 15 amino acids (e.g., about 8, 9, 10, 11, 12, 13, 14, or 15 amino acids) of the amino acid sequence set forth in SEQ ID NO:3.

In some embodiments, the peptide is at least about 200 amino acids in length. In other embodiments, the peptide is about 100 to about 200 (e.g., about 100, 105, 110, 115, 120, 125, 130, 135, 140, 145, 150, 155, 160, 165, 170, 175, 180, 185, 190, 195, or 200) amino acids in length. In some other embodiments, the peptide is about 5 to about 100 (e.g., about 5, 10, 15, 20, 25, 30, 35, 40, 45, 50, 55, 60, 65, 70, 75, 80, 85, 90, 95, or 100) amino acids in length. In particular embodiments, the peptide is about 5 to about 50 (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) amino acids in length. In some instances, the peptide is about 40 amino acids in length. In other instances, the peptide is about 23 amino acids in length. In some other instances, the peptide is about 25 amino acids in length. In still other instances, the peptide is about 8 amino acids in length.

In a second aspect, the invention provides a conjugate. In some embodiments, the conjugate comprises a peptide of the present invention and a cell-penetrating peptide (CPP). CPPs are short peptides that facilitate cellular intake or uptake of various cargos (including but not limited to nanosize particles, small chemical molecules, and large fragments of DNA). The cargo can be associated with the CPPs either through chemical linkage via covalent bonds or through non-covalent interactions. The function of the CPPs are to deliver the cargo into cells, a process that commonly occurs through endocytosis with the cargo delivered to delivery vectors for use in research and medicine. CPPs typically have an amino acid composition that either contains a high relative abundance of positively charged amino acids such as lysine or arginine, or have sequences that contain an alternating pattern of polar/charged amino acids and non-polar/hydrophobic amino acids. These two types of structures are referred to as polycationic or amphipathic, respectively. Alternatively, CPPs can be hydrophobic peptides, containing only apolar residues, having a low net charge or hydrophobic amino acid groups that are crucial for cellular uptake. CPPs can operate via one or more mechanisms, including but not limited to direct membrane penetration, endocytosis-mediated translocation, and translocation through the formation of a transitory structure.

Suitable hydrophilic CPPs include but are not limited to Penetratin™ (also known as Antennapedia PTD; SEQ ID NO:12), TAT (SEQ ID NO:25), SynB1 (SEQ ID NO:26), SynB3 (SEQ ID NO:27), PTD-4 (SEQ ID NO:28), PTD-5 (SEQ ID NO:29), FHV Coat-(35-49) (SEQ ID NO:30), BMV Gag-(7-25) (SEQ ID NO:31), HTLV-II Rex-(4-16) (SEQ ID NO:32), D-Tat (SEQ ID NO:33), and R9-Tat (SEQ ID NO:34).

Suitable amphiphilic CPPs include but are not limited to Transportan (SEQ ID NO:35), MAP (SEQ ID NO:36), SBP (SEQ ID NO:37), FBP (SEQ ID NO:38), MPG (SEQ ID NO:39), MPG$^{(\Delta NLS)}$ (SEQ ID NO:40), PEP1 (SEQ ID NO:13), PEP2 (SEQ ID NO:41), and PEP3.

Furthermore, any number of polyarginine chimera and polylysine chimera sequences can function as suitable CPPs.

In some embodiments, the conjugate comprises a peptide comprising the amino acid sequence set forth in SEQ ID NO:1, 2, 3, 4, 52, 53, and/or 54. In particular embodiments, the peptide and the CPP are covalently linked. In other embodiments, the peptide and the CPP are non-covalently associated. In some instances, the CPP is selected from the group consisting of PEP1, Penetratin™, and a combination thereof.

In some embodiments, the conjugate comprises the amino acid sequence RQIKIWFQNRRMKWKKIGYQSHAD-TATKSGSTTKNRFVV (SEQ ID NO:9). In some embodiments, the conjugate comprises the amino acid sequence RQIKIWFQNRRMKWKKYPYAAxPA (SEQ ID NO:65), wherein "x" is independently selected and can be any amino acid. In some embodiments, "x" is S, K, or R. In some embodiments, "x" is S (SEQ ID NO:50). In some embodiments, "x" is K (SEQ ID NO:51). In some embodiments, "x" is R (SEQ ID NO:55). In some embodiments, the conjugate comprises an amino acid sequence that has at least about 70% (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the sequence set forth in SEQ ID NO:9, 50 51, 55, or 65.

B. Oligonucleotides

In another aspect, the invention provides an isolated oligonucleotide or a plurality thereof. In some embodiments, the oligonucleotide comprises the nucleotide sequence set forth in SEQ ID NO:16, 17, 18, 19, 20, 21, 45, 46, 47, 48, or 49. In some embodiments, the oligonucleotide is about 10 to about 100 nucleotides (e.g., about 10, 15, 20, 25, 30, 35, 40, 45, 50, 55, 60, 65, 70, 75, 80, 85, 90, 95, or 100 nucleotides) in length. In particular embodiments, the oligonucleotide is about 10 to about 40 nucleotides (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) in length. In some embodiments, the oligonucleotide comprises a nucleotide sequence that has at least about 70% (e.g., about 70%, 75%, 80%, 85%, 86%, 87%, 88%, 89%, 90%, 90%, 91%, 92%, 93%, 94%, 95%, 96%, 97%, 98%, 99%, or 100%) identity to the sequence set forth in SEQ ID NO:16, 17, 18, 19, 20, 21, 45, 46, 47, 48, or 49.

C. Compositions

In another aspect, the invention provides compositions comprising a peptide of the present invention or a plurality thereof and/or a conjugate of the present invention or a plurality thereof. In some embodiments, the compositions include any one of the peptides or conjugates of the present invention. In other embodiments, the compositions include two or more of any of the peptides and/or conjugates of the present invention. For example, the compositions may include 2, 3, 4, 5, 6, 7, 8, 9, 10, 11, 12, 13, 14, 15, 16, 17, 18, 19, 20, 21, 22, 23, 24, 25, or more different peptides and/or conjugates. In some embodiments, the compositions comprise peptides and/or conjugates comprising amino acid sequences that have at least about 70% (e.g., about 70%, 75%, 80%, 85%, 86%, 87%, 88%, 89%, 90%, 90%, 91%, 92%, 93%, 94%, 95%, 96%, 97%, 98%, 99%, or 100%) to the amino acid sequences set forth in SEQ ID NOS:1, 2, 3, 4, 5, 6, 7, 8, 9, 50, 51, 52, 53, 54, 55, 56, 57, 58, 59, 60, 61, 62, 63, 64, or 65, or a combination thereof. In some embodiments, the compositions comprise peptides and/or conjugates comprising amino acid sequences set forth in SEQ ID NOS: 1, 2, 3, 4, 5, 6, 7, 8, 9, 50, 51, 52, 53, 54, 55, 56, 57, 58, 59, 60, 61, 62, 63, 64, or 65, or a combination thereof.

In some embodiments, the concentration of the peptide, conjugate, or plurality thereof in the composition is about 5 to about 100 nM (e.g., about 5 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, or 100 nM). In other embodiments, the concentration of the peptide, conjugate, or plurality thereof in the composition is about 100 to about 1,000 nM (e.g., about 100 nM, 150 nM, 200 nM, 250 nM, 300 nM, 350 nM, 375 nM, 400 nM, 450 nM, 500 nM, 550 nM, 600 nM, 650 nM, 700 nM, 750 nM, 800 nM, 850 nM, 900 nM, 950 nM, or 1,000 nM). In some other embodiments, the concentration of the peptide, conjugate, or plurality thereof in the composition is about 1 to about 100 mM (e.g., about 1 mM, 2 mM, 3 mM, 4 mM, 5 mM, 6 mM, 7 mM, 8 mM, 9 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM). In some instances, the concentration of the peptide, conjugate, or plurality thereof is about 20 to about 400 nM (e.g., about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 nM).

In some other embodiments, the composition comprises about 10 to about 1,000 ng (e.g., about 10 ng, 20 ng, 30 ng, 40 ng, 50 ng, 60 ng, 70 ng, 80 ng, 90 ng, 100 ng, 150 ng, 200 ng, 250 ng, 300 ng, 350 ng, 400 ng, 450 ng, 500 ng, 550 ng, 600 ng, 650 ng, 700 ng, 750 ng, 800 ng, 850 ng, 900 ng, 950 ng, or 1,000 ng) of a CPP or plurality thereof. In other embodiments, the composition comprises about 1 to about 100 µg (e.g., about 1 µg, 2 µg, 3 µg, 4 µg, 5 µg, 6 µg, 7 µg, 8 µg, 9 µg, 10 µg, 11 µg, 12 µg, 13 µg, 14 µg, 15 µg, 16 µg, 17 µg, 18 µg, 19 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, or 100 µg) of a CPP or plurality thereof. In some instances, the composition comprises about 1 to about 10 µg of a CPP. In particular instances, the composition comprises about 6 to about 8 µg of a CPP. In some embodiments, the CPP is selected from the group consisting of PEP1, Penetratin™, and a combination thereof.

In some embodiments, the composition further comprises a chemotherapeutic agent. Chemotherapeutic agents that can be used in the present invention include but are not limited to alkylating agents (e.g., nitrogen mustards (e.g., mechlorethamine, chlorambucil, cyclophosphamide, ifosfamide, melphalan), nitrosoureas (e.g., streptozocin, carmustine (BCNU), lomustine), alkyl sulfonates (e.g., busulfan), triazines (e.g., dacarbazine (DTIC), temozlomide), ethylenimines (e.g., thiotepa, altretamine (hexamethylmelamine))), platinum drugs (e.g., cisplatin, carboplatin, oxalaplatin), antimetabolites (e.g., 5-fluorouracil (5-FU), 6-mercaptopurine (6-MP), capecitabine, cytarabine, floxuridine, fludarabine, gemcitabine, hydroxyurea, methotrexate, pemetrexed), anthracycline anti-tumor antibiotics (e.g., daunorubicin, doxorubicin, epirubicin, idarubicin), non-anthracycline anti-tumor antibiotics (e.g., actinomycin-D, bleomycin, mitomycin-C, mitoxantrone), mitotic inhibitors (e.g., taxanes (e.g., paclitaxel, docetaxel), epothilones (e.g., ixabepilone), vinca alkaloids (e.g., vinblastine, vincristine, vinorelbine), estramustine), corticosteroids (e.g., prednisone, methylprednisolone, dexamethasone), L-asparaginase, bortezomib, and topoisomerase inhibitors.

Topoisomerase inhibitors are compounds that inhibit the activity of topoisomerases, which are enzymes that facilitate changes in DNA structure by catalyzing the breaking and rejoining of phosphodiester bonds in the backbones of DNA strands. Such changes in DNA structure are necessary for DNA replication during the normal cell cycle. Topoisomerase inhibitors inhibit DNA ligation during the cell cycle, leading to an increased number of single- and double-stranded breaks and thus a degradation of genomic stability. Such a degradation of genomic stability leads to apoptosis and cell death.

Topoisomerases are often divided into type I and type II topoisomerases. Type I topoisomerases are essential for the relaxation of DNA supercoiling during DNA replication and transcription. Type I topoisomerases generate DNA single-strand breaks and also religate said breaks to re-establish an intact duplex DNA molecule. Examples of inhibitors of topoisomerase type I include irinotecan, topotecan, camptothecin, and lamellarin D, which all target type IB topoisomerases.

Type II topoisomerase inhibitors are broadly classified as topoisomerase poisons and topoisomerase inhibitors. Topoisomerase poisons target topoisomerase-DNA complexes, while topoisomerase inhibitors disrupt enzyme catalytic turnover. Examples of type II topoisomerase inhibitors include amsacrine, etoposide, etoposide phosphate, teniposide, doxorubicin, and fluoroquinolones.

In some embodiments, the chemotherapeutic agent is a topoisomerase inhibitor. In some instances, the topoisomerase inhibitor is a topoisomerase I inhibitor, a topoisomerase II inhibitor, or a combination thereof. In particular embodiments, the topoisomerase inhibitor is selected from the group consisting of doxorubicin, etoposide, teniposide, daunorubicin, mitoxantrone, amsacrine, an ellipticine, aurintricarboxylic acid, HU-331, irinotecan, topotecan, camptothecin, lamellarin D, resveratrol, genistein, quercetin, epigallocatechin gallate (EGCG), and a combination thereof. EGCG is one example of a plant-derived natural phenol that serves as a suitable topoisomerase inhibitor. In some instances, the topoisomerase inhibitor is doxorubicin.

In some embodiments, the concentration of the chemotherapeutic agent in the composition is about 0.1 ng/mL to about 1 ng/mL (e.g., about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 ng/mL). In some embodiments, the concentration of the chemotherapeutic agent in the composition is about 1 ng/mL to about 10 ng/mL (e.g., about 1 ng/mL, 1.5 ng/mL, 2 ng/mL, 2.5 ng/mL, 3 ng/mL, 3.5 ng/mL, 4 ng/mL, 4.5 ng/mL, 5 ng/mL, 5.5 ng/mL, 6 ng/mL, 6.5 ng/mL, 7 ng/mL, 7.5 ng/mL, 8 ng/mL, 8.5 ng/mL, 9 ng/mL, 9.5 ng/mL, or 10 ng/mL). In some other embodiments, the concentration is about 3 ng/mL to about 6 ng/mL (e.g., about 3 ng/mL, 3.5 ng/mL, 4 ng/mL, 4.5 ng/mL, 5 ng/mL, 5.5 ng/mL, or 6 ng/mL). In other embodiments, the concentration of the chemotherapeutic agent in the composition is about 10 ng/mL to 1,000 ng/mL (e.g., about 10 ng/mL, 11 ng/mL, 12 ng/mL, 13 ng/mL, 14 ng/mL, 15 ng/mL, 16 ng/mL, 17 ng/mL, 18 ng/mL, 19 ng/mL, 20 ng/mL, 25 ng/mL, 30 ng/mL, 35 ng/mL, 40 ng/mL, 45 ng/mL, 50 ng/mL, 55 ng/mL, 60 ng/mL, 65 ng/mL, 70 ng/mL, 75 ng/mL, 80 ng/mL, 85 ng/mL, 90 ng/mL, 95 ng/mL, 100 ng/mL, 110 ng/mL, 120 ng/mL, 130 ng/mL, 140 ng/mL, 150 ng/mL, 160 ng/mL, 170 ng/mL, 180 ng/mL, 190 ng/mL, 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, or 1,000 ng/mL).

In some other embodiments, the peptide or plurality thereof, conjugate or plurality thereof, and/or chemotherapeutic agent are encapsulated by one or more liposomes. Liposomes are spherical vessels comprising at least one lipid bilayer, and are often composed of phospholipids (commonly phoshatidylcholine, although any other lipid is suitable, as long as it is compatible with the lipid bilayer structure). Suitable liposomes include multilamellar vesicles small unilamellar vesicles, large unilamellar vesicles, and cochleate vesicles. Methods of preparing liposomes and loading cargos into liposomes will be known to one of skill in the art.

In another aspect, the invention provides a nucleotide construct encoding a peptide and/or a conjugate of the present invention. In some embodiments, the nucleotide construct encodes a peptide that comprises a portion of the human RBM38 (also known as RNPC1, SEB4, and RNA-binding protein 38; NCBI Accession No. Q9HOZ9) amino acid sequence (SEQ ID NO:22). In some instances, the nucleotide construct encodes a peptide that comprises less than 239 contiguous amino acids of the sequence set forth in SEQ ID NO:22. In other instances, the nucleotide construct encodes a peptide that comprises between about 200 and about 238 (e.g., about 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, or 238) contiguous amino acids of the sequence set forth in SEQ ID NO:22. In some other instances, the nucleotide construct encodes a peptide that comprises between about 100 and about 200 (e.g., about 100, 105, 110, 115, 120, 125, 130, 135, 140, 145, 150, 155, 160, 165, 170, 175, 180, 185, 190, 195, or 200) contiguous amino acids of the sequence set forth in SEQ ID NO:22. In yet other instances, the nucleotide construct encodes a peptide that comprises between about 5 and about 100 (e.g., about 5, 10, 15, 20, 25, 30, 35, 40, 45, 50, 55, 60, 65, 70, 75, 80, 85, 90, 95, or 100) contiguous amino acids of the sequence set forth in SEQ ID NO:22. In some instances, the nucleotide construct encodes a peptide that comprises 40 contiguous amino acids of the sequence set forth in SEQ ID NO:22. In other instances, the nucleotide construct encodes a peptide that comprises 8 contiguous amino acids of the sequence set forth in SEQ ID NO:22. In some embodiments, the nucleotide construct encodes a peptide that comprises the amino acid sequence set forth in SEQ ID NO:1. In other embodiments, the nucleotide construct encodes a peptide that comprises the amino acid sequence set forth in SEQ ID NO:2. In some embodiments, the nucleotide construct encodes a peptide that comprises an amino acid sequence that has at least about 70% (e.g., about 70%, 75%, 80%, 85%, 86%, 87%, 88%, 89%, 90%, 90%, 91%, 92%, 93%, 94%, 95%, 96%, 97%, 98%, 99%, or 100%) identity to the sequence set forth in SEQ ID NO:1 or 2.

In some embodiments, the nucleotide construct encodes a peptide that comprises an amino acid sequence that has at least about 70% (e.g., about 70%, 75%, 80%, 85%, 86%, 87%, 88%, 89%, 90%, 90%, 91%, 92%, 93%, 94%, 95%, 96%, 97%, 98%, 99%, or 100%) identity to the sequence set forth in SEQ ID NO:1, 2, 3, 4, 5, 6, 7, 8, 52, 53, 54, 56, 57, 58, 59, 60, 61, 62, 63, or 64. In some embodiments, the nucleotide construct encodes a peptide that comprises an amino acid set forth in SEQ ID NO: 1, 2, 3, 4, 5, 6, 7, 8, 52, 53, 54, 56, 57, 58, 59, 60, 61, 62, 63, or 64.

In other embodiments, the nucleotide construct encodes a peptide that comprises a portion of the human eIF4E (also known as eukaryotic translation initiation factor 4E; NCBI Accession No. P06730) amino acid sequence (SEQ ID NO:23). In some instances, the nucleotide construct encodes a peptide that comprises less than about 217 contiguous amino acids of the sequence set forth in SEQ ID NO:23. In other instances, the nucleotide construct encodes a peptide that comprises between about 200 and about 216 (e.g., about 201, 202, 203, 204, 205, 206, 207, 208, 209, 210, 211, 212, 213, 214, 215, or 216) contiguous amino acids of the sequence set forth in SEQ ID NO:23. In some other instances, the nucleotide construct encodes a peptide that comprises between about 100 and about 200 (e.g., about 100, 105, 110, 115, 120, 125, 130, 135, 140, 145, 150, 155, 160, 165, 170, 175, 180, 185, 190, 195, or 200) contiguous amino acids of the sequence set forth in SEQ ID NO:23. In yet other instances, the nucleotide construct encodes a peptide that comprises between about 5 and about 100 (e.g., about 5, 10, 15, 20, 25, 30, 35, 40, 45, 50, 55, 60, 65, 70, 75, 80, 85, 90, 95, or 100) contiguous amino acids of the sequence set forth in SEQ ID NO:23. In some instances, the nucleotide construct encodes a peptide that comprises about 23 contiguous amino acids of the sequence set forth in SEQ ID NO:23. In some embodiments, the nucleotide construct encodes a peptide that comprises the amino acid sequence set forth in SEQ ID NO:3. In some embodiments, the nucleotide construct encodes a peptide that comprises an amino acid sequence that has at least about 70% (e.g., about 70%, 75%, 80%, 85%, 86%, 87%, 88%, 89%, 90%, 90%, 91%, 92%, 93%, 94%, 95%, 96%, 97%, 98%, 99%, or 100%) identity to the sequence set forth in SEQ ID NO:3.

In other embodiments, the nucleotide construct encodes a peptide that comprises a portion of the human RBM24 (also known as RNA-binding protein 24, RNA-binding motif protein 24, and RNA-binding region-containing protein 6; NCBI Accession No. Q9BX46) amino acid sequence (SEQ ID NO:24). In some instances, the nucleotide construct encodes a peptide that comprises less than 236 contiguous amino acids of the sequence set forth in SEQ ID NO:24. In other instances, the nucleotide construct encodes a peptide that comprises between 200 and 235 (e.g., 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, or 235) contiguous amino acids of the sequence set forth in SEQ ID NO:24. In some other instances, the nucleotide construct encodes a peptide that comprises between about 100 and about 200 (e.g., about 100, 105, 110, 115, 120, 125, 130, 135, 140, 145, 150, 155, 160, 165, 170, 175, 180, 185, 190, 195, or 200) contiguous amino acids of the sequence set forth in SEQ ID NO:24. In yet other instances, the nucleotide construct encodes a peptide that comprises between about 5 and about 100 (e.g., about 5, 10, 15, 20, 25, 30, 35, 40, 45, 50, 55, 60, 65, 70, 75, 80, 85, 90, 95, or 100) contiguous amino acids of the sequence set forth in SEQ ID NO:24. In some instances, the nucleotide construct encodes a peptide that comprises about 25 contiguous amino acids of the sequence set forth in SEQ ID NO:24. In some embodiments, the nucleotide construct encodes a peptide that comprises the amino acid sequence set forth in SEQ ID NO:4. In some embodiments, the nucleotide construct encodes a peptide that comprises an amino acid sequence that has at least about 70% (e.g., about 70%, 75%, 80%, 85%, 86%, 87%, 88%, 89%, 90%, 90%, 91%, 92%, 93%, 94%, 95%, 96%, 97%, 98%, 99%, or 100%) identity to the sequence set forth in SEQ ID NO:4.

In some embodiments, the nucleotide construct encodes a peptide that is at least about 200 amino acids in length. In other embodiments, the nucleotide construct encodes a peptide that is about 100 to about 200 (e.g., about 100, 105, 110, 115, 120, 125, 130, 135, 140, 145, 150, 155, 160, 165, 170, 175, 180, 185, 190, 195, or 200) amino acids in length. In some other embodiments, the nucleotide construct encodes a peptide that is about 5 to about 100 (e.g., about 5, 10, 15, 20, 25, 30, 35, 40, 45, 50, 55, 60, 65, 70, 75, 80, 85, 90, 95, or 100) amino acids in length. In particular embodiments, the nucleotide construct encodes a peptide that is about 5 to about 50 (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) amino acids in length. In some instances, the nucleotide construct encodes a peptide that is about 40 amino acids in length. In other instances, the nucleotide construct encodes a peptide that is about 23 amino acids in length. In some other instances, the nucleotide construct encodes a peptide that is about 25 amino acids in length. In still other instances, the nucleotide construct encodes a peptide that is about 8 amino acids in length.

In some other embodiments, the nucleotide construct encodes a conjugate. In particular embodiments, the nucleotide construct encodes a conjugate that comprises a peptide of the present invention and a cell-penetrating peptide (CPP). In some embodiments, the nucleotide construct encodes a conjugate that comprises a peptide comprising the amino acid sequence set forth in SEQ ID NO:1, 2, 3, 4, 52, 53, or 54. In particular embodiments, the nucleotide construct encodes a conjugate wherein the peptide and the CPP are covalently linked. In some instances, the nucleotide construct encodes a conjugate wherein the CPP is selected from the group consisting of PEP1, Penetratin™, and a combination thereof.

In some embodiments, the nucleotide construct encodes a conjugate that comprises an amino acid sequence that has at least about 70% (e.g., about 70%, 75%, 80%, 85%, 86%, 87%, 88%, 89%, 90%, 90%, 91%, 92%, 93%, 94%, 95%, 96%, 97%, 98%, 99%, or 100%) identity to the sequence set forth in SEQ ID NO:9, 50, 51, 55, or 65. In some embodiments, the nucleotide construct encodes a conjugate that comprises an amino acid sequence set forth in SEQ ID NO:9, 50, 51, 55, or 65.

In yet another aspect, the invention provides a vector comprising a nucleotide construct of the present invention. In still another aspect, the invention provides a cell comprising one or more vectors of the present invention. In some embodiments, the cell expresses a peptide comprising the amino acid sequence set forth in SEQ ID NO:1, 2, 3, 4, 5, 6, 7, 8, 52, 53, 54, 56, 57, 58, 59, 60, 61, 62, 63, or 64, a conjugate comprising a peptide comprising the amino acid sequence set forth in SEQ ID NO:1, 2, 3, 4, 52, 53, or 54 and a CPP, or a combination thereof. Non-limiting examples of suitable CPPs are described herein. In some embodiments, the cell expresses a conjugate that comprises an amino acid sequence set forth in SEQ ID NO:9, 50, 51, 55, or 65. In some embodiments, the cell is first isolated from a subject before the one or more vectors are introduced into the cell. In some instances, the cell is introduced into the subject after the one or more vectors are introduced into the cell. In some embodiments, the cell comprises a population of cells and/or the progeny thereof.

In other aspects, compositions of the present invention (e.g., peptides, conjugates, oligonucleotides, and/or other compositions) further comprise a pharmaceutically acceptable carrier. The formulation of pharmaceutical compositions is generally known in the art (see, e.g., *REMINGTON'S PHARMACEUTICAL SCIENCES*, 18TH ED., Mack Publishing Co., Easton, Pa. (1990)). Prevention against microorganism contamination can be achieved through the addition of one or more of various antibacterial and antifungal agents.

Pharmaceutical forms suitable for administration include sterile aqueous solutions or dispersions and sterile powders for the extemporaneous preparation of sterile injectable solutions or dispersions. Typical carriers include a solvent or dispersion medium containing, for example, water-buffered aqueous solutions (i.e., biocompatible buffers), ethanol, polyols such as glycerol, propylene glycol, polyethylene glycol, suitable mixtures thereof, surfactants, or vegetable oils.

Sterilization can be accomplished by an art-recognized technique, including but not limited to filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing peptide(s), conjugate(s), oligonucleotide(s), and/or other composition(s) of the present invention can be accomplished by incorporating the compound(s) in the required amount(s) in the appropriate solvent with various ingredients enumerated above, as required, followed by sterilization (e.g., filter sterilization). To obtain a sterile powder, the above sterile solutions can be vacuum-dried or freeze-dried as necessary.

In some embodiments, the peptide(s), conjugate(s), oligonucleotide(s), and/or other composition(s) provided herein are formulated for administration, e.g., oral, nasal, topical, or parental administration in unit dosage form for ease of administration and uniformity of dosage. Unit dosage forms, as used herein, refers to physically discrete units suited as unitary dosages for the subjects, e.g., humans or other mammals to be treated, each unit containing a predetermined quantity of active material calculated to produce the desired therapeutic effect in association with the required pharmaceutical carrier. In some instances, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the peptide(s), conjugate(s), oligonucleotide(s), and/or other composition(s).

Methods for preparing such dosage forms are known to those skilled in the art (see, e.g., *REMINGTON'S PHARMACEUTICAL SCIENCES*, supra). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., *REMINGTON'S PHARMACEUTICAL SCIENCES*, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

In some embodiments, the composition for administration may be an oral delivery vehicle such as a capsule, cachet or tablet, each of which contains a predetermined amount of the peptide to provide the correct incremental dose to the patient. Oral delivery vehicles may be useful, for example, in avoiding contact between the peptide and the mouth and upper gastrointestinal tract. For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with the peptide(s), conjugate(s), oligonucleotide(s), and/or other composition(s) described herein, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

In some embodiments, a suitable carrier masks the composition, e.g., the peptide(s), conjugate(s), oligonucleotide(s), and/or other composition(s) from the mouth and upper gastrointestinal (GI) tract and reduces or prevents local itching/swelling reactions in these regions during administration. For example, a carrier may contain one or more lipid, polysaccharide or protein constituents. In some cases, the carrier is a food product.

For topical administration, the therapeutically effective dose can be in the form of emulsions, lotions, gels, foams, creams, jellies, solutions, suspensions, ointments, and transdermal patches. For administration by inhalation, the peptide(s), conjugate(s), oligonucleotide(s), and/or other composition(s) described herein can be delivered as a dry powder or in liquid form via a nebulizer. Aerosol formulations can be placed into pressurized acceptable propellants such as dichlorodifluoromethane. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In some embodiments, the therapeutically effective dose may further comprise other components, for example, anti-allergy drugs, such as antihistamines, steroids, bronchodilators, leukotriene stabilizers and mast cell stabilizers. Suitable anti-allergy drugs are well known in the art.

D. Kits

In another aspect, the present invention provides a kit for preventing or treating cancer in a subject. The kits are useful for treating any cancer, some non-limiting examples of which include colorectal cancer, colon cancer, anal cancer, liver cancer, ovarian cancer, breast cancer, lung cancer, bladder cancer, thyroid cancer, pleural cancer, pancreatic cancer, cervical cancer, prostate cancer, testicular cancer, bile duct cancer, gastrointestinal carcinoid tumors, esophageal cancer, gall bladder cancer, rectal cancer, appendix cancer, small intestine cancer, stomach (gastric) cancer, renal cancer (i.e., renal cell carcinoma), cancer of the central nervous system, skin cancer, oral squamous cell carcinoma, choriocarcinomas, head and neck cancers, bone cancer, osteogenic sarcomas, fibrosarcoma, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma. In some embodiments, the kits comprise a peptide of the present invention, a conjugate of the present invention, an oligonucleotide of the present invention, a peptide-based pharmaceutical composition of the present invention, an oligonucleotide-based pharmaceutical composition of the present invention, a vector of the present invention, a cell of the present invention, or a combination thereof.

Materials and reagents to carry out the various methods of the present invention can be provided in kits to facilitate execution of the methods. As used herein, the term "kit" includes a combination of articles that facilitates a process, assay, analysis, or manipulation. In particular, kits comprising the peptides, conjugates, oligonucleotides, pharmaceutical compositions, vectors, cells, or other compositions of the present invention find utility in a wide range of applications including, for example, diagnostics, prognostics, therapy, and the like.

In some embodiments, the kits comprise a peptide and/or conjugate that comprises the amino acid sequence set forth in SEQ ID NO:1, 2, 3, 4, 5, 6, 7, 8, 9, 50, 51, 52, 53, 54, 55, 56, 57, 58, 59, 60, 61, 62, 63, 64, or 65, or a combination thereof. In other embodiments, the kits comprise at least one peptide or conjugate. In some other embodiments, the kits comprise at least two or more peptides and/or conjugates (e.g., at least 2, 3, 4, 5, 6, 7, 8, 9, 10, 11, 12, 13, 14, 15, 16, 17, 18, 19, 20, 21, 22, 23, 24, 25, or more peptides and/or conjugates).

In other embodiments, the kits comprise an oligonucleotide that comprises the nucleotide sequence set forth in SEQ ID NO:16, 17, 18, 19, 20, 21, 45, 46, 47, 48, 49, or a combination thereof. In other embodiments, the kits comprise at least one oligonucleotide (e.g., at least 1, 2, 3, 4, 5, 6, 7, 8, 9, 10, 11, or more oligonucleotides).

Kits can contain chemical reagents as well as other components. In addition, the kits of the present invention can include, without limitation, instructions to the kit user, apparatus and reagents for sample collection and/or purification, apparatus and reagents for product collection and/or purification, sample tubes, holders, trays, racks, dishes, plates, solutions, buffers or other chemical reagents, suitable samples to be used for standardization, normalization, and/or control samples. Kits of the present invention can also be packaged for convenient storage and safe shipping, for example, in a box having a lid.

In some embodiments, the kits also contain negative and positive control samples for detection of biomarkers. Suitable biomarkers include but are not limited to p53, p21, mouse double minute 2 homolog (MDM2), Puma, and p-eIF4E (e.g., p-eIF4E (Ser209)). In some instances, the negative control samples are obtained from individuals or groups of individuals who do not have cancer. In other instances, the positive control samples are obtained from individuals or groups of individuals who have cancer. In some embodiments, the kits contain samples for the preparation of a titrated curve of antibodies in a sample, to assist in the evaluation of quantified levels of antibodies in a test biological sample.

E. Methods for Preventing or Treating Cancer

In another aspect, the invention provides methods for preventing or treating cancer in a subject. In some embodiments, the method comprises administering to the subject a therapeutically effective amount of a peptide of the present invention or a plurality thereof, a conjugate of the present invention or a plurality thereof, an oligonucleotide of the present invention or a plurality thereof, a peptide-based pharmaceutical composition of the present invention, an oligonucleotide-based pharmaceutical composition of the present invention, a vector of the present invention, a cell of the present invention, or a combination thereof. In some embodiments, preventing or treating cancer in the subject further comprises delivering an anti-cancer agent (e.g., chemotherapeutic agent), radiation therapy, or a combination thereof to the subject. Examples of suitable chemotherapeutic agents are described in detail above in the section titled "Compositions." In some embodiments, the chemotherapeutic agent is doxorubicin and/or etoposide. In some instances, the effect (e.g., therapeutic effect) of a chemotherapeutic agent (e.g., doxorubicin, etoposide) in enhanced.

In another aspect, the invention provides methods for enhancing the effect (e.g., therapeutic effect) of an anti-cancer agent (e.g., in a subject who is receiving an anti-cancer agent). In some embodiments, the method comprises administering to a subject (e.g., to a subject being treated for cancer) a therapeutically effective amount of a peptide of the present invention or a plurality thereof, a conjugate of the present invention or a plurality thereof, an oligonucleotide of the present invention or a plurality thereof, a peptide-based pharmaceutical composition of the present invention, an oligonucleotide-based pharmaceutical composition of the present invention, a vector of the present invention, a cell of the present invention, or a combination thereof. In some embodiments, the method further comprises delivering radiation therapy to the subject.

In some embodiments, the anti-cancer agent is a chemotherapeutic agent. Examples of suitable chemotherapeutic agents are described in detail above in the section titled "Compositions." In particular embodiments, the chemotherapeutic agent is a type II topoisomerase inhibitor. In some instances, the type II topoisomerase inhibitor is selected from the group consisting of doxorubicin, etoposide, and a combination thereof.

The methods of the present invention are applicable to the prevention or treatment of any number of cancers, some non-limiting examples of which include colorectal cancer, colon cancer, anal cancer, liver cancer, ovarian cancer, breast cancer, lung cancer, bladder cancer, thyroid cancer, pleural cancer, pancreatic cancer, cervical cancer, prostate cancer, testicular cancer, bile duct cancer, gastrointestinal carcinoid tumors, esophageal cancer, gall bladder cancer, rectal cancer, appendix cancer, small intestine cancer, stomach (gastric) cancer, renal cancer (i.e., renal cell carcinoma), cancer of the central nervous system, skin cancer, oral squamous cell carcinoma, choriocarcinomas, head and neck cancers, bone cancer, osteogenic sarcomas, fibrosarcoma, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma.

In some embodiments, one or more peptides and/or conjugates (e.g., 1, 2, 3, 4, 5, 6, 7, 8, 9, 10, 11, 12, 13, 14, 15, 16, 17, 18, 19, 20, 21, 22, 23, 24, 25, or more peptides and/or conjugates) are administered. In some embodiments, the one or more peptides and/or conjugates comprise the amino acid sequence set forth in SEQ ID NO:1, 2, 3, 4, 5, 6, 7, 8, 9, 50, 51, 52, 53, 54, 55, 56, 57, 58, 59, 60, 61, 62, 63, 64, or 65, or a combination thereof.

In some embodiments, one or more oligonucleotides (e.g., 1, 2, 3, 4, 5, 6, 7, 8, 9, 10, 11, or more oligonucleotides) are administered. In some embodiments, the one or more oligonucleotides comprise the nucleotide sequence set forth in SEQ ID NO: 16, 17, 18, 19, 20, 21, 45, 46, 47, 48, or 49, or a combination thereof.

In some embodiments, administering the peptide or plurality thereof, conjugate or plurality thereof, oligonucleotide or plurality thereof, peptide-based pharmaceutical composition, oligonucleotide-based pharmaceutical composition, vector, cell, or a combination thereof increases p53 expression and/or activity (e.g., in one or more cells in the subject). In some embodiments, p53 expression is increased. In particular embodiments, the expression of p53 mRNA is increased. In other embodiments, the expression of p53 protein is increased. In some embodiments, p53 activity is increased. In other embodiments, increasing p53 expression and/or activity comprises increasing the association between eIF4E and p53 mRNA. In some embodiments, increasing p53 expression and/or activity comprises increasing the expression and/or activity of a downstream p53 target (e.g., p21, Puma). In other embodiments, increasing p53 expression and/or activity comprises decreasing the expression and/or activity of a downstream p53 target. In some embodiments, p53 expression and/or activity (e.g., in a test sample) is increased by at least about 1.1-, 1.2-, 1.3-, 1.4-, 1.5-, 1.6-, 1.7-, 1.8-, 1.9-, 2-, 2.1-, 2.2-, 2.3-, 2.4-, 2.5-, 2.6-, 2.7-, 2.8-, 2.9-, 3-, 3.1-, 3.2-, 3.3-, 3.4-, 3.5-, 3.6-, 3.7-, 3.8-, 3.9-, 4-, 4.1-, 4.2-, 4.3-, 4.4-, 4.5-, 4.6-, 4.7-, 4.8-, 4.9-, 5-, 5.5-, 6-, 6.5-, 7-, 7.5-, 8-, 8.5-, 9-, 9.5-, 10-, 10.5-, 11-, 11.5-, 12-, 12.5-, 13-, 13.5-, 14-, 14.5-, 15-, 15.5-, 16-, 16.5-, 17-, 17.5-, 18-, 18.5-, 19-, 19.5-, or 20-fold (e.g., compared to when the peptide or plurality thereof, conjugate or plurality thereof, oligonucleotide or plurality thereof, peptide-based pharmaceutical composition, oligonucleotide-based pharmaceutical composition, vector cell, or a combination thereof is not administered). The expression and/or activity of p53, including that of downstream p53 targets, can be determined, for example, by measuring the level of one or more biomarkers, as described further below.

In some embodiments, administering the peptide or plurality thereof, conjugate or plurality thereof, oligonucleotide or plurality thereof, peptide-based pharmaceutical composition, oligonucleotide-based pharmaceutical composition, vector, cell, or a combination thereof decreases eIF4E phosphorylation (e.g., phosphorylation of Ser209). In some embodiments, the ability of MNK1 and/or MNK2 to phosphorylate eIF4E is decreased. In some embodiments, eIF4E phosphorylation (e.g., in a test sample) is decreased by at least about 1.1-, 1.2-, 1.3-, 1.4-, 1.5-, 1.6-, 1.7-, 1.8-, 1.9-, 2-, 2.1-, 2.2-, 2.3-, 2.4-, 2.5-, 2.6-, 2.7-, 2.8-, 2.9-, 3-, 3.1-, 3.2-, 3.3-, 3.4-, 3.5-, 3.6-, 3.7-, 3.8-, 3.9-, 4-, 4.1-, 4.2-, 4.3-, 4.4-, 4.5-, 4.6-, 4.7-, 4.8-, 4.9-, 5-, 5.5-, 6-, 6.5-, 7-, 7.5-, 8-, 8.5-, 9-, 9.5-, 10-, 10.5-, 11-, 11.5-, 12-, 12.5-, 13-, 13.5-, 14-, 14.5-, 15-, 15.5-, 16-, 16.5-, 17-, 17.5-, 18-, 18.5-, 19-, 19.5-, or 20-fold (e.g., compared to when the peptide or plurality thereof, conjugate or plurality thereof, oligonucleotide or plurality thereof, peptide-based pharmaceutical composition, oligonucleotide-based pharmaceutical composition, vector cell, or a combination thereof is not administered). eIF4E phosphorylation can be determined, for example, by measuring the level of one or more biomarkers, as described further below.

In some embodiments, the subject does not have cancer. In other embodiments, the subject (e.g., the subject being treated) is exhibiting one or more symptoms of cancer. In some embodiments, the cancer is an advanced stage cancer (e.g., advanced stage breast or colon cancer). In some embodiments, the cancer is metastatic (e.g., metastatic breast or colon cancer). In some embodiments, administering a compound of the present invention (i.e., to treat the subject) inhibits cancer cell growth; inhibits cancer cell migration; inhibits cancer cell invasion; ameliorates the symptoms of cancer; reduces the size of a cancer tumor; reduces the number of cancer tumors; reduces the number of cancer cells; or induces cancer cell necrosis, pyroptosis, oncosis, apoptosis, autophagy, or other cell death.

In some embodiments, reducing the size of a cancer tumor comprises reducing the weight and/or volume of a cancer tumor. In some embodiments, the weight of a cancer tumor is reduced, e.g., by at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%. In particular embodiments, the weight of a cancer tumor is reduced at least about 30% to about 70%. In some instances, the weight of a cancer tumor is reduced by at least about 50%. Tumor weight can be measured at any time point or a combination of time points. As a non-limiting example, tumor weight can be measured about 1, 2, 3, 4, 5, 6, 7, 8, 9, 10, or more days after treatment has started. As another non-limiting example, tumor weight can be measured about 1, 2, 3, 4, 5, 6, 7, 8, 9, 10, or more weeks after treatment has started. As a further non-limiting example, tumor weight can be measured about 1, 2, 3, 4, 5, 6, 7, 8, 9, 10, 11, 12, or more months after treatment has started.

In some embodiments, the volume of a cancer tumor is reduced, e.g., by at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%. In particular embodiments, the volume of a cancer tumor is reduced at least about 30% to about 70%. In some instances, the volume of a cancer tumor is reduced by at least about 50%. Tumor volume can be measured at any time point or a combination of time points. As a non-limiting example, tumor volume can be measured about 1, 2, 3, 4, 5, 6, 7, 8, 9, 10, or more days after treatment has started. As another non-limiting example, tumor volume can be measured about 1, 2, 3, 4, 5, 6, 7, 8, 9, 10, or more weeks after treatment has started. As a further non-limiting example, tumor volume can be measured about 1, 2, 3, 4, 5, 6, 7, 8, 9, 10, 11, 12, or more months after treatment has started.

As used herein, the phrase "ameliorates the symptoms of cancer" includes alleviating or improving the symptoms or condition of a patient having cancer (e.g., breast or colon cancer). Ameliorating the symptoms includes reducing the pain or discomfort associated with cancer. Ameliorating the symptoms also includes reducing the markers of cancer, e.g., reducing the number of cancer cells or reducing the size of cancer tumors.

In particular embodiments, a test sample is obtained from the subject. The test sample can be obtained before and/or after the peptide or plurality thereof, conjugate or plurality thereof, oligonucleotide or plurality thereof, peptide-based pharmaceutical composition, oligonucleotide-based pharmaceutical composition, vector, cell, or a combination thereof is administered to the subject. Non-limiting examples of suitable samples include blood, serum, plasma, cerebrospinal fluid, tissue, saliva, and urine. In some instances, the test sample comprises normal tissue. In other instances, the test sample comprises cancer tissue. The test sample can also be made up of normal and/or cancer cells.

In some embodiments, a reference sample is obtained. The reference sample can be obtained, for example, from the subject and can comprise normal tissue. The reference sample can be also be obtained from a different subject and/or a population of subjects. In some instances, the reference sample is obtained from the subject, a different subject, or a population of subjects before and/or after the peptide or plurality thereof, conjugate or plurality thereof, oligonucleotide or plurality thereof, peptide-based pharmaceutical composition, oligonucleotide-based pharmaceutical composition, vector, cell, or a combination thereof is administered to the subject, and comprises normal tissue. In other instances, the reference sample comprises cancer tissue and is obtained from the subject and/or from a different subject or a population of subjects before and/or after the peptide or plurality thereof, conjugate or plurality thereof, oligonucleotide or plurality thereof, peptide-based pharmaceutical composition, oligonucleotide-based pharmaceutical composition, vector, cell, or a combination thereof is administered to the subject.

In some embodiments, the level of one or more biomarkers is determined in the test sample and/or reference sample. A biomarker can comprise an mRNA expression level (e.g., p53 mRNA level), a protein expression level (e.g., p53 protein level), a modified protein level (e.g., phosphorylated p53 or phosphorylated eIF4E (e.g., p-eIF4E (Ser209)) protein level), or any combination thereof. Non-limiting examples of suitable biomarkers include p53, p21, mouse double minute 2 homolog (MDM2), Puma, and p-eIF4E (e.g., p-eIF4E (Ser209)). Other downstream targets in the p53 pathway are also suitable biomarkers. Typically, the level of the one or more biomarkers in one or more test samples is compared to the level of the one or more biomarkers in one or more reference samples. As a non-limiting example, levels of one or biomarkers in test samples taken before and after the peptide or plurality thereof, conjugate or plurality thereof, oligonucleotide or plurality thereof, peptide-based pharmaceutical composition, oligonucleotide-based pharmaceutical composition, vector, cell, or a combination thereof is administered to the subject are compared to the level of the one or more biomarkers in a reference sample that is either normal tissue obtained from the subject, or normal tissue that is obtained from a different subject or a population of subjects. In some instances, the biomarker is p53 protein, and the level of p53 protein in a test sample obtained from the subject before the peptide or plurality thereof, conjugate or plurality thereof, oligonucleotide or plurality thereof, peptide-based pharmaceutical composition, oligonucleotide-based pharmaceutical composition, vector, cell, or a combination thereof is administered to the subject is lower than the level of p53 in the reference sample. In other instances, the level of p53 protein in a test sample obtained from the subject after administration of the peptide or plurality thereof, conjugate or plurality thereof, oligonucleotide or plurality thereof, peptide-based pharmaceutical composition, oligonucleotide-based pharmaceutical composition, vector, cell, or a combination thereof is increased relative to the level of p53 in a test sample obtained prior to administration. Alternatively, as another non-limiting example, the difference in p53 protein level between a sample obtained from the subject after administration and a reference sample is smaller than a difference between the p53 protein level in a sample obtained from the subject prior to administration and the reference sample (i.e., administration results in an increase in p53 in the test sample such that the difference between the level measured in the test sample and the level measured in the reference sample is diminished or abolished).

In other instances, the biomarker is p-eIF4E (Ser209), and the level of p-eIF4E (Ser209) in a test sample obtained from the subject before the peptide or plurality thereof, conjugate or plurality thereof, oligonucleotide or plurality thereof, peptide-based pharmaceutical composition, oligonucleotide-based pharmaceutical composition, vector, cell, or a combination thereof is administered to the subject is higher than the level of p-eIF4E (Ser209) in the reference sample. In other instances, the level of p-eIF4E (Ser209) in a test sample obtained from the subject after administration of the peptide or plurality thereof, conjugate or plurality thereof, oligonucleotide or plurality thereof, peptide-based pharmaceutical composition, oligonucleotide-based pharmaceutical composition, vector, cell, or a combination thereof is decreased relative to the level of p-eIF4E (Ser209) in a test sample obtained prior to administration. Alternatively, as another non-limiting example, the difference in p-eIF4E (Ser209) level between a sample obtained from the subject after administration and a reference sample is smaller than a difference between the p-eIF4E (Ser209) level in a sample obtained from the subject prior to administration and the reference sample (i.e., administration results in an decrease in p-eIF4E (Ser209) in the test sample such that the difference between the level measured in the test sample and the level measured in the reference sample is diminished or abolished).

The differences between the reference sample or value and the test sample need only be sufficient to be detected. In some embodiments, a decreased level of a biomarker (e.g., p53 protein) in the test sample, and hence the presence of cancer or increased risk of cancer, is determined when the biomarker levels are at least, e.g., about 10%, 25%, 50%, or 75% lower in comparison to a negative control. In some embodiments, an increased level of a biomarker in the test sample, and hence the presence of cancer or increased risk of cancer, is determined when the biomarker levels are at least, e.g., about 10%, 25%, 50%, or 75% higher in comparison to a negative control.

In some embodiments, administering the peptide or plurality thereof, conjugate or plurality thereof, oligonucleotide or plurality thereof, peptide-based pharmaceutical composition, oligonucleotide-based pharmaceutical composition, vector, cell, or a combination thereof increases the level of a biomarker in a test sample (e.g., a test sample obtained after administration) by at least about 1.1-, 1.2-, 1.3-, 1.4-, 1.5-, 1.6-, 1.7-, 1.8-, 1.9-, 2-, 2.1-, 2.2-, 2.3-, 2.4-, 2.5-, 2.6-, 2.7-, 2.8-, 2.9-, 3-, 3.1-, 3.2-, 3.3-, 3.4-, 3.5-, 3.6-, 3.7-, 3.8-, 3.9-, 4-, 4.1-, 4.2-, 4.3-, 4.4-, 4.5-, 4.6-, 4.7-, 4.8-, 4.9-, 5-, 5.5-, 6-, 6.5-, 7-, 7.5-, 8-, 8.5-, 9-, 9.5-, 10-, 10.5-, 11-, 11.5-, 12-, 12.5-, 13-, 13.5-, 14-, 14.5-, 15-, 15.5-, 16-, 16.5-, 17-, 17.5-, 18-, 18.5-, 19-, 19.5-, or 20-fold compared to a control value (e.g., a value measured or determined in a reference sample or a separate test sample).

In some embodiments, administering the peptide or plurality thereof, conjugate or plurality thereof, oligonucleotide or plurality thereof, peptide-based pharmaceutical composition, oligonucleotide-based pharmaceutical composition, vector, cell, or a combination thereof decreases the level of a biomarker in a test sample (e.g., a test sample obtained after administration) by at least about 1.1-, 1.2-, 1.3-, 1.4-, 1.5-, 1.6-, 1.7-, 1.8-, 1.9-, 2-, 2.1-, 2.2-, 2.3-, 2.4-, 2.5-, 2.6-, 2.7-, 2.8-, 2.9-, 3-, 3.1-, 3.2-, 3.3-, 3.4-, 3.5-, 3.6-, 3.7-, 3.8-, 3.9-, 4-, 4.1-, 4.2-, 4.3-, 4.4-, 4.5-, 4.6-, 4.7-, 4.8-, 4.9-, 5-, 5.5-, 6-, 6.5-, 7-, 7.5-, 8-, 8.5-, 9-, 9.5-, 10-, 10.5-, 11-, 11.5-, 12-, 12.5-, 13-, 13.5-, 14-, 14.5-, 15-, 15.5-, 16-, 16.5-, 17-, 17.5-, 18-, 18.5-, 19-, 19.5-, or 20-fold compared to a control value (e.g., a value measured or determined in a reference sample or a separate test sample).

The biomarker levels can be detected using any method known in the art, including the use of antibodies specific for the biomarkers. Exemplary methods include, without limitation, Western Blot, dot blot, enzyme-linked immunosorbent assay (ELISA), radioimmunoassay (RIA), immunoprecipitation, RNA-ChIP assay, immunofluorescence, FACS analysis, electrochemiluminescence, and multiplex bead assays (e.g., using Luminex or fluorescent microbeads).

In some embodiments, the antibody or plurality thereof used to detect the biomarker(s) can be immobilized on a solid support. The solid support can be, for example, a multiwell plate, a microarray, a chip, a bead, a porous strip, or a nitrocellulose filter. In some instances, the bead comprises chitin. The immobilization can be via covalent or non-covalent binding.

Labeled secondary antibodies can be used to detect binding between antibodies and biomarkers. Secondary antibodies bind to the constant or "C" regions of different classes or isotypes of immunoglobulins IgM, IgD, IgG, IgA, and IgE. Usually, a secondary antibody against an IgG constant region is used in the present methods. Secondary antibodies against the IgG subclasses, for example, IgG1, IgG2, IgG3, and IgG4, also find use in the present methods. Secondary antibodies can be labeled with any directly or indirectly detectable moiety, including a fluorophore (e.g., fluorescein, phycoerythrin, quantum dot, Luminex bead, fluorescent bead), an enzyme (e.g., peroxidase, alkaline phosphatase), a radioisotope (e.g., $^3$H, $^{32}$P, $^{125}$I) or a chemiluminescent moiety. Labeling signals can be amplified using a complex of biotin and a biotin binding moiety (e.g., avidin, streptavidin, neutravidin). Fluorescently labeled anti-human IgG antibodies are commercially available from Molecular Probes, Eugene, Oreg. Enzyme-labeled anti-human IgG antibodies are commercially available from Sigma-Aldrich, St. Louis, Mo. and Chemicon, Temecula, Calif.

General immunoassay techniques are well known in the art. Guidance for optimization of parameters can be found in, for example, Wu, Quantitative Immunoassay: A Practical Guide for Assay Establishment, Troubleshooting, and Clinical Application, 2000, AACC Press; Principles and Practice of Immunoassay, Price and Newman, eds., 1997, Groves Dictionaries, Inc.; The Immunoassay Handbook, Wild, ed., 2005, Elsevier Science Ltd.; Ghindilis, Pavlov and Atanassov, Immunoassay Methods and Protocols, 2003, Humana Press; Harlow and Lane, Using Antibodies: A Laboratory Manual, 1998, Cold Spring Harbor Laboratory Press; and Immunoassay Automation: An Updated Guide to Systems, Chan, ed., 1996, Academic Press.

In certain embodiments, the presence or decreased or increased presence of one or more biomarkers is indicated by a detectable signal (e.g., a blot, fluorescence, chemiluminescence, color, radioactivity) in an immunoassay. This detectable signal can be compared to the signal from a control sample or to a threshold value. In some embodiments, decreased presence is detected, and the presence or increased risk of cancer is indicated, when the detectable signal of biomarker(s) in the test sample is at least about 10%, 20%, 30%, 50%, 75% lower in comparison to the signal of antibodies in the reference sample or the predetermined threshold value. In other embodiments, an increased presence is detected, and the presence or increased risk of cancer is indicated, when the detectable signal of biomarker(s) in the test sample is at least about 1-fold, 2-fold, 3-fold, 4-fold or more, greater in comparison to the signal of antibodies in the reference sample or the predetermined threshold value.

In some embodiments, the results of the biomarker level determinations are recorded in a tangible medium. For example, the results of diagnostic assays (e.g., the observation of the presence or decreased or increased presence of one or more biomarkers) and the diagnosis of whether or not there is an increased risk or the presence of cancer can be recorded, e.g., on paper or on electronic media (e.g., audio tape, a computer disk, a CD, a flash drive, etc.).

In other embodiments, the methods further comprise the step of providing the diagnosis to the patient (i.e., the subject) and/or the results of treatment.

F. Methods for Modulating p53 Activity and eIF4E Phosphorylation

In another aspect, the invention provides methods for increasing the expression and/or activity of p53 in a subject (e.g., in one or more cells in a subject). In some embodiments, the method comprises administering to the subject a therapeutically effective amount of a peptide of the present invention or a plurality thereof, a conjugate of the present invention or a plurality thereof, an oligonucleotide of the present invention or a plurality thereof, a peptide-based pharmaceutical composition of the present invention, an oligonucleotide-based pharmaceutical composition of the present invention, a vector of the present invention, a cell of the present invention, or a combination thereof.

In some embodiments, p53 expression is increased. In particular embodiments, the expression of p53 mRNA is increased. In other embodiments, the expression of p53 protein is increased. In some embodiments, p53 activity is increased. In other embodiments, increasing p53 expression and/or activity comprises increasing the association between eIF4E and p53 mRNA. In some embodiments, increasing p53 expression and/or activity comprises increasing the expression and/or activity of a downstream p53 target (e.g., p21, Puma). In other embodiments, increasing p53 expression and/or activity comprises decreasing the expression and/or activity of a downstream p53 target. In some embodiments, p53 expression and/or activity (e.g., in a test sample) is increased by at least about 1.1-, 1.2-, 1.3-, 1.4-, 1.5-, 1.6-, 1.7-, 1.8-, 1.9-, 2-, 2.1-, 2.2-, 2.3-, 2.4-, 2.5-, 2.6-, 2.7-, 2.8-, 2.9-, 3-, 3.1-, 3.2-, 3.3-, 3.4-, 3.5-, 3.6-, 3.7-, 3.8-, 3.9-, 4-, 4.1-, 4.2-, 4.3-, 4.4-, 4.5-, 4.6-, 4.7-, 4.8-, 4.9-, 5-, 5.5-, 6-, 6.5-, 7-, 7.5-, 8-, 8.5-, 9-, 9.5-, 10-, 10.5-, 11-, 11.5-, 12-, 12.5-, 13-, 13.5-, 14-, 14.5-, 15-, 15.5-, 16-, 16.5-, 17-, 17.5-, 18-, 18.5-, 19-, 19.5-, or 20-fold (e.g., compared to when the peptide or plurality thereof, conjugate or plurality thereof, oligonucleotide or plurality thereof, peptide-based pharmaceutical composition, oligonucleotide-based pharmaceutical composition, vector cell, or a combination thereof is not administered). The expression and/or activity of p53, including that of downstream p53 targets, can be determined, for example, by measuring the level of one or more biomarkers, as described further below.

In another aspect, the invention provides methods for decreasing eIF4E phosphorylation (e.g., phosphorylation of Ser209) in a subject (e.g., in one or more cells in a subject). In some embodiments, the method comprises administering to the subject a therapeutically effective amount of a peptide of the present invention or a plurality thereof, a conjugate of the present invention or a plurality thereof, an oligonucleotide of the present invention or a plurality thereof, a peptide-based pharmaceutical composition of the present invention, an oligonucleotide-based pharmaceutical composition of the present invention, a vector of the present invention, a cell of the present invention, or a combination thereof.

In some embodiments, the ability of MNK1 and/or MNK2 to phosphorylate eIF4E is decreased. In some embodiments, the phosphorylation of eIF4E at Ser209 is decreased. In some embodiments, eIF4E phosphorylation (e.g., in a test sample) is decreased by at least about 1.1-, 1.2-, 1.3-, 1.4-, 1.5-, 1.6-, 1.7-, 1.8-, 1.9-, 2-, 2.1-, 2.2-, 2.3-, 2.4-, 2.5-, 2.6-, 2.7-, 2.8-, 2.9-, 3-, 3.1-, 3.2-, 3.3-, 3.4-, 3.5-, 3.6-, 3.7-, 3.8-, 3.9-, 4-, 4.1-, 4.2-, 4.3-, 4.4-, 4.5-, 4.6-, 4.7-, 4.8-, 4.9-, 5-, 5.5-, 6-, 6.5-, 7-, 7.5-, 8-, 8.5-, 9-, 9.5-, 10-, 10.5-, 11-, 11.5-, 12-, 12.5-, 13-, 13.5-, 14-, 14.5-, 15-, 15.5-, 16-, 16.5-, 17-, 17.5-, 18-, 18.5-, 19-, 19.5-, or 20-fold (e.g., compared to when the peptide or plurality thereof, conjugate or plurality thereof, oligonucleotide or plurality thereof, peptide-based pharmaceutical composition, oligonucleotide-based pharmaceutical composition, vector cell, or a combination thereof is not administered). eIF4E phosphorylation can be determined, for example, by measuring the level of one or more biomarkers, as described further below.

For practicing methods of increasing p53 expression and/or activity and methods of decreasing eIF4E phosphorylation, one or more peptides and/or conjugates (e.g., 1, 2, 3, 4, 5, 6, 7, 8, 9, 10, 11, 12, 13, 14, 15, 16, 17, 18, 19, 20, 21, 22, 23, 24, 25, or more peptides and/or conjugates) can be administered. In some embodiments, the one or more peptides and/or conjugates comprise the amino acid sequence set forth in SEQ ID NO:1, 2, 3, 4, 5, 6, 7, 8, 9, 50, 51, 52, 53, 54, 55, 56, 57, 58, 59, 60, 61, 62, 63, 64, or 65, or a combination thereof Furthermore, one or more oligonucleotides (e.g., 1, 2, 3, 4, 5, 6, 7, 8, 9, 10, 11, or more oligonucleotides) can be administered. In some embodiments, the one or more oligonucleotides comprise the nucleotide sequence set forth in SEQ ID NO: 16, 17, 18, 19, 20, 21, 45, 46, 47, 48, or 49, or a combination thereof.

In some embodiments, the subject does not have a disease associated with abnormal p53 activity and/or expression (e.g., cancer). In other embodiments, the subject does not have a disease associated with abnormal eIF4E phosphorylation (e.g., cancer). In still other embodiments, the subject is being treated for and/or is exhibiting one or more symptoms of a disease associated with abnormal p53 expression and/or activity and/or abnormal eIF4E phosphorylation. In some embodiments, the subject being treated for and/or is exhibiting one or more symptoms of cancer.

In particular embodiments, a test sample is obtained from the subject. The test sample can be obtained before and/or after the peptide or plurality thereof, conjugate or plurality thereof, oligonucleotide or plurality thereof, peptide-based pharmaceutical composition, oligonucleotide-based pharmaceutical composition, vector, cell, or a combination thereof is administered to the subject. Non-limiting examples of suitable samples include blood, serum, plasma, cerebrospinal fluid, tissue, saliva, and urine. In some instances, the test sample comprises normal tissue. In other instances, the test sample comprises diseased tissue. The test sample can also be made up of normal and/or diseased cells.

In some embodiments, a reference sample is obtained. The reference sample can be obtained, for example, from the subject and can comprise normal tissue. The reference sample can be also be obtained from a different subject and/or a population of subjects. In some instances, the reference sample is obtained from the subject, a different subject, or a population of subjects before and/or after the peptide or plurality thereof, conjugate or plurality thereof, oligonucleotide or plurality thereof, peptide-based pharmaceutical composition, oligonucleotide-based pharmaceutical composition, vector, cell, or a combination thereof is administered to the subject, and comprises normal tissue. In other instances, the reference sample comprises diseased tissue and is obtained from the subject and/or from a different subject or a population of subjects before and/or after the peptide or plurality thereof, conjugate or plurality thereof, oligonucleotide or plurality thereof, peptide-based pharmaceutical composition, oligonucleotide-based pharmaceutical composition, vector, cell, or a combination thereof is administered to the subject.

In some embodiments, the level of one or more biomarkers is determined in the test sample and/or reference sample. A biomarker can comprise an mRNA expression level (e.g., p53 mRNA level), a protein expression level (e.g., p53 protein level), a modified protein level (e.g., phosphorylated p53 or phosphorylated eIF4E (e.g., p-eIF4E (Ser209)) protein level), or any combination thereof. Non-limiting examples of suitable biomarkers include p53, p21, mouse double minute 2 homolog (MDM2), Puma, and p-eIF4E (e.g., p-eIF4E (Ser209)). Other downstream targets in the p53 pathway are also suitable biomarkers. Typically, the level of the one or more biomarkers in one or more test samples is compared to the level of the one or more biomarkers in one or more reference samples. As a non-limiting example, levels of one or biomarkers in test samples taken before and after the peptide or plurality thereof, conjugate or plurality thereof, oligonucleotide or plurality thereof, peptide-based pharmaceutical composition, oligonucleotide-based pharmaceutical composition, vector, cell, or a combination thereof is administered to the subject are compared to the level of the one or more biomarkers in a reference sample that is either normal tissue obtained from the subject, or normal tissue that is obtained from a different subject or a population of subjects. In some instances, the biomarker is p53 protein, and the level of p53 protein in a test sample obtained from the subject before the peptide or plurality thereof, conjugate or plurality thereof, oligonucleotide or plurality thereof, peptide-based pharmaceutical composition, oligonucleotide-based pharmaceutical composition, vector, cell, or a combination thereof is administered to the subject is lower than the level of p53 in the reference sample. In other instances, the level of p53 protein in a test sample obtained from the subject after administration of the peptide or plurality thereof, conjugate or plurality thereof, oligonucleotide or plurality thereof, peptide-based pharmaceutical composition, oligonucleotide-based pharmaceutical composition, vector, cell, or a combination thereof is increased relative to the level of p53 in a test sample obtained prior to administration. Alternatively, as another non-limiting example, the difference in p53 protein level between a sample obtained from the subject after administration and a reference sample is smaller than a difference between the p53 protein level in a sample obtained from the subject prior to administration and the reference sample (i.e., administration results in an increase in p53 in the test sample such that the difference between the level measured in the test sample and the level measured in the reference sample is diminished or abolished).

In some instances, the biomarker is p-eIF4E (Ser209), and the level of p-eIF4E (Ser209) in a test sample obtained from the subject before the peptide or plurality thereof, conjugate or plurality thereof, oligonucleotide or plurality thereof, peptide-based pharmaceutical composition, oligonucleotide-based pharmaceutical composition, vector, cell, or a combination thereof is administered to the subject is higher than the level of p-eIF4E (Ser209) in the reference sample. In other instances, the level of p-eIF4E (Ser209) in a test sample obtained from the subject after administration of the peptide or plurality thereof, conjugate or plurality thereof, oligonucleotide or plurality thereof, peptide-based pharmaceutical composition, oligonucleotide-based pharmaceutical composition, vector, cell, or a combination thereof is decreased relative to the level of p-eIF4E (Ser209) in a test sample obtained prior to administration. Alternatively, as another non-limiting example, the difference in p-eIF4E (Ser209) level between a sample obtained from the subject after administration and a reference sample is smaller than a difference between the p-eIF4E (Ser209) level in a sample obtained from the subject prior to administration and the reference sample (i.e., administration results in an decrease in p-eIF4E (Ser209) in the test sample such that the difference between the level measured in the test sample and the level measured in the reference sample is diminished or abolished).

The differences between the reference sample or value and the test sample need only be sufficient to be detected. In some embodiments, a decreased level of a biomarker (e.g., p53 protein) in the test sample, and hence the presence of a disease associated with abnormal p53 expression, or the increased risk of such a disease, is determined when the biomarker levels are at least, e.g., about 10%, 25%, 50%, or 75% lower in comparison to a negative control. In other embodiments, an increased level of a biomarker (e.g., p-eIF4E (Ser209)) in the test sample, and hence the presence of a disease associated with abnormal eIF4E phosphorylation, or the increased risk of such a disease, is determined when the biomarker levels are at least, e.g., about 10%, 25%, 50%, or 75% higher in comparison to a negative control.

In some embodiments, administering the peptide or plurality thereof, conjugate or plurality thereof, oligonucleotide or plurality thereof, peptide-based pharmaceutical composition, oligonucleotide-based pharmaceutical composition, vector, cell, or a combination thereof increases the level of a biomarker in a test sample (e.g., a test sample obtained after administration) by at least about 1.1-, 1.2-, 1.3-, 1.4-, 1.5-, 1.6-, 1.7-, 1.8-, 1.9-, 2-, 2.1-, 2.2-, 2.3-, 2.4-, 2.5-, 2.6-, 2.7-, 2.8-, 2.9-, 3-, 3.1-, 3.2-, 3.3-, 3.4-, 3.5-, 3.6-, 3.7-, 3.8-, 3.9-, 4-, 4.1-, 4.2-, 4.3-, 4.4-, 4.5-, 4.6-, 4.7-, 4.8-, 4.9-, 5-, 5.5-, 6-, 6.5-, 7-, 7.5-, 8-, 8.5-, 9-, 9.5-, 10-, 10.5-, 11-, 11.5-, 12-, 12.5-, 13-, 13.5-, 14-, 14.5-, 15-, 15.5-, 16-, 16.5-, 17-, 17.5-, 18-, 18.5-, 19-, 19.5-, or 20-fold compared to a control value (e.g., a value measured or determined in a reference sample or a separate test sample).

In some embodiments, administering the peptide or plurality thereof, conjugate or plurality thereof, oligonucleotide or plurality thereof, peptide-based pharmaceutical composition, oligonucleotide-based pharmaceutical composition, vector, cell, or a combination thereof decreases the level of a biomarker in a test sample (e.g., a test sample obtained after administration) by at least about 1.1-, 1.2-, 1.3-, 1.4-, 1.5-, 1.6-, 1.7-, 1.8-, 1.9-, 2-, 2.1-, 2.2-, 2.3-, 2.4-, 2.5-, 2.6-, 2.7-, 2.8-, 2.9-, 3-, 3.1-, 3.2-, 3.3-, 3.4-, 3.5-, 3.6-, 3.7-, 3.8-, 3.9-, 4-, 4.1-, 4.2-, 4.3-, 4.4-, 4.5-, 4.6-, 4.7-, 4.8-, 4.9-, 5-, 5.5-, 6-, 6.5-, 7-, 7.5-, 8-, 8.5-, 9-, 9.5-, 10-, 10.5-, 11-, 11.5-, 12-, 12.5-, 13-, 13.5-, 14-, 14.5-, 15-, 15.5-, 16-, 16.5-, 17-, 17.5-, 18-, 18.5-, 19-, 19.5-, or 20-fold compared to a control value (e.g., a value measured or determined in a reference sample or a separate test sample).

As described above, the biomarker levels can be detected using any method known in the art, including the use of antibodies specific for the biomarkers. Exemplary methods include, without limitation, Western Blot, dot blot, enzyme-linked immunosorbent assay (ELISA), radioimmunoassay (RIA), immunoprecipitation, RNA-ChIP assay, immunofluorescence, FACS analysis, electrochemiluminescence, and multiplex bead assays (e.g., using Luminex or fluorescent microbeads).

In other embodiments, the methods further comprise the step of providing the diagnosis to the patient (i.e., the subject) and/or the results of treatment.

In some embodiments, the disease associated with abnormal expression and/or activity and/or eIF4E phosphorylation is cancer. In some embodiments, the methods of increasing p53 expression and/or activity and/or decreasing eIF4E phosphorylation in a subject further comprise delivering a chemotherapeutic agent, radiation therapy, or a combination thereof to the subject. In some embodiments, the effect of an anti-cancer agent (e.g., a chemotherapeutic agent) is enhanced by administration of the peptide or plurality thereof, conjugate or plurality thereof, oligonucleotide or plurality thereof, peptide-based pharmaceutical composition, oligonucleotide-based pharmaceutical composition, vector, cell, or a combination thereof. The anti-cancer agent can be, for example, a chemotherapeutic agent such as doxorubicin or etoposide. Examples of suitable chemotherapeutic agents are described in detail above in the section titled "Compositions."

Some non-limiting examples of cancers that are suitable for prevention or treatment by the methods described herein include colorectal cancer, colon cancer, anal cancer, liver cancer, ovarian cancer, breast cancer, lung cancer, bladder cancer, thyroid cancer, pleural cancer, pancreatic cancer, cervical cancer, prostate cancer, testicular cancer, bile duct cancer, gastrointestinal carcinoid tumors, esophageal cancer, gall bladder cancer, rectal cancer, appendix cancer, small intestine cancer, stomach (gastric) cancer, renal cancer (i.e., renal cell carcinoma), cancer of the central nervous system, skin cancer, oral squamous cell carcinoma, choriocarcinomas, head and neck cancers, bone cancer, osteogenic sarcomas, fibrosarcoma, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma.

IV. Examples

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1. Induction of p53 and Downstream Targets

This example shows that peptides and oligonucleotides of the present invention were able to induce p53 and downstream targets, as well as inhibit colony formation by cancer cells.

Introduction

The p53 tumor suppressor plays a pivotal role in maintaining genome integrity, and inactivation of the p53 pathway is found in more than 50% of human cancers. Based on the discovery that the RNA-binding protein RBM38, also called RNPC1, is a target of the p53 family and that RBM38 can in turn repress p53 translation via interacting with eIF4E, peptides and oligonucleotides were designed that disrupt interactions between RBM38 and eIF4E, thus improving p53 translation and protein expression. As shown herein, peptides and oligonucleotides of the present invention successfully enhanced p53 activity, including induction of downstream p53 targets, and inhibited the growth of cancer cells.

Methods
Peptides for p53 Expression Enhancement and Cancer Cell Inhibition

Figure 1A:
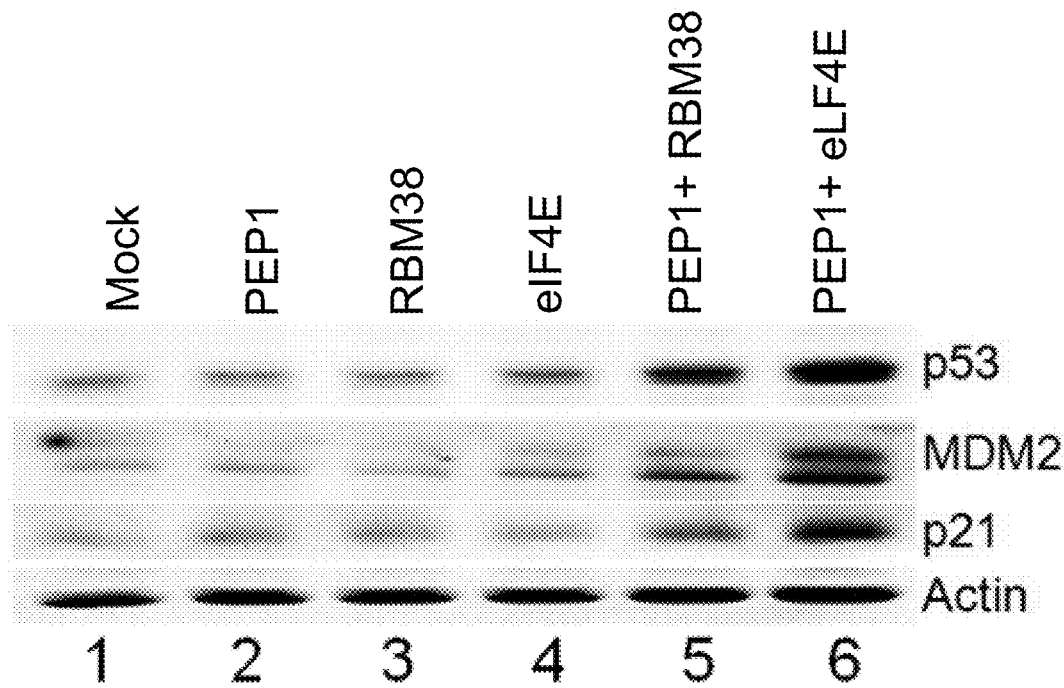
FIGS. 1A-1F show that peptides of the present invention induced p53 and downstream targets and inhibited cancer cell colony formation.

Peptides of the present invention were tested for their ability to enhance the expression of p53 and downstream targets in cancer cells. For these experiments, MCF7 breast cancer cells were seeded at a density of $1\times10^4$ cells per well in 12-well plates. The following day cells were treated with the peptides RBM38 (SEQ ID NO:2) and eIF4E (SEQ ID NO:3). In order to form stable complexes of the peptides with PEP1 (a cell-penetrating peptide; SEQ ID NO:13), 100 μL of serum-free DMEM was added to individual Eppendorf tubes. For PEP1 alone, 6 μg was added. RBM38 and eIF4E alone were added at a concentration of 300 nM. For PEP1+ peptide, peptide at a concentration of 300 nM was added to 6 μg PEP1 (20:1 PEP1 to peptide). All peptides were incubated at room temperature for 20 minutes before being added dropwise to the cells for 18 hours. Cells were then lysed using 100 μL SDS-lysis buffer and the lysate was then run on a 12% SDS-PAGE gel, followed by transfer to a nitrocellulose membrane and incubation with antibodies specific for p53, MDM2, p21, and actin. As shown in FIG. 1A, treating the cells with either RBM38 or eIF4E in combination with PEP1 resulted in increased protein expression of p53 and the downstream targets p21 and mouse double minute 2 homolog (MDM2).

Figure 1B:
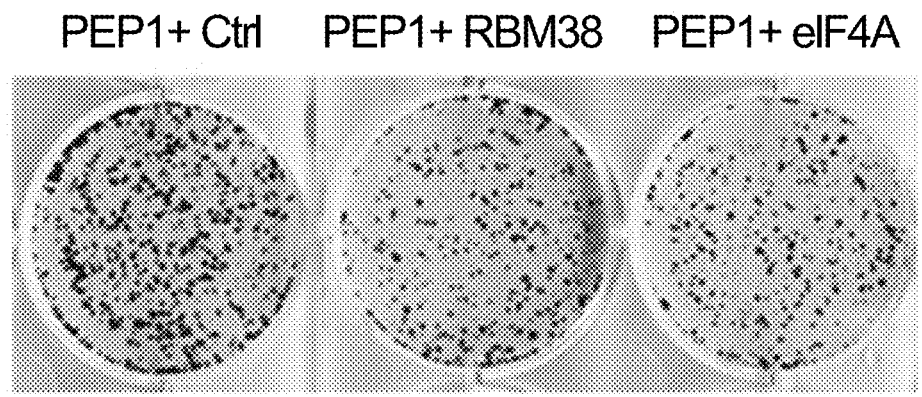

In order to test the effect of the RBM38 and eIF4E peptides on cancer cell colony formation, MCF7 cells were seeded in 6-well plates at a density of $1\times10^3$ cells per well. The following day, cells were treated with peptides. In order to form stable complexes with PEP1, 100 μl of serum-free DMEM was added to individual Eppendorf tubes. Control (SEQ ID NO:11), RBM38, and eIF4E peptides were added at a concentration of 375 nM and then 7.5 μg of PEP1 was added to each peptide (20:1). The complexes were incubated for 20 minutes at room temperature and then added dropwise to cells. Cell media was changed every three days until colonies were visible. The cells were fixed and then stained with crystal violet. As shown in FIG. 1B, either RBM38 or eIF4E in combination with PEP1 was able to inhibit MCF7 cell colony formation.

Figure 1C:
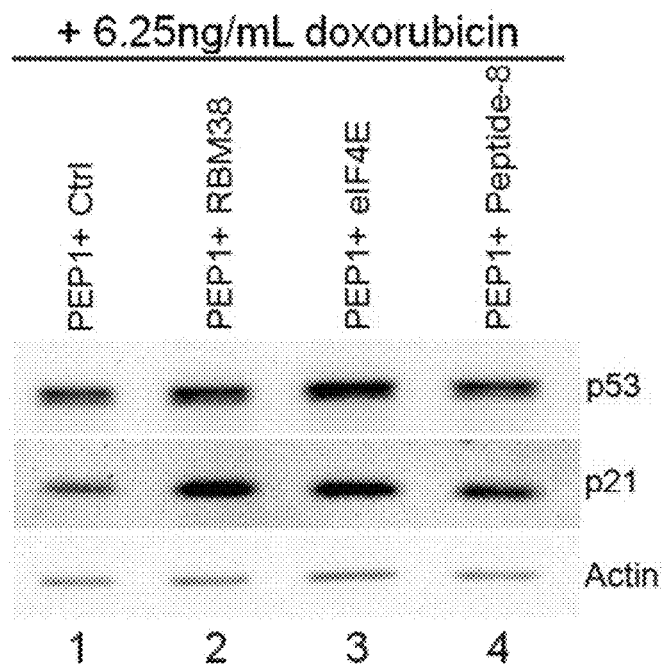

Further experiments were performed in order to assess the effect of peptides of the present invention when combined with a chemotherapeutic agent. For these experiments, MCF7 cells were seeded at a density of $1\times10^4$ cells per well in 12-well plates. The following day, cells were treated with peptides. In order to form stable complexes with PEP1, 100 μL of serum free DMEM was added to individual Eppendorf tubes. Control, RBM38, eIF4E, and peptide-8 (SEQ ID NO:1) peptides were added at a concentration of 375 nM and then 7.5 μg of PEP1 was added to each peptide (20:1). The complexes were incubated for 20 minutes at room temperature and then added dropwise to cells. 20 minutes after addition of peptide complexes, 6.25 ng/mL doxorubicin was added to the cells. Cells were lysed 18 hours later using 100 μL SDS-lysis buffer and the lysate was run on a 12% SDS-PAGE gel, followed by transfer to a nitrocellulose membrane and incubation with antibodies specific for p53, p21, and actin. As shown in FIG. 1C, RBM38, eIF4E, and peptide-8 (in complex with PEP1) enhanced the effect of doxorubicin-mediated p53 and p21 upregulation in MCF7 cells.

In order to test the effect of a combination treatment comprising peptides of the present invention and a chemotherapeutic agent on cancer cell colony formation, MCF7 cells were seeded in 6-well plates at a density of $1\times10^3$ cells per well. The following day, cells were treated with peptides. In order to form stable complexes with PEP1, 100 μL of serum-free DMEM was added to individual Eppendorf tubes. Control, RBM38, eIF4E, and peptide-8 peptides were added at a concentration of 375 nM and then 7.5 μg of PEP1 was added to each peptide (20:1). The complexes were incubated for 20 minutes at room temperature and then added dropwise to cells. 20 minutes after addition of peptide complexes, 3.125 ng/mL doxorubicin was added to the cells.

Figure 1D:
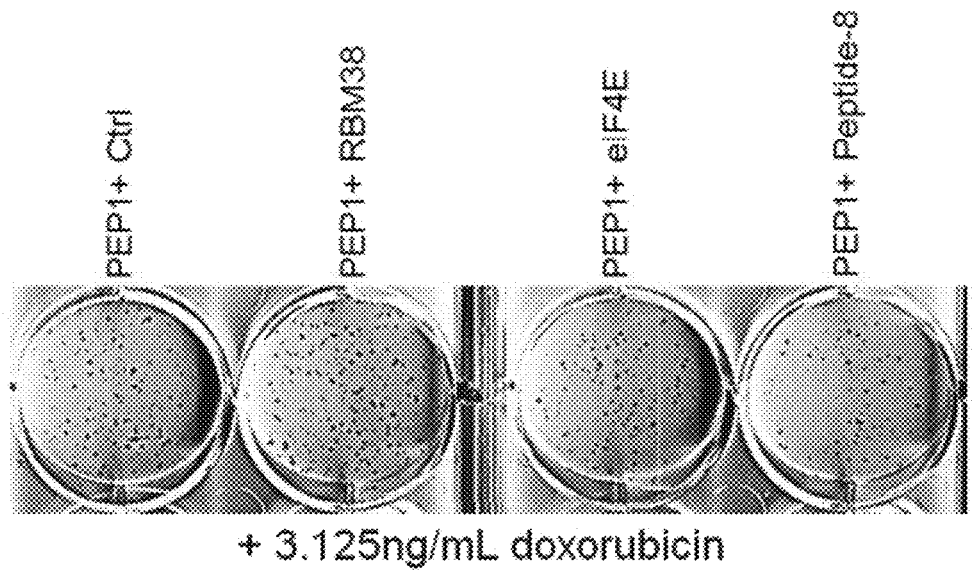

Cell media was changed every three days until colonies were visible. The cells were fixed and then stained with crystal violet. As shown in FIG. 1D, RBM38, eIF4E, and peptide-8 (in complex with PEP1) enhanced the inhibition of colony formation by low-dose doxorubicin in MCF7 cells.

Figure 1E:
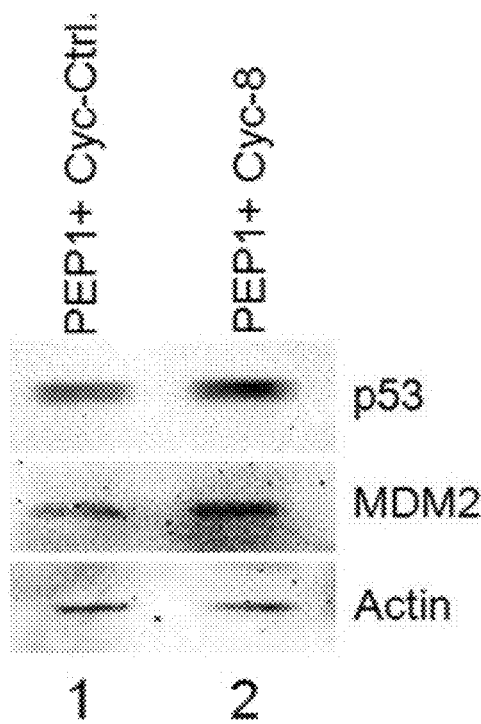
Figure 1F:
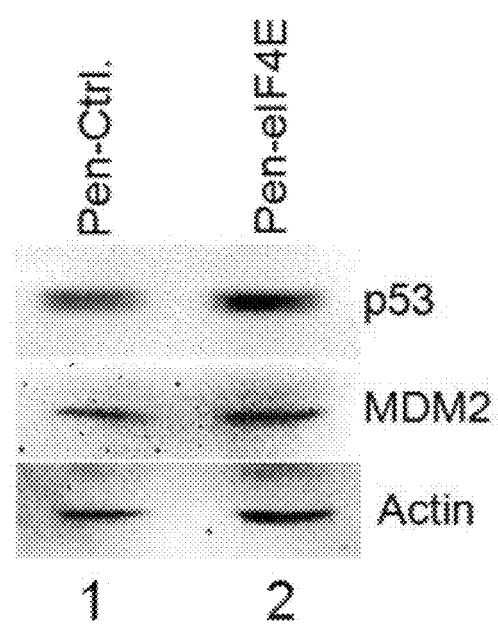

The effects of cyclic peptide-8 (Cyc-8; SEQ ID NO:5) and eIF4E (which was fused to the cell-penetrating peptide Penetratin™ (Pen-eIF4E; SEQ ID NO:9)) were tested in RKO cancer cells. For these experiments, RKO cells were seeded at a density of $1 \times 10^4$ cells per well in 12-well plates. The following day, cells were treated with peptides. To form stable complexes with PEP1, 100 µL of serum-free DMEM was added to individual Eppendorf tubes. Cyc-control or Cyc-8 peptides were added at a concentration of 375 nM and then 7.5 µg of PEP1 was added to each peptide (20:1). The complexes were incubated for 20 minutes at room temperature and then added dropwise to cells. Pen-Control (SEQ ID NO:10) and Pen-eIF4E were added at a concentration of 5 µM. Cells were lysed 18 hours later using 100 µL SDS-lysis buffer and the lysate was run on a 12% SDS-PAGE gel, followed by transfer to a nitrocellulose membrane and incubation with antibodies specific for p53, MDM2, and actin. As shown in FIGS. 1E and 1F, both Cyc-8 and Pen-eIF4E enhanced the protein expression of p53 and the downstream target MDM2.

Oligonucleotides for p53 Expression Enhancement

Figure 2:
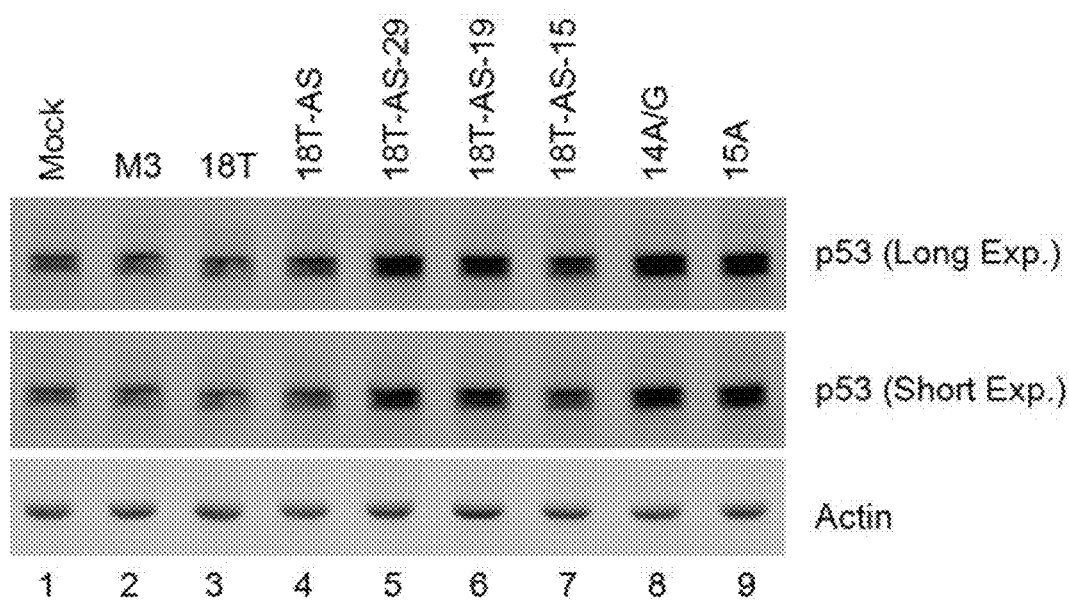
FIG. 2 shows that the level of p53 was increased in MCF7 cells upon treatment with the oligonucleotide 18T-AS (SEQ ID NO:16) and shortened oligonucleotides of 18T-AS (18T-AS-29 (SEQ ID NO:17), 18T-AS-19 (SEQ ID NO:18), 18T-AS-15 (SEQ ID NO:19), 14A/G (SEQ ID NO:20), and 15A (SEQ ID NO:21)), but not in MCF7 cells mock-treated or treated with control oligonucleotides (M3 (SEQ ID NO:14) and 18T (SEQ ID NO:15)). MCF7 cells were mock-treated or treated with various oligonucleotides (50 nM) for 24 hours, followed by Western blot with antibody against p53 or actin.

In addition, oligonucleotides of the present invention were tested for their ability to enhance p53 expression in cancer cells. For these experiments, MCF7 cells were seeded at a density of $1 \times 10^4$ cells per well in 12-well plates. The following day, cells were treated with the oligonucleotides (18T-AS (SEQ ID NO:16), 18T-AS-29 (SEQ ID NO:17), 18T-AS-19 (SEQ ID NO:18), 18T-AS-15 (SEQ ID NO:19), 14A/G (SEQ ID NO:20), 15A (SEQ ID NO:21), M3 (SEQ ID NO:14), or 18T (SEQ ID NO:15)). MCF7 cells were either mock-treated or treated with the indicated oligonucleotides (50 nM) for 24 hours. Cells where then lysed using 100 µL SDS-lysis buffer and the lysate was run on a 12% SDS-PAGE gel, followed by transfer to a nitrocellulose membrane and incubation with antibodies specific for p53 and actin. As shown in FIG. 2, the level of p53 was increased in MCF7 cells upon treatment with the oligonucleotide 18T-AS or one of the shortened oligonucleotides of 18T-AS (18T-AS-29, 18T-AS-19, 18T-AS-15, 14A/G, and 15A), but not in MCF7 cells that were mock-treated or treated with control oligonucleotides (M3 and 18T).

Discussion

As shown here, synthetic peptides of the present invention were used to treat human cancer cells with or without the addition of genotoxic stress. In addition to increasing p53 protein levels, both the RBM38 and eIF4E peptides were able to suppress colony formation of MCF7 breast cancer cells. Surprisingly, each peptide (RBM38, eIF4E, and peptide-8) was further able to enhance the induction of p53 and p21 in MCF7 cells treated with low-dose doxorubicin. Beyond inducing p53 and p21 protein levels, both eIF4E and peptide-8, with the addition of low-dose doxorubicin, led to decreased colony formation. Furthermore, it was shown that a cyclized version of peptide-8 was able to increase p53 protein expression. In addition, it was shown that oligonucleotides of the present invention were able to induce p53 in human cancer cells.

Example 2. Design of Peptides and Oligonucleotides and Demonstration of Effectiveness This example describes the design of peptides and oligonucleotides of the present invention and demonstrates their usefulness in increasing p53 expression and inhibition of cancer cell growth.

Small Peptides to Block the Interaction Between RBM38 and eIF4E

Figure 9:
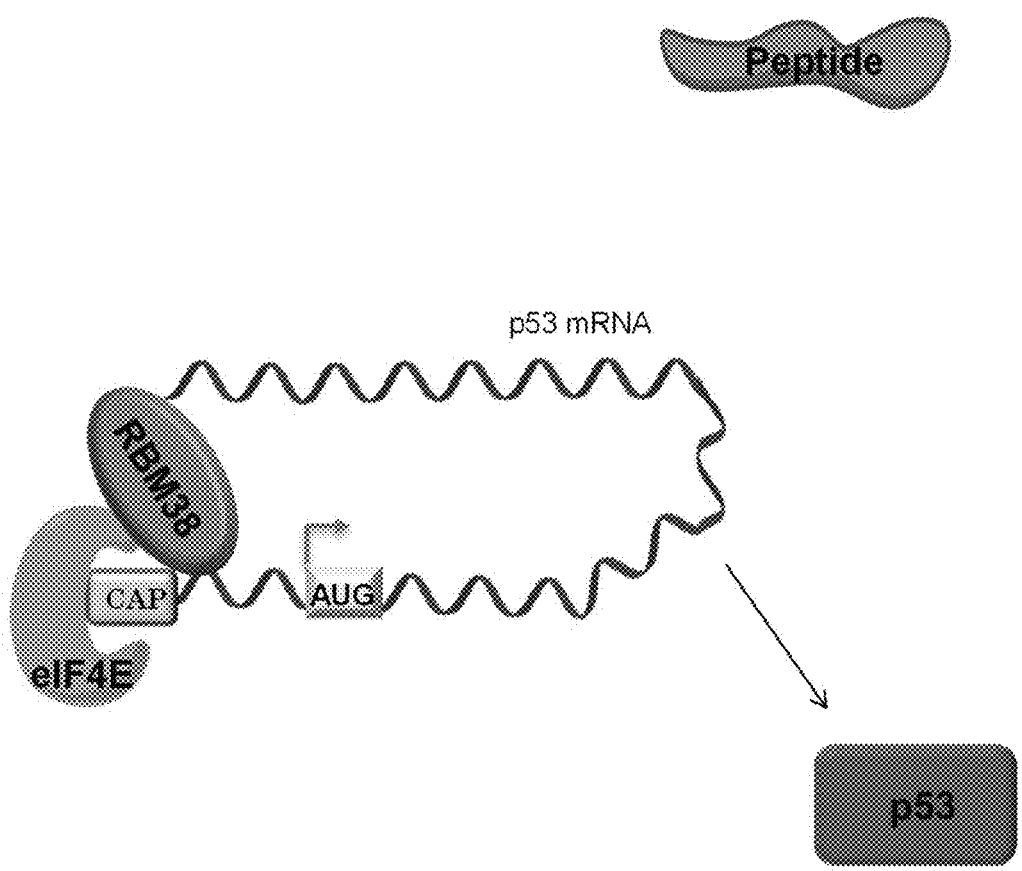
FIG. 9 shows a schematic depicting a strategy to modulate p53 translation by blocking RBM38 inhibition.

One approach to stabilizing translation and inducing expression of p53 and downstream targets is to design small peptides that block RBM38 inhibition of p53 translation (FIG. 9). In particular, peptides that disrupt the interaction between RBM38 and eIF4E can allow eIF4E to interact with p53 mRNA, permitting translation of p53 to occur.

Figure 10A:
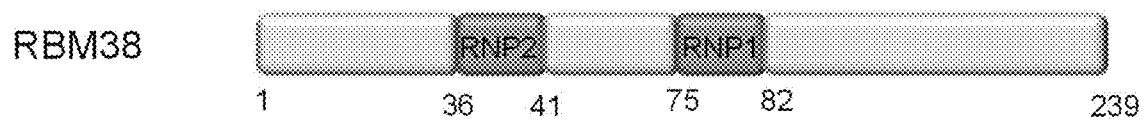
FIGS. 10A and 10B show schematics of RBM38 and eIF4E.
Figure 10B:
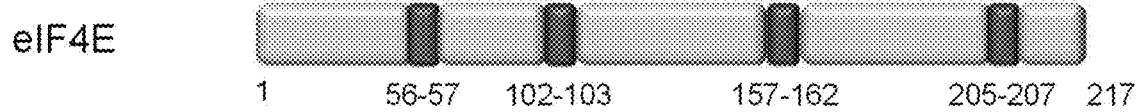
Figure 11A:
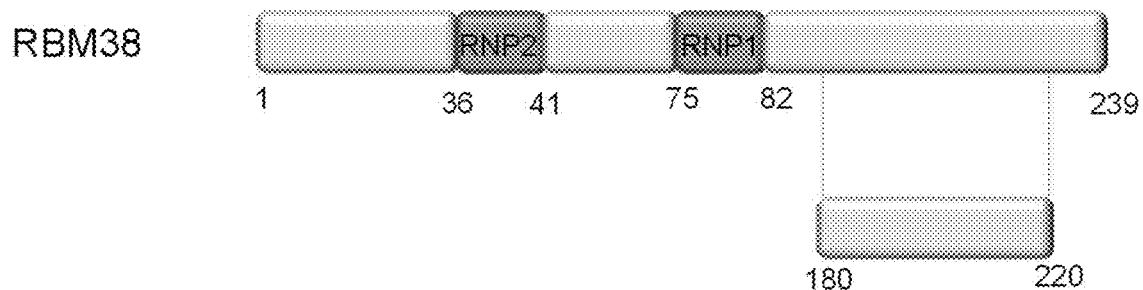
FIGS. 11A and 11B show schematics of RBM38 and eIF4E and mapped binding interfaces.
Figure 11B:
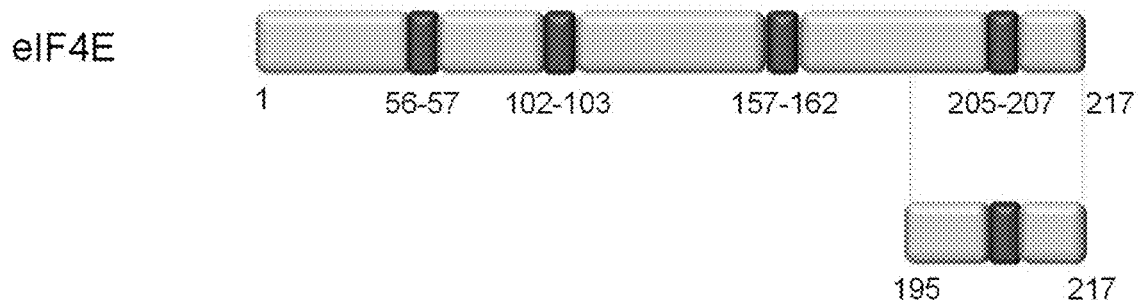
Figures 12A, 12B:
FIGS. 12A and 12B show schematics of RBM38 and eIF4E peptides.

Schematic representations of RBM38 and eIF4E are shown in FIGS. 10A and 10B, respectively. The binding interface between these two proteins was mapped to amino acids 180-220 of RBM38 (FIG. 11A) and amino acids 195-217 of eIF4E (FIG. 11B). The sequences of the binding interfaces were determined to be SEQ ID NO:2 for RBM38 (FIG. 12A) and SEQ ID NO:3 for eIF4E (FIG. 12B).

Figure 13A:
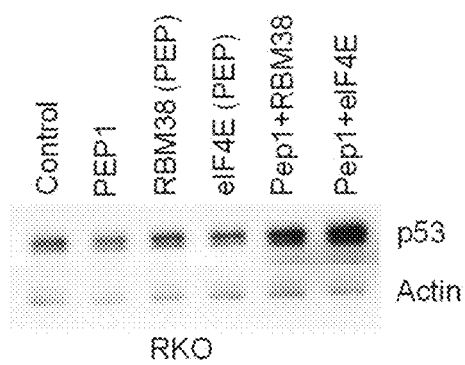
FIGS. 13A-13C show that RBM38 and eIF4E peptides induce p53 expression.
Figure 13B:
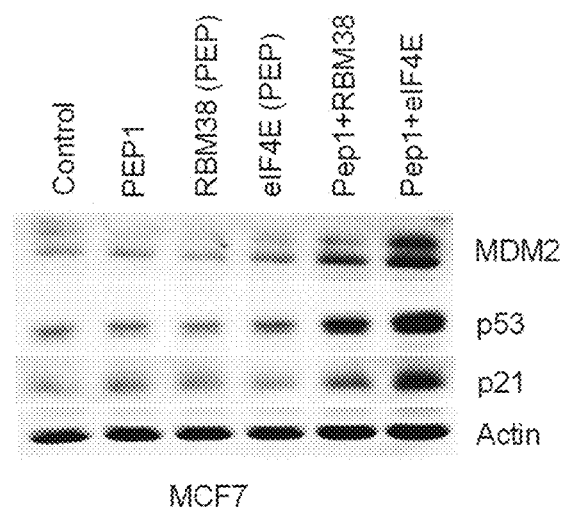
Figure 13C:
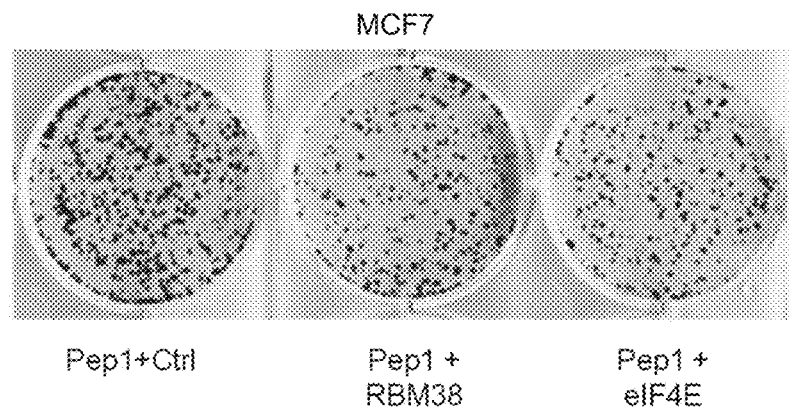

When the peptides RBM38 (SEQ ID NO:2) and eIF4E (SEQ ID NO:3) were complexed with the cell-penetrating peptide PEP1 (SEQ ID NO:13) and used to treat RKO cells, the expression of p53 was increased relative to controls (FIG. 13A). Similarly, when complexes of RBM38 and eIF4E with PEP1 were used to treat MCF7 cells, the expression of p53 and downstream targets p21 and MDM2 was increased (FIG. 13B). The complexes of RBM38 and eIF4E with PEP1 were also successful at inhibiting tumor cell colony formation (FIG. 13C).

Figure 14:
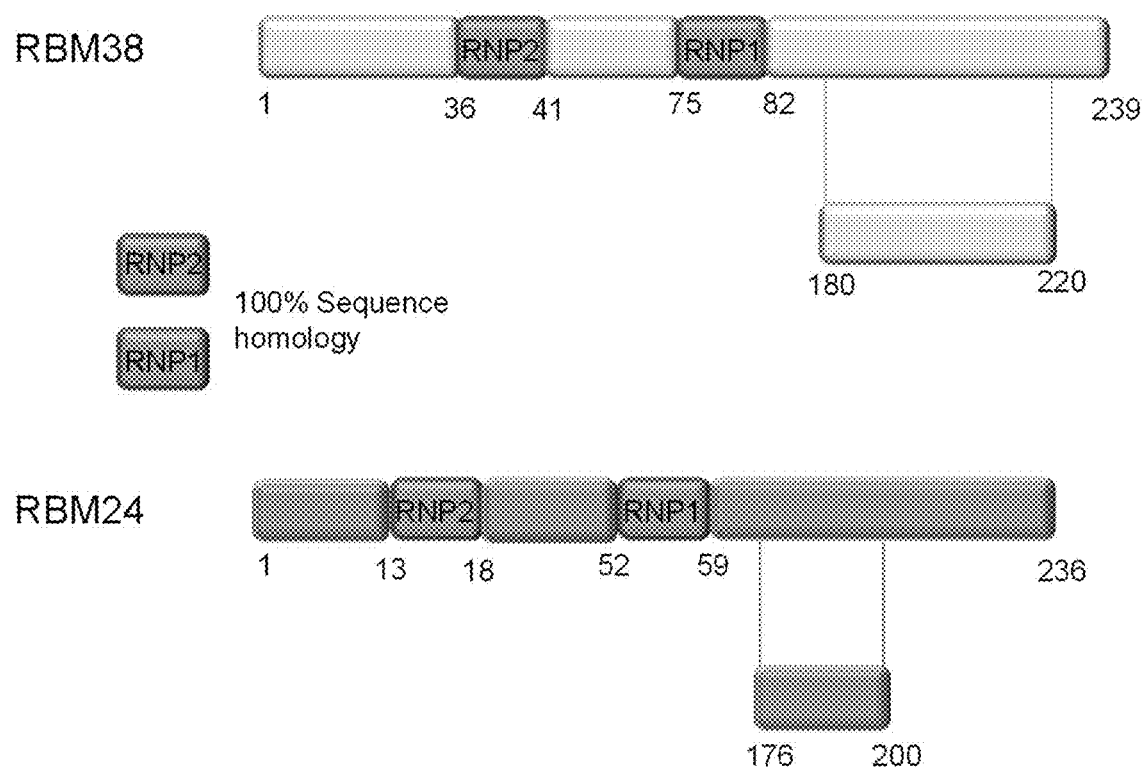
FIG. 14 shows schematics of RBM38 and RBM24 peptides showing that the two genes are highly homologous.
Figure 15A:
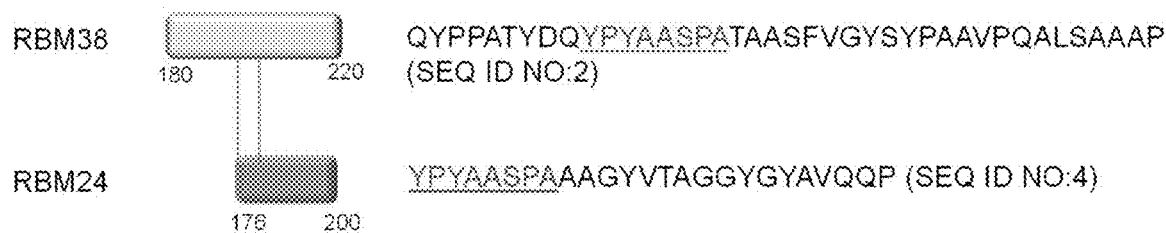
FIGS. 15A-15C show that RBM38 and RBM24 share common interactions with eIF4E.
Figure 15B:
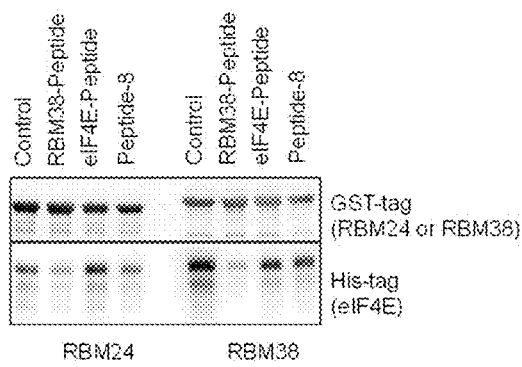
Figure 15C:
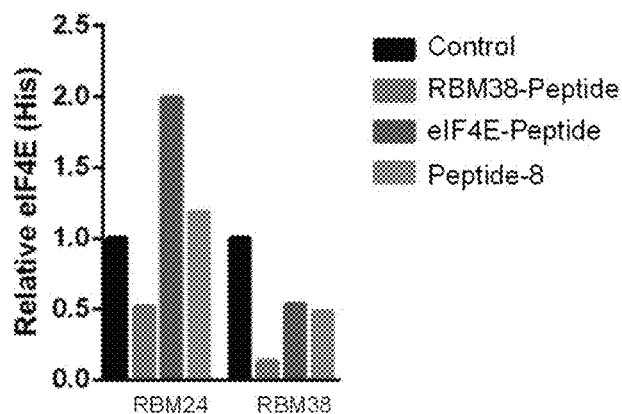
Figure 16A:
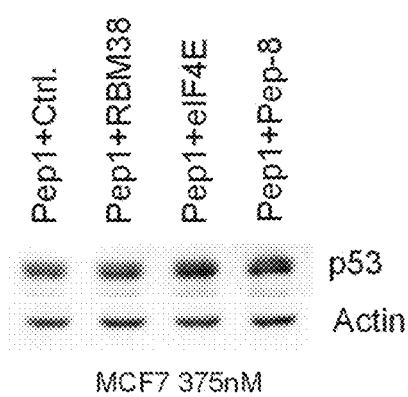
FIGS. 16A-16D show that peptide-8 increases p53 expression.
Figure 16B:
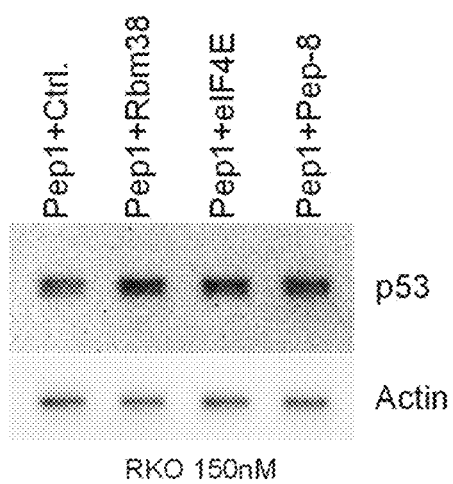
Figure 16C:
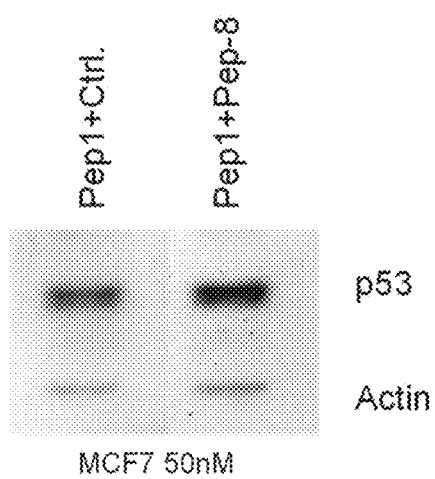
Figure 16D:
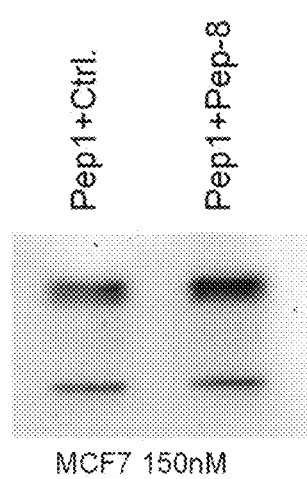
Figure 17A:
Figure 17B:
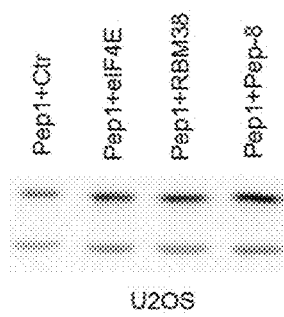
Figure 17C:
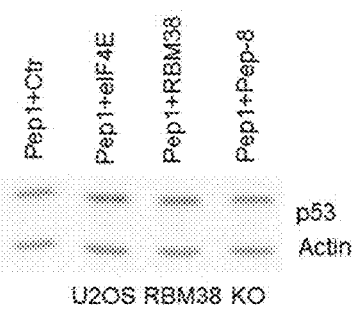
Figure 17D:
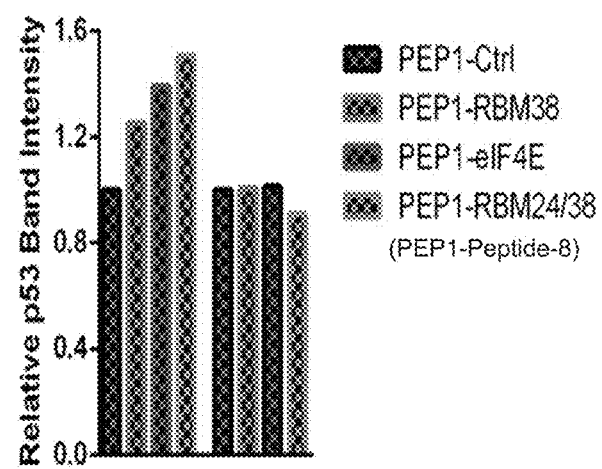

RBM38 and RBM24 are highly homologous genes. FIG. 14, depicts schematics of RBM38 and RBM24, of which amino acids 180-220 of RBM38 (SEQ ID NO:2) and amino acids 176-200 of RBM24 (SEQ ID NO:4) serve as binding interfaces with eIF4E. As shown in FIG. 15A, these two binding interface sequences share eight contiguous amino acids that are identical to each other (SEQ ID NO:1). FIGS. 15B and 15C show relative binding data for the RBM38, eIF4E and peptide-8 (SEQ ID NO:1) peptides.

FIG. 16 shows that at least in some instances, peptide-8 produces a stronger induction of p53 than the longer RBM38 and eIF4E peptides. FIGS. 16A, 16C, and 16D show p53 expression in MCF7 cells that were treated with 375 nM, 50 nM, or 150 nM of the peptides, respectively. FIG. 16B shows p53 expression in RKO cells that were treated with 150 nM of the peptides. FIG. 17 provides data demonstrating RBM38 specificity, utilizing U20S bone osteosarcoma cells and MCF7 breast cancer cells, with and without RBM38 knockout.

Figure 18:
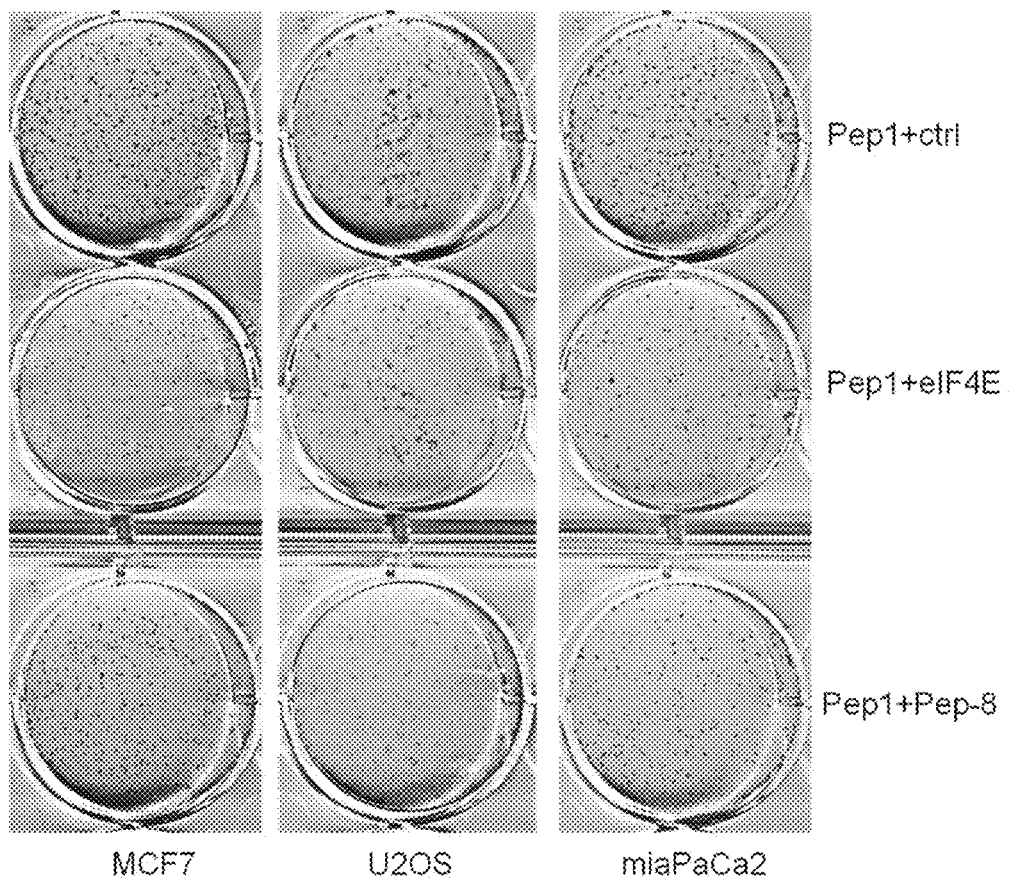
FIG. 18 shows that peptides of the present invention inhibit cancer cell colony formation.

As shown in FIG. 18, complexes of the eIF4E and peptide-8 peptides and PEP1 inhibited colony formation in MCF7, U20S, and MIA-PaCa-2 pancreatic cancer cells.

Figure 19A:
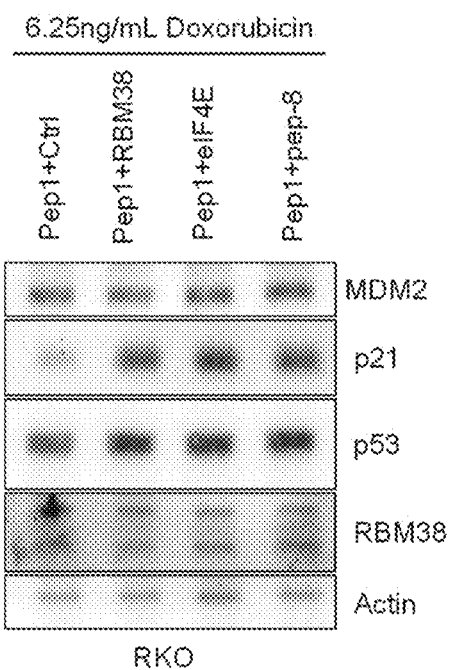
FIGS. 19A and 19B show that a combination of peptides of the present invention and low-dose doxorubicin enhance p53 and p21 regulation.
Figure 19B:
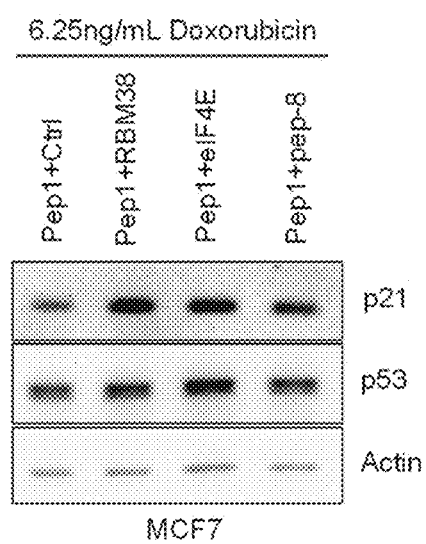
Figure 20A:
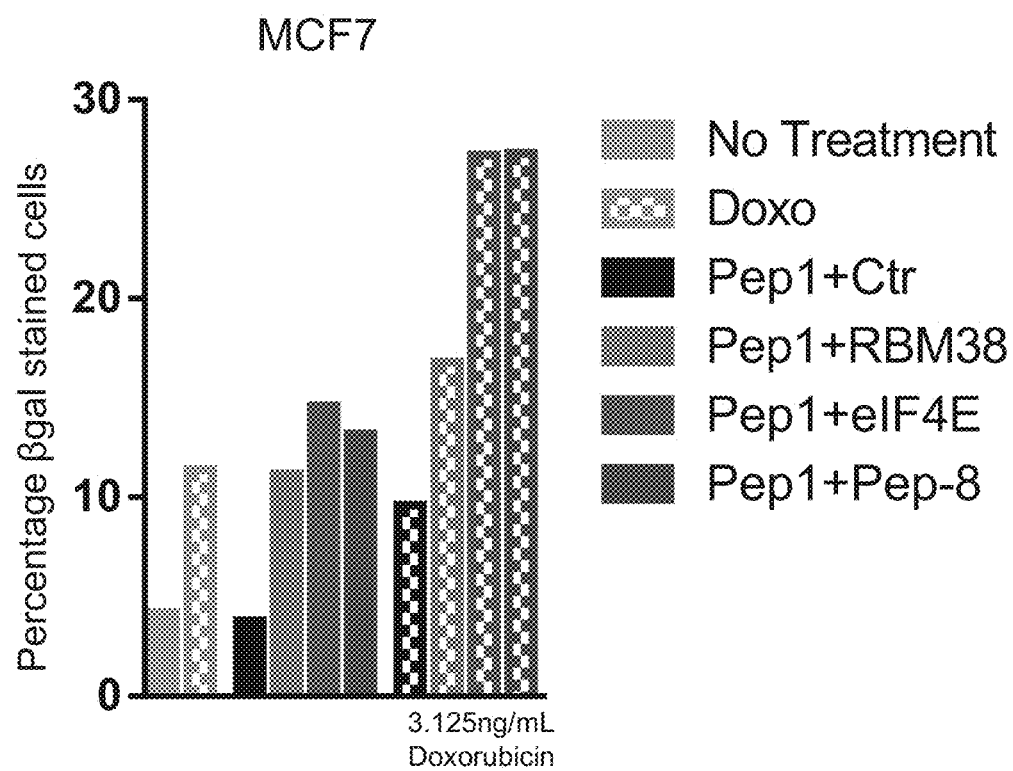
FIGS. 20A-20D show that a combination of peptides of the present invention and doxorubicin produce synergistic effects.
Figure 20B:
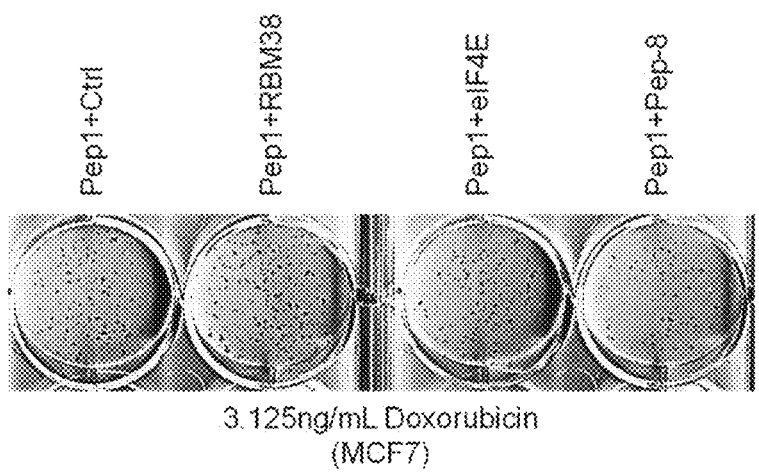
Figure 20C:
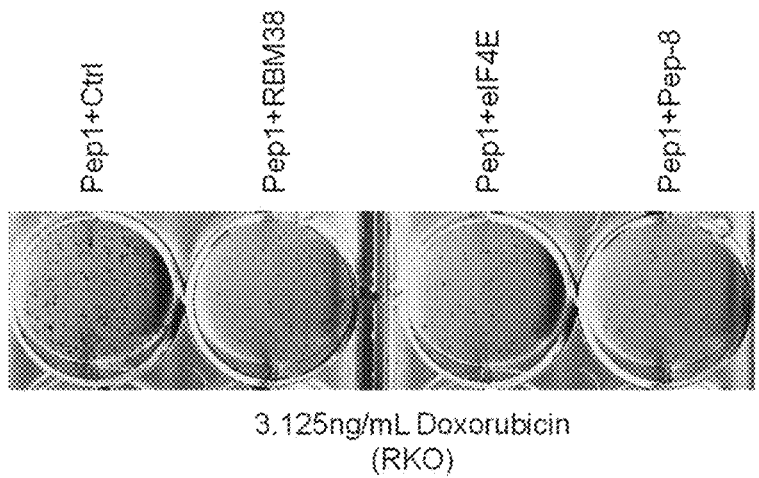
Figure 20D:
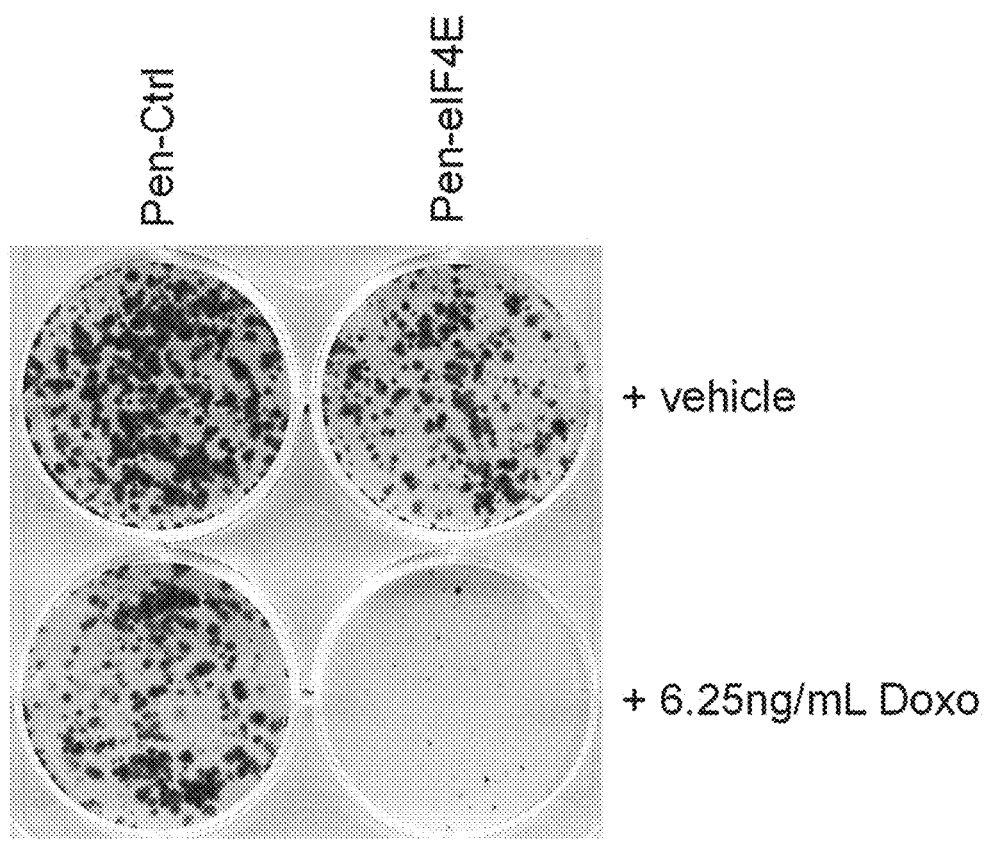

Surprisingly, it was discovered that the peptides exhibit a synergistic effect when combined with the chemotherapeutic agent doxorubicin (a topoisomerase inhibitor). Low-dose doxorubicin (6.25 ng/mL) in conjunction with complexes of CPPs and RBM38, eIF4E or peptide-8 increased the expression of p53 and downstream targets in RKO cells and MCF7 cells (FIGS. 19A and 19B, respectively). Inhibition of cell colony formation is demonstrated in FIGS. 20B, 20C, and 20D. FIG. 20A presents comparisons between using only the peptides, complexed with PEP1, and using the peptides (complexed with PEP1) plus low-dose doxorubicin (3.12 ng/mL). FIG. 20D shows a striking synergistic effect when Pen-eIF4E was combined with doxorubicin.

Figure 21:
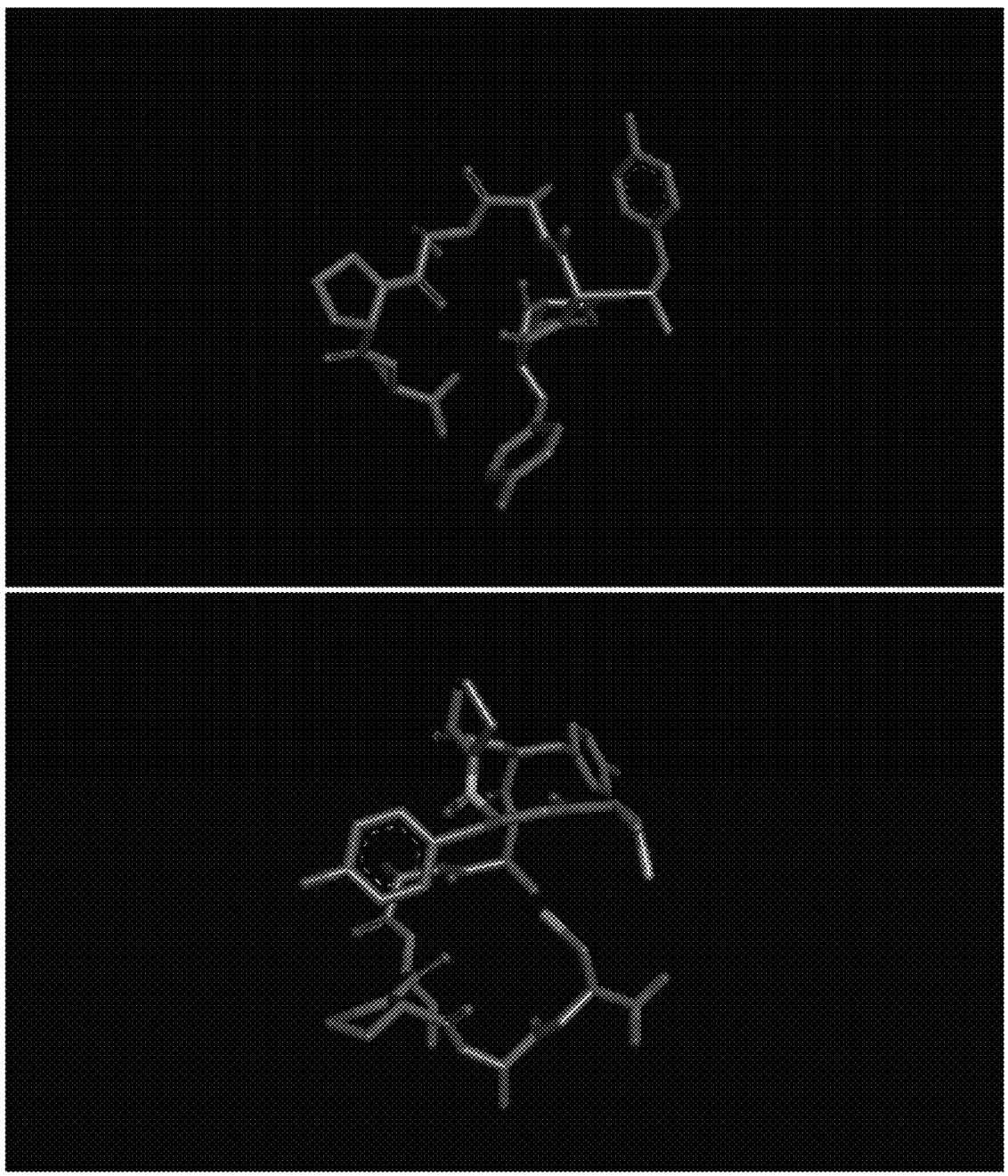
FIG. 21 shows three-dimensional structures of linear (top) and cyclic (bottom) peptide-8.
Figure 22:
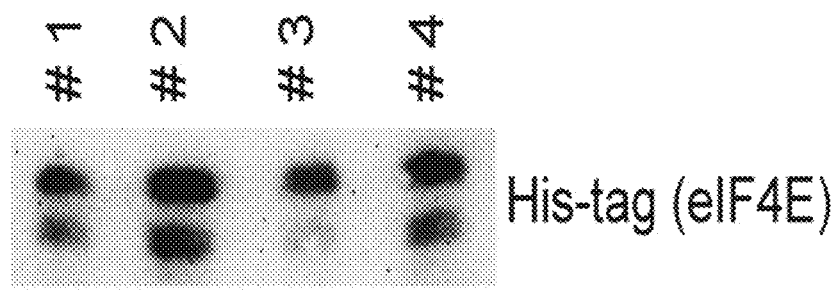
FIG. 22 shows a Western blot for a pulldown assay showing which peptide bound more His-eIF4E. The peptides bound to Tentagel™ resin were incubated with His-eIF4E overnight and then washed extensively before being eluted with SDS-PAGE lysis buffer followed by Western blot assay for His-eIF4E. Lane #1: peptide-8 (SEQ ID NO:1); Lane #2: Cyc-8 peptide (SEQ ID NO:5); Lane #3: kAmi-8 peptide (SEQ ID NO:8); Lane #4: Ami-8 peptide (SEQ ID NO:7).
Figure 23A:
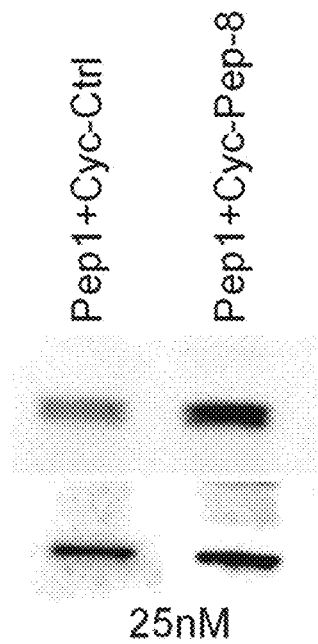
FIGS. 23A-23E show that cyclic peptides demonstrate some advantages over linear peptides.
Figure 23B:
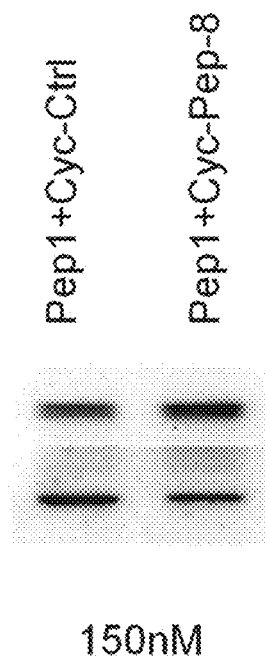
Figure 23C:
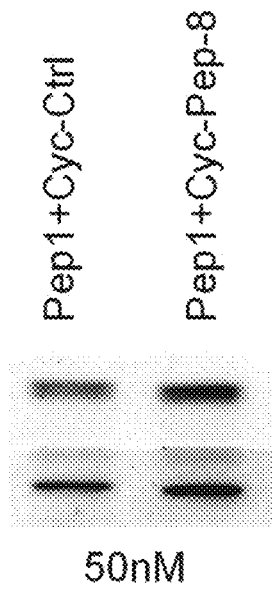
Figure 23D:
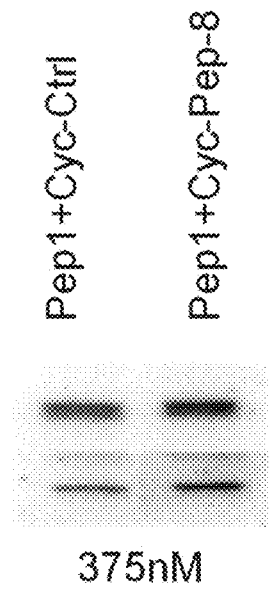
Figure 23E:
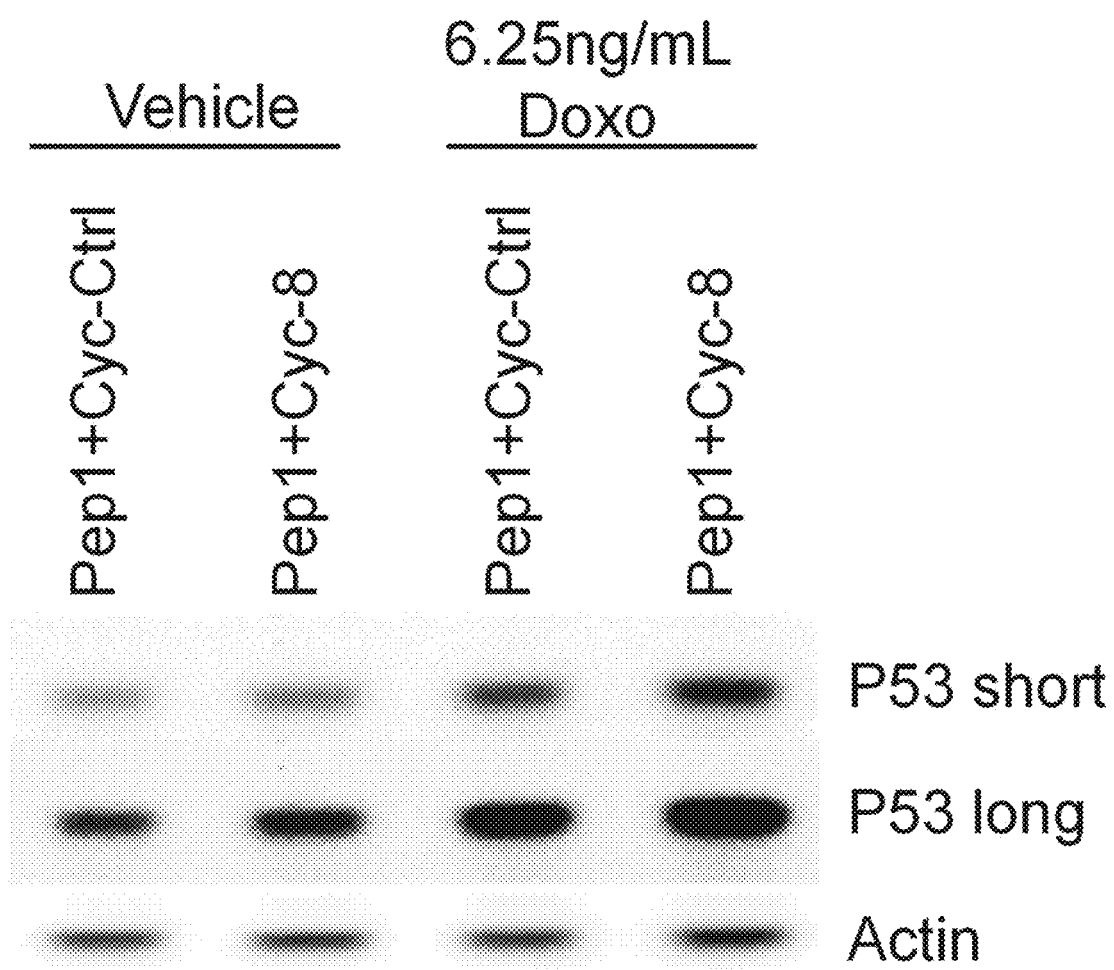
Figure 24A:
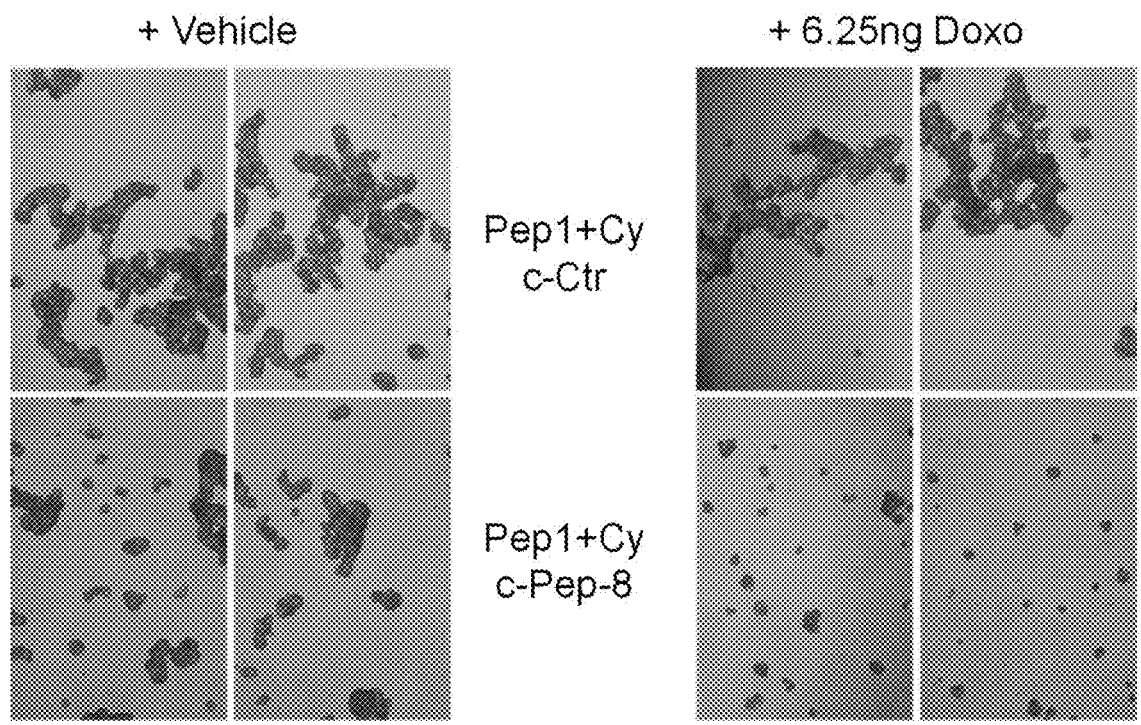
FIGS. 24A and 24B show that a combination of cyclic peptides of the present invention and low-dose doxorubicin reduce tumor sphere formation.
Figure 24B:
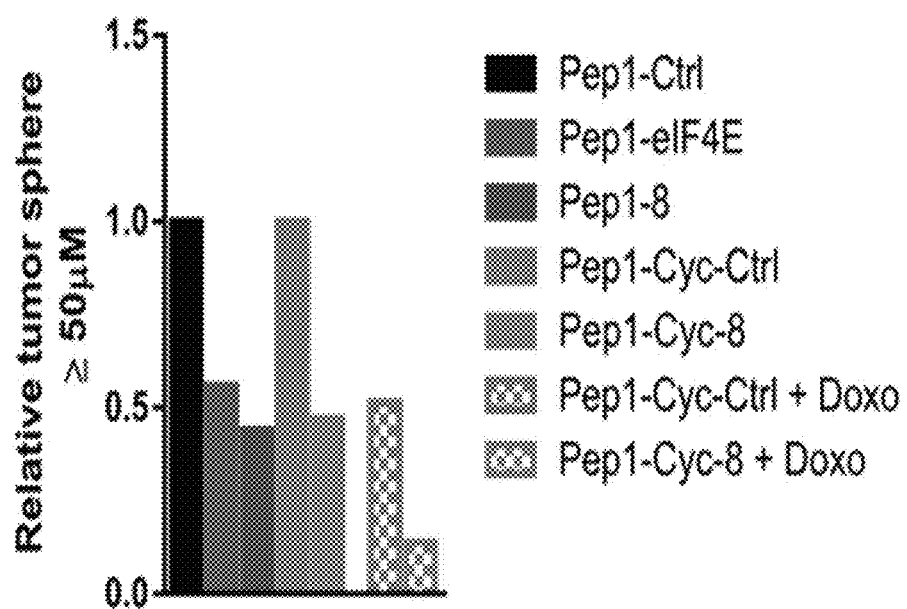

Next, it was explored whether cyclized versions of the peptides improved effectiveness (FIG. 21). As shown in FIG. 22, several cyclic variants of peptide-8 were tested: a disulfide cyclic 10-mer of peptide-8 (SEQ ID NO:5), an amide bond cyclic 10-mer of peptide-8 (SEQ ID NO:8) wherein the side chains of a lysine and D-glutamic acid form an amide bond), and an amide bond cyclic 9-mer of peptide-8 (SEQ ID NO:7) wherein the N-terminal amino group and a D-glutamic acid side chain form an amide bond. As shown in FIG. 23, the cyclized peptide-8 produced a stronger upregulation of p53 at several different peptide concentrations (FIGS. 23A-23D), and similarly produced a stronger effect in combination with low-dose doxorubicin (FIG. 23E). Similar results were observed with respect to tumor sphere formation (FIG. 24).

Figure 25:
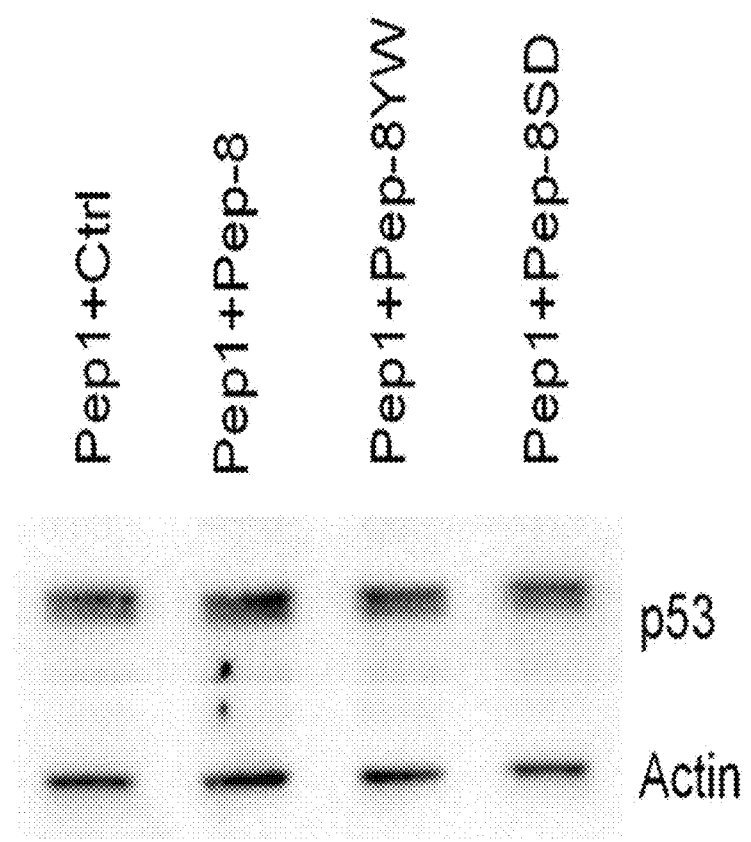
FIG. 25 shows p53 and actin control expression data in response to treatment with indicated peptides. PEP1 (SEQ ID NO:13) was complexed with control (SEQ ID NO:11), peptide-8 (SEQ ID NO:1), peptide-8YW (SEQ ID NO:43), or peptide-8-SD (SEQ ID NO:44).

FIG. 25 shows the effects of substituting amino acids at two different positions within peptide-8. The cell-penetrating peptide PEP1 (SEQ ID NO:13) was complexed with a control peptide (SEQ ID NO:11), peptide-8 (SEQ ID NO:1), peptide-8YW (SEQ ID NO:43), or peptide-8SD (SEQ ID NO:44). p53 expression was determined using Western blot.

Oligonucleotides to Block the Interaction Between RBM38 and the p53 3' UTR

Figure 26:
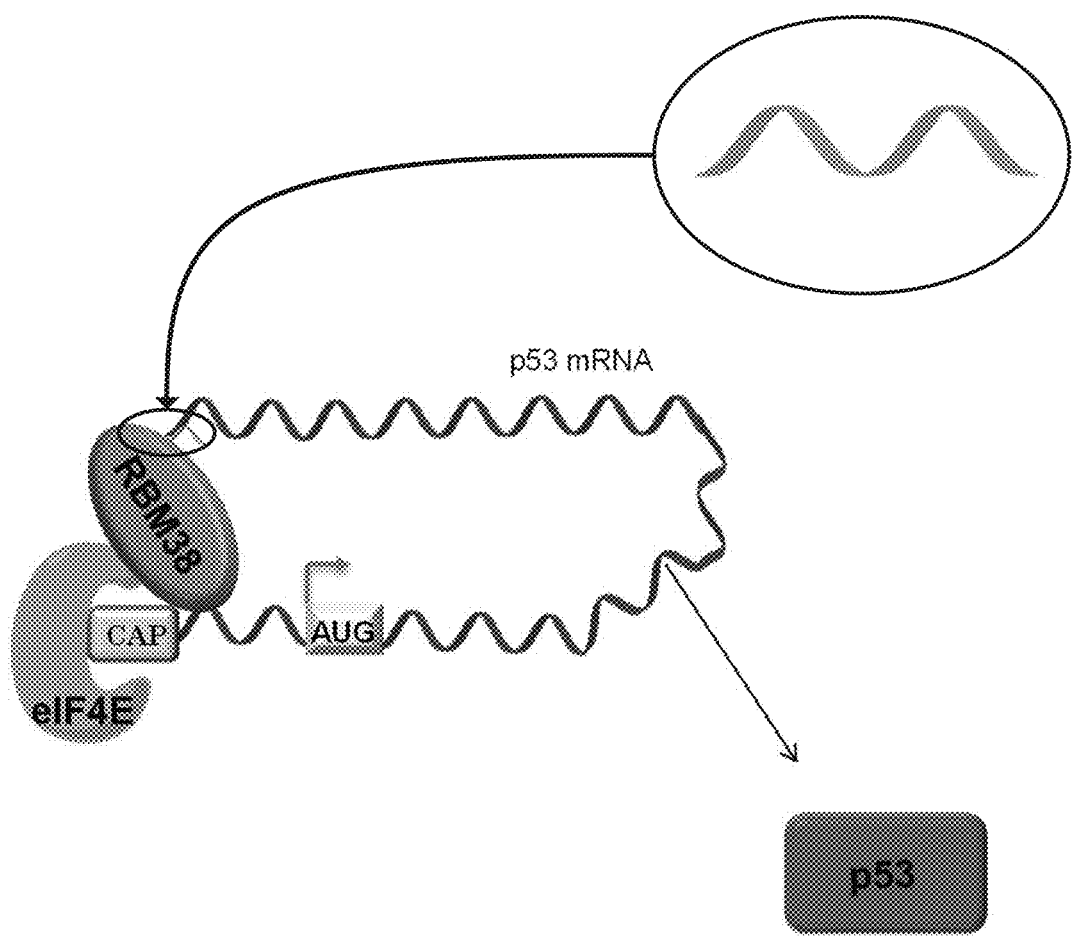
FIG. 26 shows a schematic of a strategy wherein oligonucleotides of the present invention are used to block the interaction between RBM38 and the p53 3' UTR, thus allowing translation of p53 mRNA.
Figure 28A:
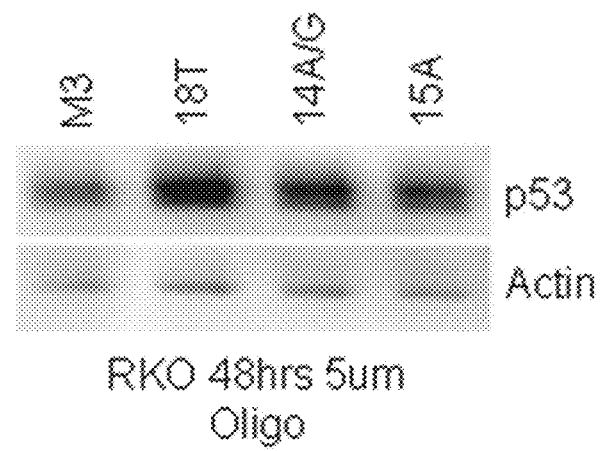
FIGS. 28A-28C show the effects of oligonucleotides of the present invention on p53 expression.
Figure 28B:
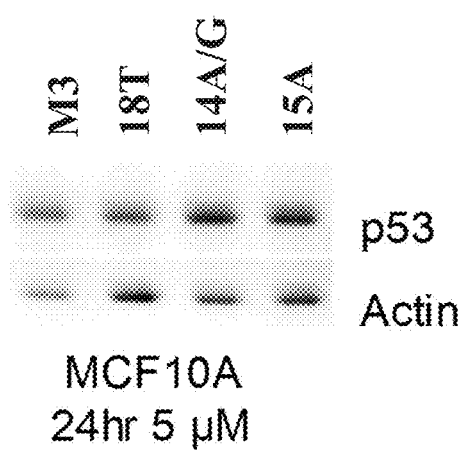
Figure 28C:
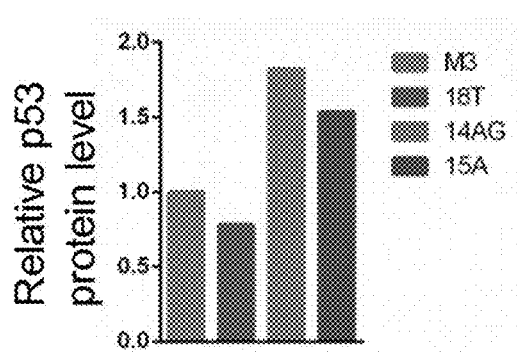
Figure 30:
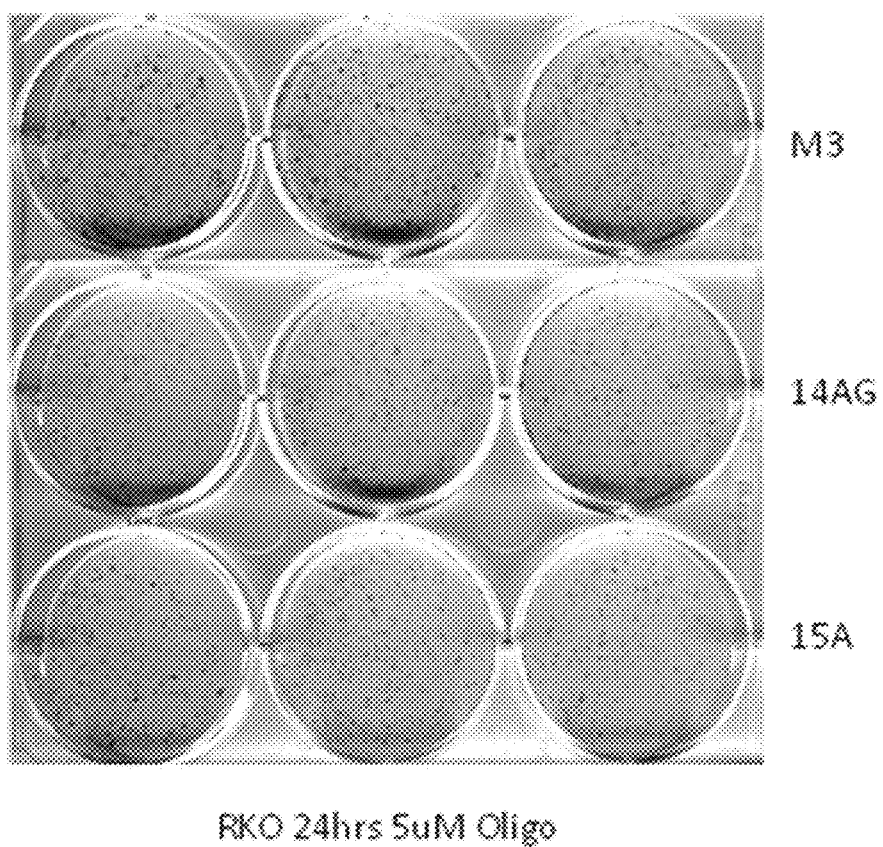
FIG. 30 shows a cell colony formation assay in RKO cells that were treated with 5 μM of the indicated oligonucleotides for 24 hours.

Another strategy is to use oligonucleotides to block the interaction between RBM38 and the 3' untranslated region (UTR) of p53 in order to modulate p53 translation (FIG. 26). To this end, a region of the p53 3' UTR where RBM38 interacts (FIG. 27) was identified (SEQ ID NO:15) and several oligonucleotides having complementarity to this sequence (e.g., SEQ ID NOS:16-21) were designed. As shown in FIG. 28, the 14A/G (SEQ ID NO:20) and 15A (SEQ ID NO:21) oligonucleotides unregulated p53 protein expression, but the M3 (SEQ ID NO:14) and 18T (SEQ ID NO:15) oligonucleotides did not. Similarly, the 14A/G and 15A oligonucleotides inhibited RKO tumor cell colony formation after 24 hours more than the M3 control oligonucleotide did (FIG. 30).

Figure 29A:
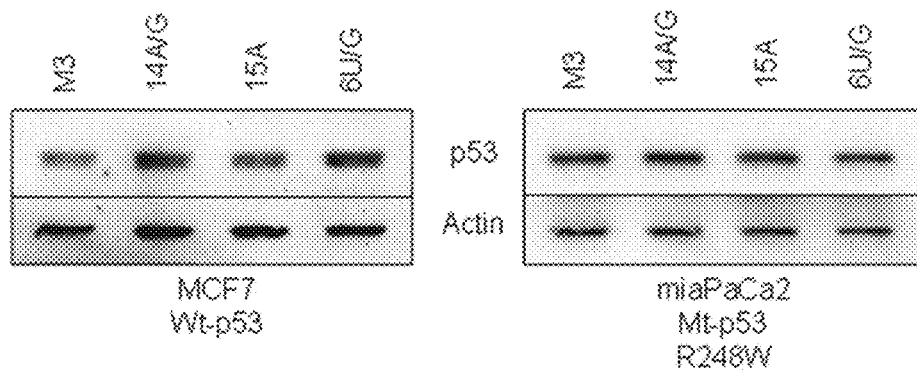
FIGS. 29A-29C show data illustrating the effects of oligonucleotides of the present invention with respect to wild type and mutant p53.
Figure 29B:
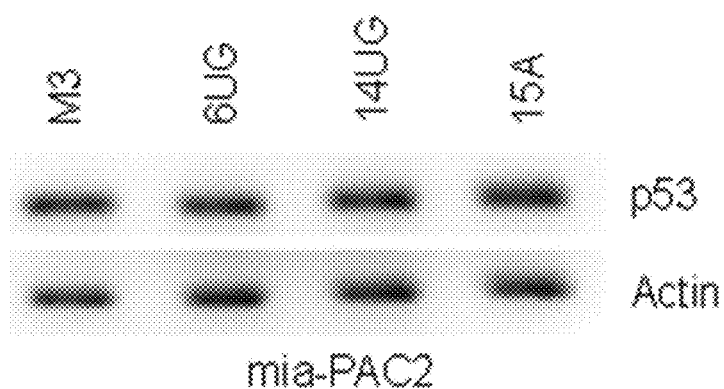
Figure 29C:
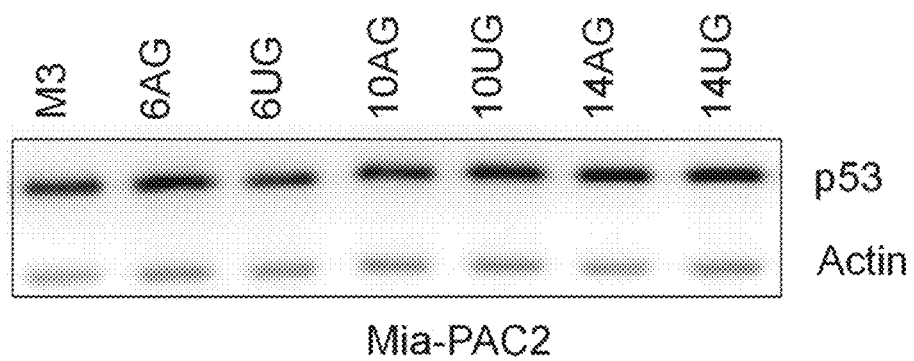

FIGS. 29A and 29B show the results of experiments exploring the effects of oligonucleotides of the present invention on wild type and mutant p53. Oligonucleotides M3, 14A/G, 15A, and 6U/G were used to treat MCF7 cells expressing wild type p53 and MIA-PaCa-2 cells expressing mutant p53 (R248W). Oligonucleotide 6U/G unregulated p53 expression in cells expressing wild type p53, but downregulated expression in cells expressing mutant p53. The effect was limited to the 6U/G oligonucleotide. FIG. 29C shows the effects of various oligonucleotides that were derivatives of the 18T oligonucleotide on p53 expression. Oligonucleotide sequences were as follows: M3, SEQ ID NO:14; 14A/G, SEQ ID NO:20; 14U/G, SEQ ID NO:49; 15A, SEQ ID NO:21; 6A/G, SEQ ID NO:45; 6U/G, SEQ ID NO:46; 10A/G, SEQ ID NO:47; 10 U/G, SEQ ID NO:48.

Example 3. Modulation of p53 Expression and eIF4E Phosphorylation

This example demonstrates that compositions and methods of the present invention inhibit phosphorylation of eIF4E, increase expression of p53 and downstream targets, and inhibit tumor cell growth. Furthermore, this example demonstrates that compositions and methods of the present invention exhibit a synergistic effect when combined with other anti-tumor agents.

Figure 31A:
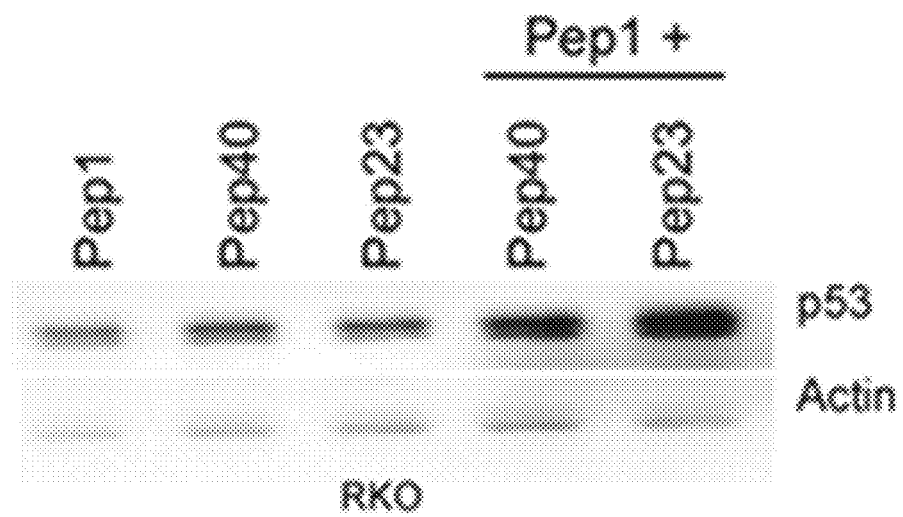
FIGS. 31A and 31B show that delivery of peptides was facilitated by co-treatment with cell-penetrating peptides.
Figure 31B:
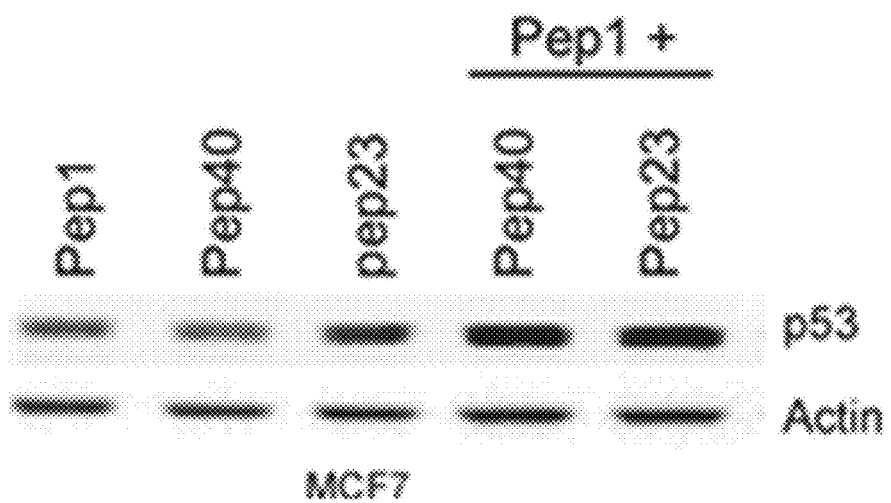

As shown in FIG. 31, cell-penetrating peptides (e.g., PEP1) facilitated cellular delivery of peptides of the present invention. RKO or MCF7 cells were grown in 12-well plates with a seed density of $1\times10^5$ a day before peptide addition. Peptides were added at a concentration of 6 µM for PEP1 or 300 nM for Pep40 and Pep23. For PEP1+Pep40/23, 300 nM Pep40/23 was added to 6 µM Pep1 in 100 µL serum-free DMEM for 30 minutes before being added to the cells for 24 hours. After 24 hours, cells were harvested with 1×SDS-lysis buffer (100 µL) and then lysate was run on a 12% SDS-PAGE gel followed by Western blotting for p53 and actin. As shown in FIG. 31, peptides alone could not be delivered into cells and did not increase p53 expression (lanes 1-3), whereas when delivered together with PEP1, both Pep40 and Pep23 were able to increase p53 expression in RKO colon cancer cells and MCF7 breast cancer cells (lanes 4-5).

Figure 32A:
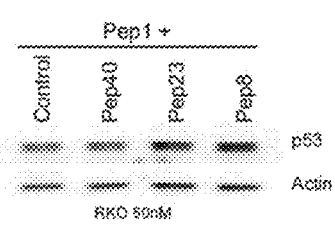
FIGS. 32A-32C show the induction of p53 expression by peptides of the present invention.

Next, experiments were performed to examine the effects of peptides of the present invention on RKO and MCF7 cells (FIG. 32). For the experiments shown in FIG. 32A, RKO cells were plated at a seed density of $1\times10^4$ cells per well in a 12-well plate the night before the addition of peptides. PEP1 was added at a concentration of 1 µM, whereas Pep40, Pep23, and Pep8 were added at a concentration of 50 nM. For PEP1+Pep40/23/8, 50 nM of Pep40/23 was added to 1 µM Pep1 in 100 µL serum-free DMEM for 20 minutes before being added to the cells for 18 hours. Subsequently, cells were harvested with 1×SDS-lysis buffer (150 µL) and then lysate was run on a 12% SDS-PAGE gel followed by Western blotting for p53 and actin. As shown in FIG. 32A, the 8-amino acid peptide (Pep8) could induce p53 protein levels at 50 nM concentration.

Figure 32B:
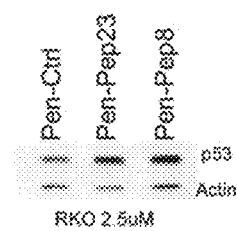
Figure 32C:
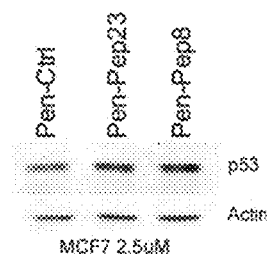

For the experiments shown in FIGS. 32B and 32C, RKO or MCF7 cells were plated in 12-well plates at a density of $2.5\times10^4$ cells per well. The next day they were treated with 2.5 µM Pen-Ctrl (SEQ ID NO:10), Pen-Pep23 (SEQ ID NO:9), or Pen-Pep8 (SEQ ID NO:50) for 18 hours. The cells were subsequently lysed with 125 µL 1×SDS-lysis buffer and then lysate was run on a 12% SDS gel followed by Western blotting for p53 and actin. As shown in FIGS. 32B and 32C, Penetratin™ fused to Pep23 and Pep8 (2.5 µM) induced p53 expression in RKO and MCF7 cells.

Figure 33A:
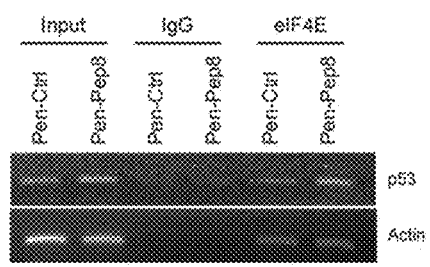
FIGS. 33A and 33B show the effects of peptides of the present invention on p53 expression and association with eIF4E.

RNA-ChIP assays were performed to examine how peptides of the present invention affect eIF4E association with p53 mRNA (FIG. 33). For the experiments shown in FIG. 33A, 4 10 cm plates were seeded with $2\times10^6$ RKO cells the night before. The next morning 2 plates were treated with 1.5 µM Pen-Ctrl (SEQ ID NO:10) and 2 plates were treated with 1.5 µM Pen-Pep8 (SEQ ID NO:50) for 2 hours. RKO cells were harvested in 1 mL per plate polysome lysis buffer, then centrifuged at 16,000×G for 15 minutes in a microcentrifuge at 4° C. The supernatant was pooled from all aliquots and transferred to a 15 ml tube. Equilibration was performed with 50% protein A-agarose slurry in polysome lysis buffer by washing twice with 0.5 mL of polysome lysis buffer and then restoring the original volume with lysis buffer. 3×200 µL tubes of agarose. For preclearing, one aliquot of equilibrated protein A-agarose beads was added to the lysate (50 µL of 50% agarose per 1 mL lysate) and incubated with rotation at 4° C. for 1 hour. Lysate was divided into microcentrifuge tubes and centrifuged briefly for 30 seconds to collect beads. Supernatant was pooled and transferred to a new 15 mL tube. After repeating the preclearing and bead collection steps, lysate was divided into 1 mL aliquots (i.e., 2×1 mL Pen-Ctrl and 2×1 mL Pen-Pep8). Antibodies were added (1 µg eIF4E or 1 µg IgG control) to the aliquots and incubated with rotation at 4° C. overnight. Afterward, 50 µL of protein A-agarose beads were added to each aliquot, followed by rotation at 4° C. for 4 hours, then centrifugation for 30 seconds to collect beads. Lysate was discarded. Beads were washed with 0.5 mL polysome lysis buffer four times at 4° C. with rotation for 5 minutes for each wash. Next, beads were washed four times with polysome lysis buffer including 1 M urea, as above. Beads were resuspended in 100 μL of polysome lysis buffer with 0.1% SDS and 30 μg proteinase K and incubated in a heating block at 50° C. for 30 minutes. Subsequently, one volume (100 μL) of phenol-chloroform-isoamyl alcohol mixture was added and vortexed to mix, then centrifuged for 1 minute to separate phases. The upper water phase was then recovered. The preceding resuspension, heating, and phenol-chloroform-isoamyl alcohol addition steps were repeated two times. Next, 10 μL yeast tRNA (1 mg/mL) was added to 12 μL 3 M sodium acetate, 250 μL ethanol, and 100 μL of water phase and mixed. Ethanol precipitation was performed at −20° C. overnight, followed by centrifugation for 20 minutes at 4° C. in a microcentrifuge at full speed (16,000 xG). Ethanol was thoroughly removed and the pellet was allowed to air dry until all liquid had evaporated. The pellet was then resuspended in 13 μL RT mixture containing dNTPs (500 μM each) and 100 nM gene-specific primers. Reverse transcription was performed using Superscript III according to the manufacturer's instructions. 20 μL PCR reactions were set up using Accuprime Supermix I according to the manufacturer's instructions. 1 μL of the 20 μL RT reaction was pipetted into a 20 μL PCR reaction for template. PCR reactions were run for 20-30 cycles Next, another set of PCR reactions was set up using 1 μL of the first-round PCR reaction as a template for each 20 μL second-round PCR reaction. These PCR reactions were run for 33 cycles (actin) or 45 cycles (p53). Visualization was performed by running 17 μL of each of the 20 μL PCR reactions on an agarose gel. As shown in FIG. 33A, RNA-ChIP assays revealed that Pen-Pep8 treatment for 2 hours resulted in increased eIF4E association with p53 mRNA.

Figure 33B:
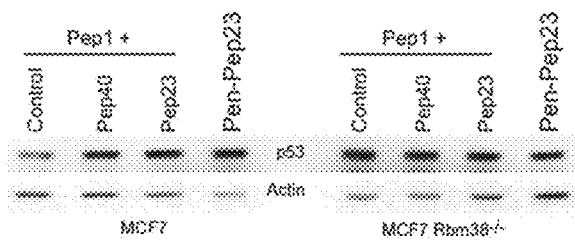

For the experiments shown in FIG. 33B, MCF7 wild-type or MCF7 RBM38 null cells were grown in 12-well plates with a seed density of 1×10$^5$ a day before peptide addition. Peptides were added at a concentration of 7.5 μM for PEP1 (SEQ ID NO:13), 375 nM for Pep40 (SEQ ID NO:2) and Pep23 (SEQ ID NO:3), or 5 μM for Pen-Pep23. For PEP1+Pep40/23, 375 nM of Pep40/23 was added to 7.5 μM PEP1 in 100 μL serum-free DMEM for 30 minutes before being added to the cells for 18 hours. Cells were harvested with 150 μL 1×SDS-lysis buffer and lysate was run on a 12% SDS-PAGE gel followed by Western blot for p53 and actin. As shown in FIG. 33B, peptides were specific for RBM38 and no increase of p53 was observed after addition of peptides in RBM38 null cells.

FIG. 34 shows a series of experiments that were performed to examine the effects of combining peptides of the present invention with additional anti-tumor agents. For the experiments shown in FIGS. 34A and 34B, RKO or MCF7 cells were grown the night before in a 6-well plate seeded with 2×10$^5$ cells per well. The next day, cells were treated with 2.5 μM Pen-Ctrl (SEQ ID NO:10) or Pen-Pep8 (SEQ ID NO:50) for 20 minutes then treated with 6.25 ng/mL doxorubicin for 18 hours. The following day, the cells were lysed with 1×SDS-lysis buffer (250 μL) and lysate was run on a 10% gel. 20 μL was loaded per well, followed by Western blot for p53 and actin. As shown in FIGS. 34A and 34B, addition of Pen-Pep8 and low dose doxorubicin (6.25 ng/mL) to both RKO and MCF7 cells resulted in robust p53 expression.

Figure 34A:
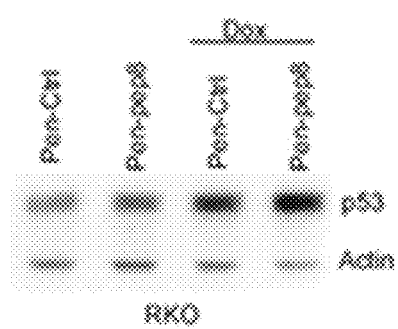
FIGS. 34A-34I show the ability of peptides of the present invention to sensitize tumor cells to treatment with other anti-tumor agents.
Figure 34B:
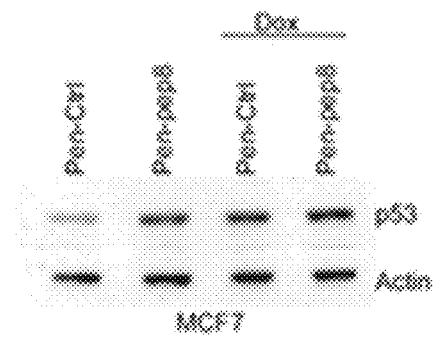
Figure 34C:
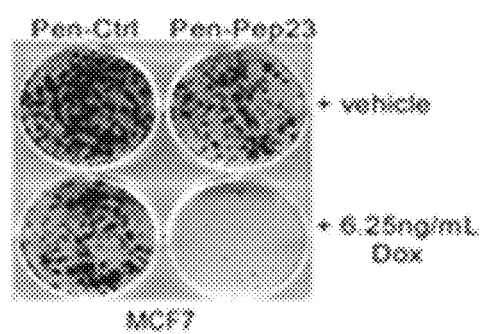

For the experiments shown in FIG. 34C, MCF7 cells were seeded on a 6-well plate at a seed density of 1×10$^3$ cells per well. The following day the cells were treated with 5 μM Pen-Ctrl or 5 μM Pen-Pep23. The following day, 6.25 ng/mL doxorubicin was added to the cells for 48 hours. Subsequently, the cell media was changed every 3 days until colonies were visible. The cells were fixed and stained with crystal violet.

Figure 34D:
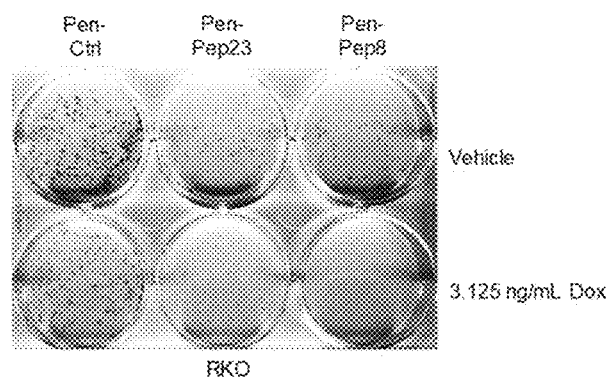

For the experiments shown in FIG. 34D, RKO cells were seeded on a 6-well plate at a seed density of 2×10$^3$ cells per well. The following day the cells were treated with 5 μM Pen-Ctrl, 5 μM Pen-Pep23, or 5 μM Pen-Pep8. The following day, 3.125 ng/mL doxorubicin was added to the cells for 48 hours. Subsequently, the cell media was changed every 3 days until colonies were visible. The cells were fixed and stained with crystal violet. As shown in FIGS. 34C and 34D, Pen-Pep8 and Pen-Pep23 sensitized MCF7 and RKO cells to low-dose doxorubicin.

Figure 34E:
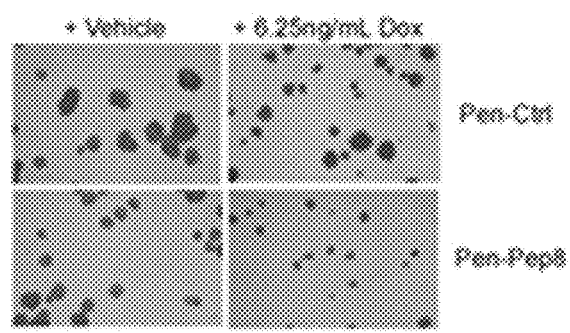
Figure 34F:
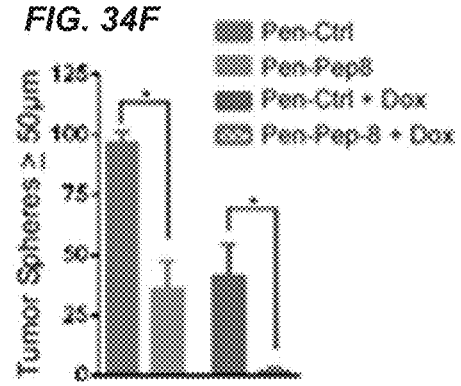

For the experiments shown in FIG. 34E, MCF7 cells were plated at a density of 20,000 cells per well using 2 mL Mammocult media in 6-well ultra-low adherent plates. The following day, cells were treated with Pen-Ctrl or Pen-Pep8 at a concentration of 5 μM. Peptides were added to each well for 20 minutes followed by 6.25 ng/mL doxorubicin. Cells were grown for 7 days and then the number of tumor spheres that were larger than 50 μm in diameter were counted (i.e., 20 10× photos were randomly taken and tumor spheres counted from the digital photos). For the graph shown in FIG. 34F, statistical analysis was performed using the student's t-test (n=3; *p≤0.05). The MCF7 tumor sphere assay demonstrated that Pen-Pep8 sensitized cells to low dose doxorubicin.

Figure 34G:
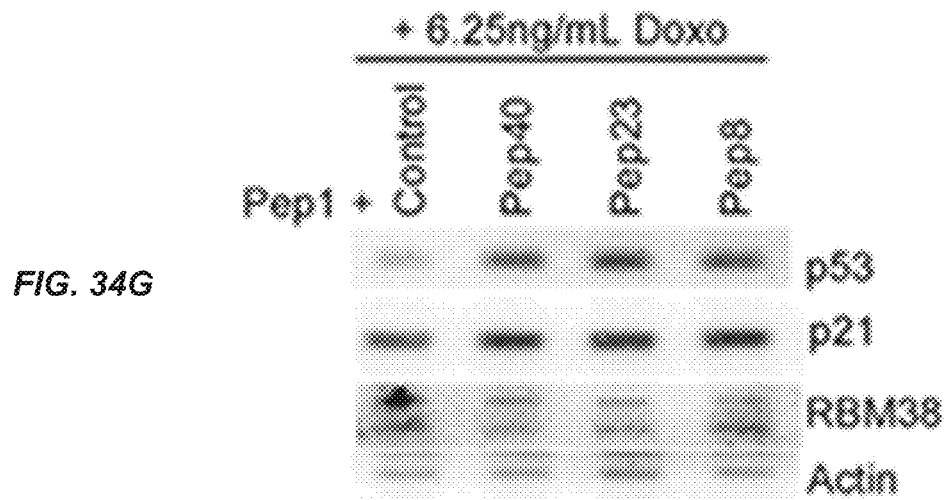

For the experiments shown in FIG. 34G, RKO cells were plated at a seed density of 1×10$^5$ cells per well in 12-well plates the night before the addition of peptides. Peptides were added at a concentration of 7.5 μM for PEP1 or 375 nM for Pep40, Pep23, and Pep8. For PEP1+Pep40/23/8, 375 nM of Pep40/23/8 was added to 7.5 μM PEP1 in 100 μL serum-free DMEM for 30 minutes before being added to the cells. 30 minutes later, 6.25 ng/mL doxorubicin was added to the cells for 18 hours. Cells were harvested with 1×SDS-lysis buffer (150 μL) and then lysate was run on a 12% SDS-PAGE gel followed by Western blotting for p53, p21, RBM38, and actin.

Figure 34H:
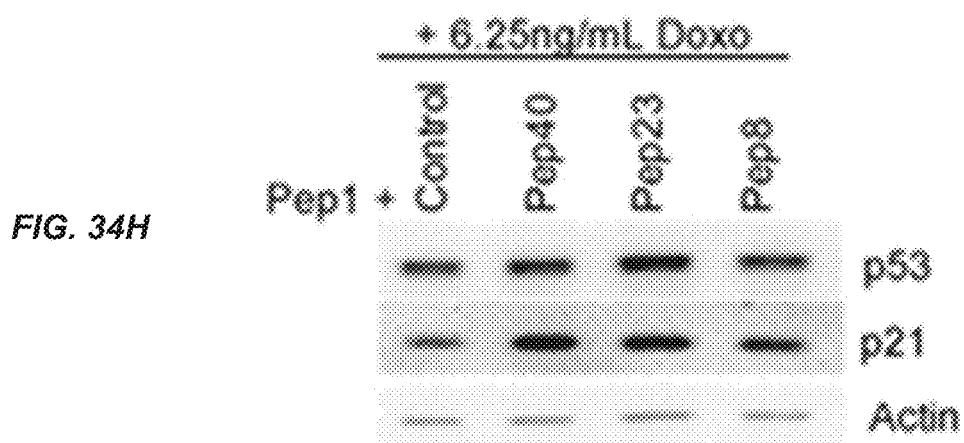

For the experiments shown in FIG. 34H, MCF7 cells were plated at a seed density of 1×10$^5$ cells per well in 12-well plates the night before the addition of peptides. Peptides were added at a concentration of 7.5 μM for PEP1 or 375 nM for Pep40, Pep23, and Pep8. For PEP1+Pep40/23/8, 375 nM of Pep40/23/8 was added to 7.5 μM PEP1 in 100 μL serum-free DMEM for 30 minutes before being added to the cells. 30 minutes later, 6.25 ng/mL doxorubicin was added to the cells for 18 hours. Cells were harvested with 1×SDS-lysis buffer (150 μL) and then lysate was run on a 12% SDS-PAGE gel followed by Western blotting for p53, p21, and actin. As shown in FIGS. 34G and 34H, PEP1 delivery of Pep40, Pep23 or Pep8 further increased p53 and p21 expression after low-dose doxorubicin treatment.

Figure 34I:
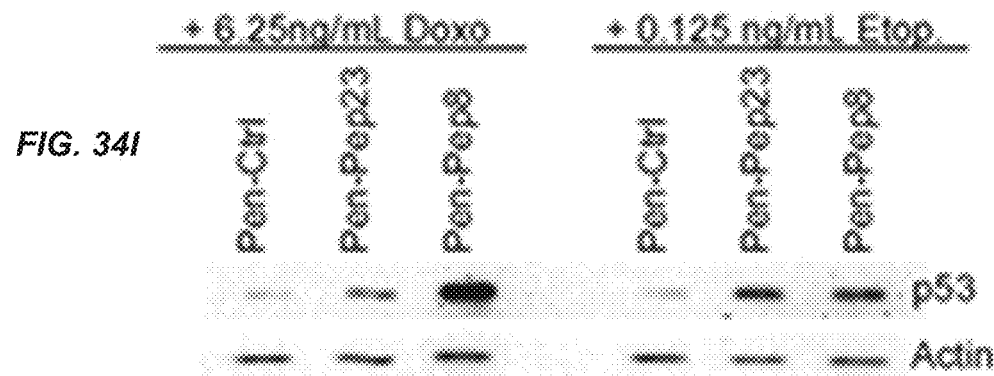

For the experiments shown in FIG. 34I, RKO cells were seeded at a density of 1×10$^5$ cells per well the night before the addition of the peptides in 12-well plates. Peptides were added at a concentration of 1.5 μM (Pen-Ctrl, Pen-Pep23, or Pen-Pep8) for 20 minutes, then either 6.25 ng/mL doxorubicin or 0.125 ng/mL etoposide was added for 18 hours. Cells were harvested with 150 μL 1×SDS-lysis buffer and lysate was run on a 12% SDS-PAGE gel followed by Western blotting for p53 and actin. This data shows that RKO cells were not only sensitized to low-dose doxorubicin following Pen-Pep23 or Pen-Pep8 treatment, but also to low-dose etoposide.

Figure 35A:
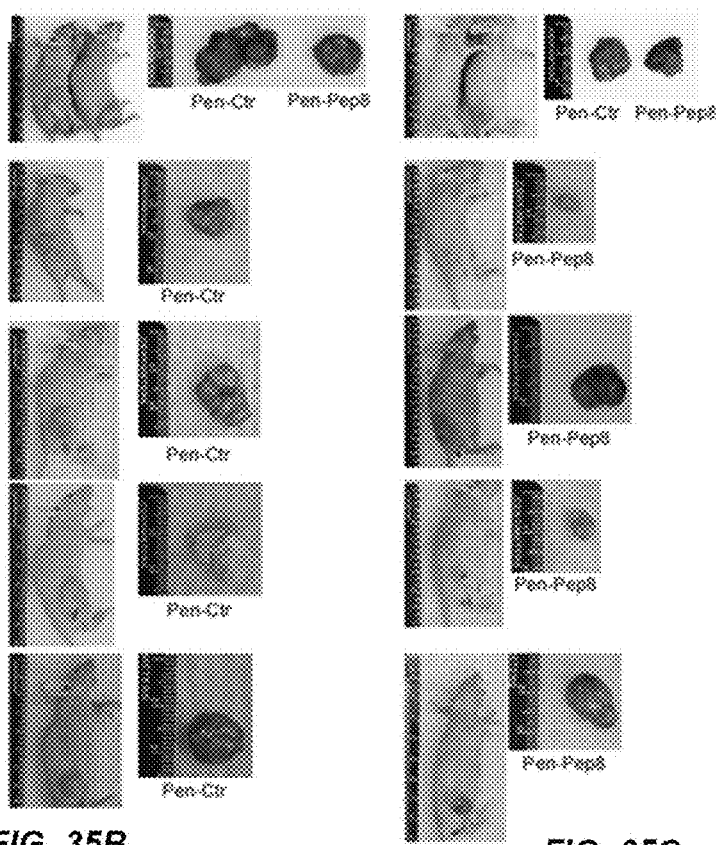
FIGS. 35A-35D show that peptides of the present invention inhibited RKO tumor xenograft growth.
Figure 35B:
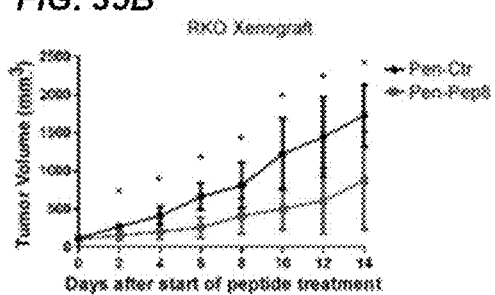
Figure 35C:
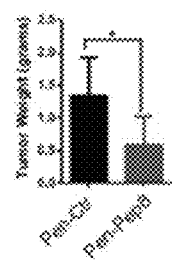
Figure 35D:
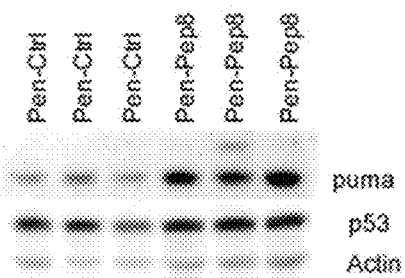

Experiments were also performed to demonstrate that Pen-Pep8 (SEQ ID NO:50) inhibited RKO tumor cell growth in a xenograft model (FIG. 35). 6-week-old female nude mice were used for the xenograft study (FIG. 35A). $1\times10^6$ RKO cells in a 1:1 mixture of matrigel:DMEM (serum-free) were injected into the right flank of the nude mice. After tumors had grown to a size of about 100 mm$^3$, treatment with either Pen-Ctrl or Pen-Pep8 (5 µM in 50 µL sterile PBS) was administered by intratumoral injection every 2 days for 2 weeks. After treatment, the animals were sacrificed and tumors were excised, measured, and weighed followed by being flash frozen (n=6 for each group). Xenograft volume over the course of treatment and final tumor weight after the animals were sacrificed are shown in FIGS. 35B and 35C, respectively. Furthermore, pieces of the frozen xenografts were cut using a sterile scalpel and then the tumor tissue was lysed and lysate was run on a 10% SDS-PAGE gel followed by Western blotting for Puma, p53, and actin. FIG. 35D shows that cell lysate from 3 pairs (Pen-Ctrl and Pen-Pep8) of RKO xenograft tumors exhibited increased p53 protein expression, as well as its target, Puma, following Pen-Pep8 treatment (n=6 for each group; *p≤0.05).

FIG. 36 shows the results of experiments that were performed to assess the efficacy of cyclic versions of peptides of the present invention. For the experiments shown in FIG. 36A, linear and cyclized versions of Pep8 (i.e., peptides having the amino acid sequences set forth in SEQ ID NOS:1, 5, 7, and 8) were synthesized and bound to TentaGel resin. Resin was washed 3× with 1× lysis buffer, and then incubated with 1× lysis buffer+0.3% BSA for 1 hour while rotating in a cold room. Next, resin was incubated with 1× lysis buffer+0.3% BSA+2 µg purified eIF4E (His-tagged) overnight. Next, resin was washed with 1× lysis buffer+0.3% BSA 3 times, followed by washing with 1× lysis buffer with no Triton X-100 three times. Finally, elution was performed with 1×SDS-loading buffer (70 µl) to load all onto a 12% SDS-PAGE gel for Western blot for His-tagged eIF4E. Disulfide cyclic Pep8 (peptide #2 in FIG. 36A; SEQ ID NO:5) bound the most eIF4E and was used for the next assay described below.

For the experiments shown in FIG. 36B, $1\times10^4$ RKO cells were seeded in each well of a 12-well plate. The next day, peptides were added to 100 µL serum-free DMEM at a concentration of 25 nM, 50 nM, 150 nM, or 375 nM for Ctrl and Cyc-Pep8 (disulfide) with PEP1 at a 20:1 molar ratio for 20 minutes, followed by addition to cells. After 18 hours, cells were harvested with 100 µL 1×SDS-lysis buffer and lysate was run on an SDS-PAGE gel followed by Western blot for p53 and actin. Cyclic Pep8 (SEQ ID NO:5) exhibited increased potency compared to other forms of Pep8, as shown by an increase of p53 with the addition of only 25 nM of the peptide.

For the experiments shown in FIG. 36C, MCF7 cells were plated at a density of 20,000 cells per well using 2 mL Mammocult media in 6-well ultra-low adherent plates. The following day, cells were treated with 150 nM Cyc-Ctrl or Cyc-Pep8 (SEQ ID NO:5). 150 nM Cyc-Ctr/Pep8 was incubated in 100 µL serum-free DMEM with 3 µg PEP1 for 25 minutes before being added to the cells. After 20 minutes, 3.125 ng/mL doxorubicin was added to the cells for 7 days. Cells were grown for 7 days and then tumor spheres were counted that were larger than 50 µm in diameter (i.e., 20 10× photos were randomly taken and tumor spheres were counted from the digital photos). As shown in FIG. 36C, 150 nM Cyc-Pep8 sensitized MCF7 tumor spheres to low-dose doxorubicin treatment.

FIG. 37 shows the results of a group of experiments that were performed to examine how peptides of the present invention modulate p53 expression and eIF4E phosphorylation. For the experiments shown in FIG. 37A, RKO cells were plated at a seed density of $1\times10^5$ cells per well in 12-well plates the night before the addition of peptides. For PEP1 (SEQ ID NO:13) plus Ctrl (SEQ ID NO:11), Pep8 (SEQ ID NO:1), Pep8-SR (SEQ ID NO:53), and Pep8-SK (SEQ ID NO:52), 375 nM of peptide was added to 7.5 µM PEP1 in 100 µL serum-free DMEM for 20 minutes before being added to the cells for 18 hours. After 18 hours, cells were harvested with 1×SDS-lysis buffer (150 µL) and then lysate was run on a 10% SDS-PAGE gel followed by Western blotting for p53, p-eIF4E (Ser209), and actin. The Pep8 mutants (i.e., Pep8-SR and Pep8-SK) showed a stronger ability to induce p53 protein expression compared to Pep8. In addition to increasing p53 protein levels, Pep8 peptides and mutant derivatives thereof were able to downregulate eIF4E phosphorylation.

Figure 37A:
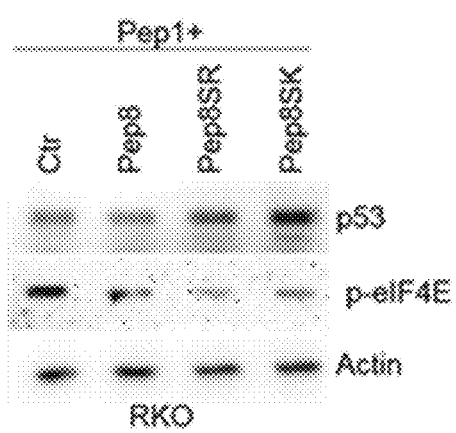
FIGS. 37A-37D show that mutant variants (SEQ ID NOS:52 and 53) of Pep8 (SEQ ID NO:1) exhibited increased ability to induce p53 expression.
Figure 37B:
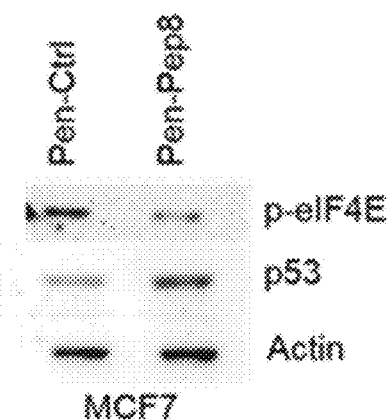

For the experiments shown in FIG. 37B, MCF7 cells were grown the night before in a 6-well plate seeded with $2\times10^5$ cells. The next day cells were treated with 2.5 µM Pen-Ctrl (SEQ ID NO:10) or Pen-Pep8 (SEQ ID NO:50) for 18 hours. The following day, the cells were lysed with 1×SDS-lysis buffer (250 µL) and lysate was run on a 10% SDS-PAGE gel. 20 µl was loaded per well followed by Western blot for p-eIF4E (Ser-209), p53, and actin. MCF7 breast cancer cells treated with Pen-Pep8 showed reduced p-eIF4E and increased p53 protein levels.

Figure 37C:
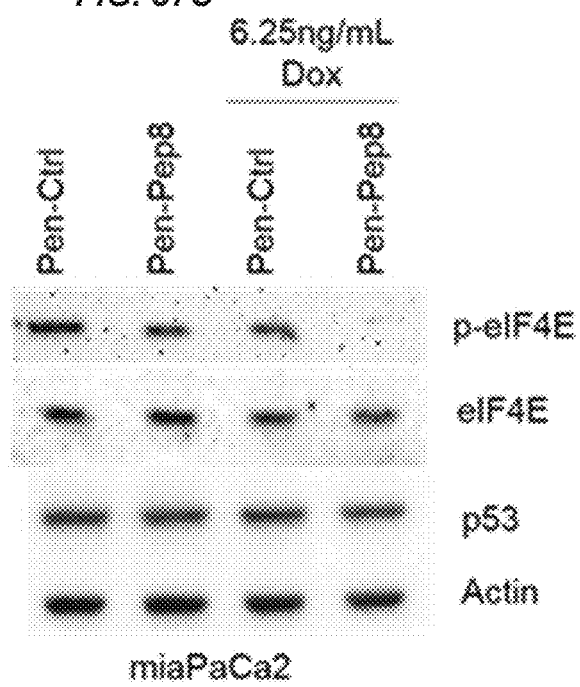

For the experiments shown in FIG. 37C, $2\times10^5$ miaPaCa2 cells per well were plated the day before in a 6-well plate. The following day, the cells were treated with 2.5 µM Pen-Ctrl (SEQ ID NO:10) or Pen-Pep8 (SEP ID NO:50) for 30 minutes then treated with 6.25 ng/mL doxorubicin for 18 hours. The following the day, the cells were harvested with 350 µL 1×SDS-lysis buffer and 20 µL of lysate was loaded per well onto a 10% SDS-PAGE gel followed by Western blot for total eIF4E, p-eIF4E (Ser209), p53 (mutant), and actin. Mutant p53 expressing miaPaCa2 cells showed decreased mutant p53 expression after Pen-Pep8 treatment. Concurrent with a reduction in mutant p53, Pen-Pep8 treatment produced a substantial decrease in p-eIF4E even after doxorubicin treatment.

Figure 37D:
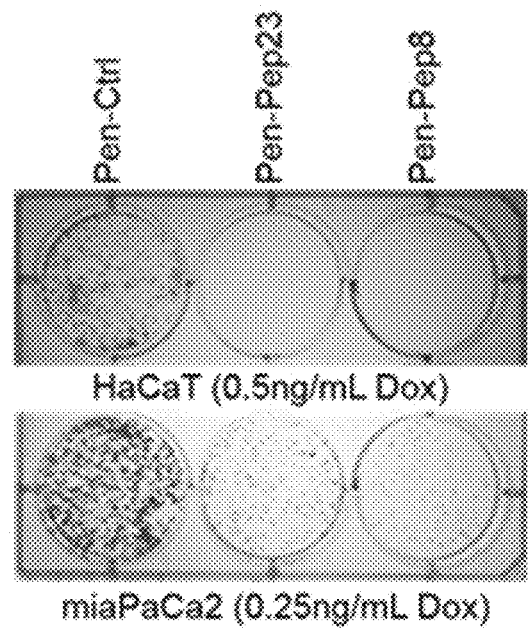

For the experiments shown in FIG. 37D, HaCaT and MiaPaCa2 cells were grown in 6-well plates at 500 cells per well. The following day, 10 µM Pen-Ctrl (SEQ ID NO:10), Pen-Pep23 (SEQ ID NO:9), or Pen-Pep8 (SEQ ID NO:50) were added to the cells for 20 minutes followed by treatment with 0.5 ng/mL doxorubicin (for HaCaT cells) or 0.25 ng/mL doxorubicin (for miaPaCa2 cells) for 18 hours, then the media was changed to fresh DMEM. After colonies formed they were fixed (i.e., using 7:1 MeOH:glacial acetic acid) and stained with crystal violet. The mutant p53 expressing cell lines HaCaT and miaPaCa2 were sensitized to low-dose doxorubicin when treated with Pen-Pep23 or Pen-Pep8 before being treated with doxorubicin, as shown by a decreased number of colonies (FIG. 37D).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Exemplary Embodiments

Exemplary embodiments provided in accordance with the presently disclosed subject matter include, but are not limited to, the claims and the following embodiments:

1. An isolated peptide comprising the amino acid sequence set forth in SEQ ID NO:1, 2, 3, 4, 52, 53, or 54.
2. The isolated peptide of embodiment 1, further comprising a D-lysine residue at the N-terminus and/or the C-terminus.
3. The isolated peptide of embodiment 1 or 2, further comprising a D-glutamic acid residue at the N-terminus and/or the C-terminus.
4. The isolated peptide of any one of embodiments 1 to 3, further comprising a D-cysteine residue at the N-terminus and/or the C-terminus.
5. The isolated peptide of any one of embodiments 1 to 4, wherein the peptide is cyclized.
6. The isolated peptide of any one of embodiments 1 to 5, wherein the peptide is about 5 to 100 amino acids in length.
7. The isolated peptide of embodiment 6, wherein the peptide is about 5 to 50 amino acids in length.
8. A conjugate comprising a peptide of any one of embodiments 1 to 7 and a cell-penetrating peptide (CPP).
9. The conjugate of embodiment 8, wherein the peptide and the CPP are covalently linked.
10. The conjugate of embodiment 8, wherein the peptide and the CPP are non-covalently associated.
11. The conjugate of any one of embodiments 8 to 10, wherein the CPP is selected from the group consisting of PEP1, Penetratin™ 1, and a combination thereof.
12. A composition comprising the peptide of any one of embodiments 1 to 7 or a plurality thereof, the conjugate of any one of embodiments 8 to 11 or a plurality thereof, or a combination thereof.
13. The composition of embodiment 12, wherein the peptide is present at a concentration of about 20 nM to about 400 nM.
14. The composition of embodiment 12 or 13, further comprising a chemotherapeutic agent.
15. The composition of embodiment 14, wherein the chemotherapeutic agent is a topoisomerase inhibitor.
16. The composition of embodiment 15, wherein the topoisomerase inhibitor is selected from the group consisting of a topoisomerase I inhibitor, a topoisomerase II inhibitor, and a combination thereof.
17. The composition of embodiment 15 or 16, wherein the topoisomerase inhibitor is selected from the group consisting of doxorubicin, etoposide, etoposide phosphate, teniposide, daunorubicin, mitoxantrone, amsacrine, an ellipticine, a fluoroquinolone, aurintricarboxylic acid, HU-331, irinotecan, topotecan, camptothecin, lamellarin D, resveratrol, genistein, quercetin, epigallocatechin gallate, and a combination thereof.
18. The composition of any one of embodiments 12 to 17, wherein the peptide or plurality thereof, conjugate or plurality thereof, and/or the chemotherapeutic agent are encapsulated by one or more liposomes.
19. A peptide-based pharmaceutical composition comprising the composition of any one of embodiments 12 to 18 and a pharmaceutically acceptable carrier.
20. An isolated oligonucleotide comprising the nucleotide sequence set forth in SEQ ID NO:16, 17, 18, 19, 20, 21, 45, 46, 47, 48, or 49.
21. The isolated oligonucleotide of embodiment 20, wherein the oligonucleotide is about 10 to 100 nucleotides in length.
22. The isolated oligonucleotide of embodiment 21, wherein the oligonucleotide is about 10 to 40 nucleotides in length.
23. An oligonucleotide-based pharmaceutical composition comprising the oligonucleotide of any one of embodiments 20 to 22 or a plurality thereof and a pharmaceutically acceptable carrier.
24. A nucleotide construct comprising a nucleotide sequence encoding a peptide comprising the amino acid sequence set forth in SEQ ID NO:1, 2, 3, 4, 52, 53, or 54.
25. The nucleotide construct of embodiment 24, wherein the encoded peptide is about 5 to 100 amino acids in length.
26. The nucleotide construct of embodiment 25, wherein the encoded peptide is about 5 to 50 amino acids in length.
27. The nucleotide construct of any one of embodiments 24 to 26, further comprising a nucleotide sequence encoding a cell-penetrating peptide (CPP).
28. A vector comprising the nucleotide construct of any one of embodiments 24 to 27.
29. A cell comprising one or more vectors of embodiment 28.
30. The cell of embodiment 29, wherein the cell expresses a peptide comprising the amino acid sequence set forth in SEQ ID NO:1, 2, 3, 4, 52, 53, or 54, a conjugate comprising a peptide comprising the amino acid sequence set forth in SEQ ID NO:1, 2, 3, 4, 52, 53, or 54 and a CPP, or a combination thereof.
31. The cell of embodiment 29 or 30, wherein the cell is first isolated from a subject before the one or more vectors are introduced into the cell.
32. The cell of embodiment 31, wherein the cell is introduced into the subject after the one or more vectors are introduced into the cell.
33. A method for preventing or treating cancer in a subject, the method comprising administering to the subject a therapeutically effective amount of the peptide-based pharmaceutical composition of embodiment 19, the oligonucleotide-based pharmaceutical composition of embodiment 23, the vector of embodiment 28, the cell of any one of embodiments 29 to 32, or a combination thereof.
34. The method of embodiment 33, further comprising delivering radiation therapy to the subject.
35. The method of embodiment 33 or 34, further comprising administering a chemotherapeutic agent to the subject.
36. The method of embodiment 35, wherein administering the peptide-based pharmaceutical composition, oligonucleotide-based pharmaceutical composition, vector, cell, or combination thereof to the subject enhances the effect of the chemotherapeutic agent.
37. The method of embodiment 35 or 36, wherein the chemotherapeutic agent is a type II topoisomerase inhibitor.
38. The method of embodiment 37, wherein the type II topoisomerase inhibitor is selected from the group consisting of doxorubicin, etoposide, and a combination thereof.
39. The method of any one of embodiments 33 to 38, wherein the subject does not have cancer.
40. The method of any one of embodiments 33 to 38, wherein treating the subject results in an improvement in one or more symptoms of the cancer.
41. The method of any one of embodiments 33 to 38 or 40, wherein treating the subject decreases the weight and/or volume of a cancer tumor.
42. The method of embodiment 41, wherein the weight and/or volume of the cancer tumor is decreased by at least about 50%.

43. The method of any one of embodiments 33 to 42, wherein a test sample is obtained from the subject before and/or after the peptide-based pharmaceutical composition, oligonucleotide-based pharmaceutical composition, vector, cell, or combination thereof is administered to the subject.
44. The method of embodiment 43, wherein the test sample comprises tissue, blood, or a combination thereof.
45. The method of embodiment 44, wherein the test tissue sample comprises cancer tissue.
46. The method of any one of embodiments 43 to 45, wherein the level of one or more biomarkers is determined in the test sample.
47. The method of embodiment 46, wherein the one or more biomarkers comprises p53 protein.
48. The method of embodiment 46 or 47, wherein the level of the one or more biomarkers in the test sample is compared to the level of the one or more biomarkers in a reference sample.
49. The method of embodiment 48, wherein the reference sample is normal tissue obtained from the same subject before and/or after the peptide-based pharmaceutical composition, oligonucleotide-based pharmaceutical composition, vector, cell, or combination thereof is administered to the subject.
50. The method of embodiment 48, wherein the reference sample is obtained from a different subject or a population of subjects.
51. The method of any one of embodiments 48 to 50, wherein the level of p53 protein in the test sample is lower than the level of p53 protein in the reference sample, and wherein the test sample is obtained before the peptide-based pharmaceutical composition, oligonucleotide-based pharmaceutical composition, vector, cell, or combination thereof is administered to the subject.
52. The method of any one of embodiments 47 to 51, wherein administering the peptide-based pharmaceutical composition, oligonucleotide-based pharmaceutical composition, vector, cell, or combination thereof to the subject results in an increase in the level of p53 protein in a test sample obtained from the subject after administration compared to a test sample obtained from the subject before administration.
53. A method for enhancing the effect of a chemotherapeutic agent in a subject receiving said chemotherapeutic agent, the method comprising administering to the subject a therapeutically effective amount of the peptide-based pharmaceutical composition of embodiment 19, the oligonucleotide-based pharmaceutical composition of embodiment 23, the vector of embodiment 28, the cell of any one of embodiments 29 to 32, or a combination thereof.
54. The method of embodiment 53, wherein the subject is being treated for cancer.
55. The method of embodiment 53 or 54, wherein the chemotherapeutic agent is a type II topoisomerase inhibitor.
56. The method of embodiment 55, wherein the type II topoisomerase inhibitor is selected from the group consisting of doxorubicin, etoposide, and a combination thereof.
57. A method for increasing p53 expression and/or activity in a subject, the method comprising administering to the subject a therapeutically effective amount of the peptide-based pharmaceutical composition of embodiment 19, the oligonucleotide-based pharmaceutical composition of embodiment 23, the vector of embodiment 28, the cell of any one of embodiments 29 to 32, or a combination thereof.
58. The method of embodiment 57, wherein p53 expression is increased.
59. The method of embodiment 58, wherein p53 mRNA expression is increased.
60. The method of embodiment 58, wherein p53 protein expression is increased.
61. The method of embodiment 57, wherein p53 activity is increased.
62. The method of any one of embodiments 57 to 61, wherein the association between eIF4E and p53 mRNA is increased.
63. The method of any one of embodiments 57 to 62, wherein the expression and/or activity of a downstream p53 target is increased.
64. The method of embodiment 63, wherein the downstream p53 target is selected from the group consisting of Puma, p21, and a combination thereof.
65. The method of any one of embodiments 57 to 64, wherein the expression and/or activity of p53 in a test sample obtained from the subject after the peptide-based pharmaceutical composition, oligonucleotide-based pharmaceutical composition, vector, cell, or combination thereof has been administered to the subject is increased at least about 1.2-fold compared to a control value.
The method of embodiment 65, wherein the control value is measured or determined in a reference sample.
67. The method of embodiment 66, wherein the reference sample is obtained from the subject before the peptide-based pharmaceutical composition, oligonucleotide-based pharmaceutical composition, vector, cell, or combination thereof is administered to the subject.
68. The method of embodiment 66, wherein the reference sample is obtained from a subject or population of subjects who are not administered the peptide-based pharmaceutical composition, oligonucleotide-based pharmaceutical composition, vector, cell, or combination thereof.
69. A method for decreasing eIF4E phosphorylation in a subject, the method comprising administering to the subject a therapeutically effective amount of the peptide-based pharmaceutical composition of embodiment 19, the oligonucleotide-based pharmaceutical composition of embodiment 23, the vector of embodiment 28, the cell of any one of embodiments 29 to 32, or a combination thereof.
70. The method of embodiment 69, wherein the ability of MNK1 and/or MNK2 to phosphorylate eIF4E is decreased.
71. The method of embodiment 69 or 70, wherein the phosphorylation of eIF4E at Ser209 is decreased.
72. A kit for preventing or treating cancer in a subject comprising the peptide-based pharmaceutical composition of embodiment 19, the oligonucleotide-based pharmaceutical composition of embodiment 23, the vector of embodiment 28, the cell of any one of embodiments 29 to 32, or a combination thereof.
73. The kit of embodiment 72, further comprising instructions for use.
74. The kit of embodiment 72 or 73, further comprising one or more reagents.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession numbers cited herein are hereby incorporated by reference in their entirety for all purposes.

| Informal Sequence Listing | | |
|---|---|---|
| SEQ ID NO: | Sequence | Title |
| 1 | YPYAASPA | peptide-8 (Pep8) |
| 2 | QYPPATYDQYPYAASPATAASFVGYSYPAAVPQALSAAAP | RBM38 (Pep40) |
| 3 | IGYQSHADTATKSGSTTKNRFVV | eIF4E (Pep23) |
| 4 | YPYAASPAAAGYVTAGGYGYAVQQP | RBM24 |
| 5 | cYPYAASPAc | Cyc-8 (cyc-Pep8) |
| 6 | cIGYQSHADTATKSGSTTKNRFVVc | Cyc-eIF4E |
| 7 | YPYAASPAe | Ami-8 |
| 8 | kYPYAASPAe | kAmi-8 |
| 9 | RQIKIWFQNRRMKWKKIGYQSHADTATKSGSTTKNRFVV | Pen-eIF4E (Pen-Pep23) |
| 10 | RQIKIWFQNRRMKWKKSTLWDTAELWQ | Pen-Control |
| 11 | STLWDTAELWQ | Control |
| 12 | RQIKIWFQNRRMKWKK | Pen (Penetratin™) |
| 13 | N-acetyl-KETWWETWWTEWSQPKKKRKV-Amide | PEP1 |
| 14 | GACACGCTTCCCAAA | M3 |
| 15 | TTTCTTTTTCTTTTTTTTTTTTTTTTCTTTTTCTT | 18T |
| 16 | AAAGAAAAAGAAAAAAAAAAAAAAAAGAAAAAGAA | 18T-AS |
| 17 | AAAGAAAAAGAAAAAAAAAAAAAAAAA | 18T-AS-29 |
| 18 | AAAGAAAAAGAAAAAAAA | 18T-AS-19 |
| 19 | AAAGAAAAAGAAAA | 18T-AS-15 |
| 20 | AAAAAAGAAAAAAAA | 14A/G |
| 21 | AAAAAAAAAAAAAAAA | 15A |
| 22 | MLLQPAPCAPSAGFPRPLAAPGAMHGSQKDTTFTKIFVGGLP YHTTDASLRKYFEGFGDIEEAVVITDRQTGKSRGYGFVTMAD RAAAERACKDPNPIIDGRKANVNLAYLGAKPRSLQTGFAIGV QQLHPTLIQRTYGLTPHYIYPPAIVQPSVVIPAAPVPSLSSPYIE YTPASPAYAQYPPATYDQYPYAASPATAASFVGYSYPAAVPQ ALSAAAPAGTTFVQYQAPQLQPDRMQ | RBM38 full sequence |
| 23 | MATVEPETTPTPNPPTTEEEKTESNQEVANPEHYIKHPLQNRW ALWFFKNDKSKTWQANLRLISKFDTVEDFWALYNHIQLSSNL MPGCDYSLFKDGIEPMWEDEKNKRGGRWLITLNKQQRRSDL DRFWLETLLCLIGESFDDYSDDVCGAVVNVRAKGDKIAIWTT ECENREAVTHIGRVYKERLGLPPKIVIGYQSHADTATKSGSTT KNRFVV | eIF4E full sequence |
| 24 | MHTTQKDTTYTKIFVGGLPYHTTDASLRKYFEVFGEIEEAVVI TDRQTGKSRGYGFVTMADRAAAERACKDPNPIIDGRKANVN LAYLGAKPRIMQPGXAFGVQQLHPALIQRPFGIPAHYVYPQA VQPGVVIPHVQPTAAAASTTPYIDYTGAAYAQYSAAAAAAA AAAAYDQYPYAASPAAAGYVTAGGYGYAVQQPITAAAPGT AAAAAAAAAAAAAFGQYQPQQLQTDRMQ | RBM24 full sequence |
| 25 | YGRKKRRQRRR | TAT |
| 26 | RGGRLSYSRRRFSTSTGR | SynB1 |
| 27 | RRLSYSRRRF | SynB3 |
| 28 | PIRRRKKLRRLK | PTD-4 |

| SEQ ID NO: | Sequence | Title |
|---|---|---|
| 29 | RRQRRTSKLMKR | PTD-5 |
| 30 | RRRRNRTRRNRRRVR | FHV Coat-(35-49) |
| 31 | KMTRAQRRAAARRNRWTAR | BMV Gag-(7,25) |
| 32 | TRRQRTRRARRNR | HTLV-II Rex-(4-16) |
| 33 | GRKKRRQRRRPPQ | D-Tat |
| 34 | GRRRRRRRRRPPQ | R9-Tat |
| 35 | GWTLNSAGYLLGKINLKALAALAKKIL | Transportan |
| 36 | KLALKLALKLALALKLA | MAP |
| 37 | MGLGLHLLVLAAALQGAWSQPKKKRKV | SBP |
| 38 | GALFLGWLGAAGSTMGAWSQPKKKRKV | FBP |
| 39 | N-acetyl-GALFLGFLGAAGSTMGAWSQPKKKRKV-Amide | MPG |
| 40 | N-acelyl-GALFLGFLGAAGSTMGAWSQPKSKRKV-Amide | MPG(ΔNLS) |
| 41 | N-acetyl-KETWFETWFTEWSQPKKKRKV-Amide | PEP2 |
| 42 | GAGGATTTCATCTCTTGTATATGATGATCTGGATCCACCAA GACTTGTTTTATGCTCAGGGTCAATTTCTTTTTTCTTTTTTT TTTTTTTTTCTTTTTCTTTGAGACTGGGTCTCGCTTTGTTGC CCAGGCTGGAGTG | p53 3' UTR |
| 43 | YPWAASPA | peptide-8YW |
| 44 | YPYAADPA | peptide-8SD |
| 45 | AAAGAAAAAGAAA | 6A/G |
| 46 | UUUGUUUUUGUUU | 6U/G |
| 47 | AAAAAGAAAAA | 10A/G |
| 48 | UUUUUGUUUUU | 10U/G |
| 49 | UUUUUUGUUUUUUUU | 14U/G |
| 50 | RQIKIWFQNRRMKWKKYPYAASPA | Pen-Pep8 |
| 51 | RQIKIWFQNRRMKWKKYPYAAKPA | Pen-Pep8SK |
| 52 | YPYAAKPA | peptide-8SK |
| 53 | YPYAARPA | peptide-8SR |
| 54 | YPYAAxPA | peptide-8 consensus sequence ("x" can be any independently selected amino acid) |
| 55 | RQIKIWFQNRRMKWKKYPYAARPA | Pen-Pep8SR |
| 56 | cYPYAAKPAc | Cyc-8SK (cyc-Pep8SK) |
| 57 | cYPYAARPAc | Cyc-8SR (cyc-Pep8SR) |
| 58 | cYPYAAxPAc | Cyc-8x (cyc-Pep8x) ("x" can be any independently selected amino acid) |
| 59 | YPYAAKPAe | Ami-8SK |
| 60 | YPYAARPAe | Ami-8SR |

| Informal Sequence Listing | | |
|---|---|---|
| SEQ ID NO: | Sequence | Title |
| 61 | YPYAAxPAe | Ami-8x ("x" can be any independently selected amino acid) |
| 62 | kYPYAAKPAe | kAmi-8SK |
| 63 | kYPYAARPAe | kAmi-8SR |
| 64 | kYPYAAxPAe | kAmi-8x ("x" can be any independently elected amino acid) |
| 65 | RQIKIWFQNRRMKWKKYPYAAxPA | Pen-Pep8x ("x" can be any independently selected amino acid) |

What is claimed is:

1. An isolated peptide comprising the amino acid sequence set forth in SEQ ID NO:1, 52, 53, or 54, wherein the isolated peptide is 8 to 10 amino acids in length.

2. The isolated peptide of claim 1, further comprising a D-lysine residue at the N-terminus and/or the C-terminus.

3. The isolated peptide of claim 1, further comprising a D-glutamic acid residue at the N-terminus and/or the C-terminus.

4. The isolated peptide of claim 1, further comprising a D-cysteine residue at the N-terminus and/or the C-terminus.

5. The isolated peptide of claim 1, wherein the peptide is cyclized.

6. A conjugate comprising a peptide of claim 1 and a cell-penetrating peptide (CPP).

7. The conjugate of claim 6, wherein the peptide and the CPP are covalently linked.

8. The conjugate of claim 6, wherein the peptide and the CPP are non-covalently associated.

9. The conjugate of claim 6, wherein the CPP is selected from the group consisting of PEP1 (SEQ ID NO:13), Penetratin (SEQ ID NO:12), and a combination thereof.

10. A composition comprising the peptide of claim 1 or a plurality thereof.

11. The composition of claim 10, wherein the peptide is present at a concentration of about 20 nM to about 400 nM.

12. The composition of claim 10, further comprising a chemotherapeutic agent.

13. The composition of claim 12, wherein the chemotherapeutic agent is a topoisomerase inhibitor.

14. The composition of claim 13, wherein the topoisomerase inhibitor is selected from the group consisting of a topoisomerase I inhibitor, a topoisomerase II inhibitor, and a combination thereof.

15. The composition of claim 13, wherein the topoisomerase inhibitor is selected from the group consisting of doxorubicin, etoposide, etoposide phosphate, teniposide, daunorubicin, mitoxantrone, amsacrine, an ellipticine, a fluoroquinolone, aurintricarboxylic acid, HU-331, irinotecan, topotecan, camptothecin, lamellarin D, resveratrol, genistein, quercetin, epigallocatechin gallate, and a combination thereof.

16. The composition of claim 12, wherein the peptide or plurality thereof and/or the chemotherapeutic agent are encapsulated by one or more liposomes.

17. A peptide-based pharmaceutical composition comprising the composition of claim 10 and a pharmaceutically acceptable carrier.

18. A kit for preventing or treating cancer in a subject comprising the peptide-based pharmaceutical composition of claim 17.

19. A conjugate comprising a peptide consisting of the amino acid sequence set forth in SEQ ID NO:1, 2, 4, 52, 53, or 54 and a cell penetrating peptide (CPP).

20. A method for preventing or treating cancer in a subject, the method comprising administering to the subject a therapeutically effective amount of the peptide-based pharmaceutical composition of claim 17.

21. The method of claim 20, further comprising delivering radiation therapy to the subject.

22. The method of claim 20, further comprising administering a chemotherapeutic agent to the subject.

23. The method of claim 22, wherein the chemotherapeutic agent is a type II topoisomerase inhibitor.

24. A method for enhancing the effect of a chemotherapeutic agent in a subject receiving said chemotherapeutic agent, the method comprising administering to the subject a therapeutically effective amount of the peptide-based pharmaceutical composition of claim 17.

25. The method of claim 24, wherein the subject is being treated for cancer.

26. The method of claim 24, wherein the chemotherapeutic agent is a type II topoisomerase inhibitor.

27. A method for increasing p53 expression and/or activity in a subject, the method comprising administering to the subject a therapeutically effective amount of the peptide-based pharmaceutical composition of claim 17.

28. The method of claim 27, wherein the association between eIF4E and p53 mRNA is increased.

29. The method of claim 27, wherein the expression and/or activity of a downstream p53 target is increased.

30. The method of claim 29, wherein the downstream p53 target is selected from the group consisting of Puma, p21, and a combination thereof.

31. A method for decreasing eIF4E phosphorylation in a subject, the method comprising administering to the subject a therapeutically effective amount of the peptide-based pharmaceutical composition of claim 17.

32. The method of claim 31, wherein the ability of MNK1 and/or MNK2 to phosphorylate eIF4E is decreased.

33. The method of claim 31, wherein the phosphorylation of eIF4E at Ser209 is decreased.

* * * * *